US011060070B2

(12) United States Patent
Noordman et al.

(10) Patent No.: US 11,060,070 B2
(45) Date of Patent: Jul. 13, 2021

(54) MUTATED REP ENCODING SEQUENCES FOR USE IN AAV PRODUCTION

(71) Applicant: uniQure IP B.V., Amsterdam (NL)

(72) Inventors: Yvet Noordman, Amsterdam (NL); Jacek Lubelski, Amsterdam (NL); Andrew Christian Bakker, Amsterdam (NL)

(73) Assignee: UNIQURE IP B.V., Amsterdam (NL)

( * ) Notice: Subject to any disclaimer, the term of this patent is extended or adjusted under 35 U.S.C. 154(b) by 0 days.

(21) Appl. No.: 16/514,758

(22) Filed: Jul. 17, 2019

(65) Prior Publication Data

US 2019/0338254 A1     Nov. 7, 2019

Related U.S. Application Data

(63) Continuation of application No. 15/862,997, filed on Jan. 5, 2018, now Pat. No. 10,400,221, which is a continuation of application No. 14/952,303, filed on Nov. 15, 2015, now Pat. No. 9,885,022, which is a continuation of application No. 13/583,920, filed as application No. PCT/NL2011/050170 on Mar. 11, 2011, now Pat. No. 9,228,174.

(60) Provisional application No. 61/312,845, filed on Mar. 11, 2010.

(51) Int. Cl.
| | |
|---|---|
| *C12N 7/00* | (2006.01) |
| *C12N 15/86* | (2006.01) |
| *C07K 14/005* | (2006.01) |
| *A61K 39/12* | (2006.01) |
| *A61K 39/23* | (2006.01) |

(52) U.S. Cl.
CPC ............. *C12N 7/00* (2013.01); *C07K 14/005* (2013.01); *C12N 15/86* (2013.01); *A61K 39/12* (2013.01); *A61K 39/23* (2013.01); *C12N 2710/14143* (2013.01); *C12N 2750/14143* (2013.01); *C12N 2750/14151* (2013.01); *C12N 2750/14152* (2013.01); *C12N 2800/105* (2013.01); *C12N 2800/50* (2013.01); *C12N 2800/90* (2013.01); *C12N 2820/00* (2013.01)

(58) Field of Classification Search
CPC ........ A61K 39/12; A61K 39/23; A61K 39/42; C12N 7/00; C12N 2750/00043; C12N 2750/14011; C12N 15/86; C12N 2710/14143; C12N 2820/00; C12N 2800/105; C12N 2800/50; C12N 2800/90; C12N 2750/14151
See application file for complete search history.

(56) References Cited

U.S. PATENT DOCUMENTS

| | | | |
|---|---|---|---|
| 8,512,981 | B2 | 8/2013 | Hermens et al. |
| 8,642,314 | B2 | 2/2014 | Bakker et al. |
| 8,697,417 | B2 | 4/2014 | Bakker et al. |
| 2002/0182595 | A1 | 12/2002 | Weitzman et al. |
| 2003/0148506 | A1 | 8/2003 | Kotin et al. |
| 2004/0197895 | A1 | 10/2004 | Kotin et al. |
| 2009/0191588 | A1 | 7/2009 | Hermens et al. |
| 2010/0261254 | A1 | 10/2010 | Bakker et al. |
| 2011/0136227 | A1 | 6/2011 | Bakker et al. |
| 2014/0127801 | A1 | 5/2014 | Bakker et al. |
| 2014/0186926 | A1 | 7/2014 | Bakker et al. |

FOREIGN PATENT DOCUMENTS

| | | |
|---|---|---|
| WO | WO-99/27110 A1 | 6/1999 |
| WO | WO-03/018820 A2 | 3/2003 |
| WO | WO-2007/148971 A2 | 12/2007 |
| WO | WO-2009/104964 A1 | 8/2009 |

OTHER PUBLICATIONS

Aucoin MG, Perrier M, Kamen AA. Production of adeno-associated viral vectors in insect cells using triple infection: optimization of baculovirus concentration ratios. Biotechnol Bioeng. Dec. 20, 2006;95(6):1081-92.*
Kotin RM. Large-scale recombinant adeno-associated virus production. Hum Mol Genet. Apr. 15, 2011;20(R1):R2-6. Epub Apr. 29, 2011.*
Rinaudo D, Lamartina S, Roscilli G, Ciliberto G, Toniatti C. Conditional site-specific integration into human chromosome 19 by using a ligand-dependent chimeric adeno-associated virus/Rep protein. J Virol. Jan. 2000;74(1):281-94.*
Di Pasquale G, Stacey SN. Adeno-associated virus Rep78 protein interacts with protein kinase A and its homolog PRKX and inhibits CREB-dependent transcriptional activation. J Virol. Oct. 1998;72(10):7916-25.*
McCarty DM, Ni TH, Muzyczka N. Analysis of mutations in adeno-associated virus Rep protein in vivo and in vitro. J Virol. Jul. 1992;66(7):4050-7.*
Berns Kl, et. al. Rep 78 protein [Adeno-associated virus-2], NCBI Reference Sequence: YP_680423.1. Pub. Dec. 8, 2008.*
Berns, et al. "Adeno-associated virus 2, complete genome", GenBank: AF043303.1, Dep. Feb. 24, 1998.

(Continued)

*Primary Examiner* — Rachel B Gill
(74) *Attorney, Agent, or Firm* — Foley & Lardner LLP; Sunk Talapatra

(57) ABSTRACT

Nucleic acids encoding Parvoviral Rep proteins with a mutated nuclear localization signal (NLS) are provided. Also provided is a nucleic acid comprising a nucleotide sequence encoding a Parvoviral Rep protein with a mutated zinc finger domain and a nucleic acid comprising a nucleotide sequence encoding a Parvoviral Rep protein comprising an amino acid mutation at position 43, 57, 79, 97, 120, 179, 305, 484, 493 or 571 with reference to SEQ ID NO: 2. Nucleic acid constructs and cells, such as insect cells, comprising the nucleic acids are provided as well as a method for producing a recombinant Parvoviral virion using the nucleic acids.

29 Claims, 22 Drawing Sheets

Specification includes a Sequence Listing.

(56) References Cited

OTHER PUBLICATIONS

Cassell G D et al: "Characterization of a nuclear localization signal in the C-terminus of the adeno-associated virus Rep68/78 proteins" Virology, Academic Press, Orlando, US, vol. 327, No. 2, Oct. 1, 2004 (Oct. 1, 2004), pp. 206-214, XP004537620.
Cathomen, et al. "A chimeric protein containing the N terminus of the adeno-associated virus Rep protein recognizes its target site in an in vivo assay", J. Virol (Mar. 2000), vol. 74, No. 5, pp. 2372-2382.
Chejanovsky N et al: "Mutagenesis of an AUG codon in the adeno-associated virus rep gene: Effects on viral DNA replication", Virology, Academic Press, Orlando, US, vol. 173, No. 1, Nov. 1, 1989, (Nov. 1, 1998), pp. 120-128, XP023050723.
Chen, "Intron splicing-mediated expression of AAV Rep and Cap genes and production of AAV vectors in insects cells", Mol Ther. (May 2008), Epub Mar. 18, 2008, vol. 16, No. 5, pp. 924-930.
Chen, et al. Rep78 protein [Adeno-associated virus], GenBank: AAU05365.1, Dep. Nov. 15, 2005.
Clark, K. "Recent advances in recombinant adeno-associated virus vector production", Kidney International Symposium, 2002, vol. 61, pp. S9-S15.
Communication pursuant to Article 94(3) EPC in EP Appln No. 11 730 092.1 dated May 6, 2015.
Hypothetical protein [*Arthrobacter* sp. LS16], NCBI Reference Sequence: WP_053799216, Deposited Sep. 13, 2015.
International Search Report for PCT/NL2011/050170—dated Nov. 14, 2011.
Kleinschmidt et al., "Sequence of elements of the adeno-associated virus rep gene required for suppression of herpes-simplex-virus-induced DNA amplification", Virology, 1995, vol. 206, pp. 254-262.
Kyoestio S. et al: "Analysis of Adeno-Associated Virus (AAV) Wild-Type and Mutant Rep Proteins for Their Abilities to Negatively Regulate AAV P5 and P19 MRNA Levels", Journal of Virology, The American Society for Microbiology, US, vol. 68, No. 5, May 1, 1994 (May 1, 1994), pp. 2947-2957, XP000651506.
PcDNA TM3.1/nV5-DEST Mammalian Expression Vector., Life Technologies, www.lifetechnologies.com/order/catalog/product/12290010, accessed online Feb. 5, 2015.
Ruffing et al., "Mutations in the carboxy terminus of adeno-associated virus 2 capsid proteins affect viral infectivity: lack of an RGD integrin-binding motif", Journal of General Virology, 1994, vol. 75, pp. 3385-3392.
Schmidt et al,. "Rep [Bovine adeno-associated virus]", NCBI Reference Sequence: YP_024970.1, Deposited Jun. 14, 2004.
Smith, et al. "Comparative Characterization of Rep Proteins from the Helper-Dependent Adeno-Associated Virus Type 2 and the Autonomous Goose Parvovirus", Journal of Virology (Apr. 1990) vol. 73, No. 4, pp. 2930-29.7.
Urabe, M. et al. "Insect Cells as a Factory to Produce Adeno-Associated Virus Type 2 Vectors", Human Gene Therapy, Nov. 1, 2002, vol. 13, pp. 1935-1943.
Weitzman M D et al: "Interaction of Wild-Type and Mutant Adeno-Associated Virus (AAV) Rep Proteins on AAV Hairpin DNA", Journal of Virology, The American Society for Microbiology, US, vol. 70, No. 4, Apr. 1, 1996 (Apr. 1, 1996), pp. 2440-2448, XP000651617.
Yang Q et al: "Mutational analysis of the adeno-associated virus rep gene", Journal of Virology, The American Society for Microbiology, US, vol. 66, No. 10, Oct. 1, 1992 (Oct. 1, 1992), pp. 6058-6069, XP002097159.
Zadori et al., "REP protein [Muscovy duck parvovirus]", NCBI Reference Sequence: YP_068410.1, Deposited Aug. 30, 2004.

* cited by examiner

Figure 4C  PstI-EagI restriction fragments:
5987: pVD142: PstI(6097) - PstI(1529)
2202: pVD142: EagI(1704) - EagI(3906)
1587: pVD142: EagI(3906) - PstI(5493)
604: pVD142: PstI(5493) - PstI(6097)
175: pVD142: PstI(1529) - EagI(1704)

PstI-EagI restriction fragments:
5987: pVD143: PstI(6176) - PstI(1529)
2288: pVD143: EagI(1704) - PstI(3992)
1463: pVD143: PstI(3992) - PstI(5455)
721: pVD143: PstI(5455) - PstI(6176)
175: pVD143: PstI(1529) - EagI(1704)

1) pVD142
2) pVD143
3) pVD142-Rep-EP1
4) pVD142-Rep-EP3

1) pVD143
2) 2.5µl viral DNA input
3) 10µl viral DNA input
4) 25µl viral DNA input
5) no DNA template 1) pVD142
2) pVD143
3) pVD142-select-EP3
4) pVD142-EP-EP3

```
              1                                                           60
pVD88   (1)   ACGGCGGGGTTCTACGAGATTGTGATTAAGGTCCCCAGCGACCTTGACGAGCATCTGCCC
pVD210  (1)   ACGGCGGGGTTCTACGAGATTGTGATTAAGGTCCCCAGCGACCTTGACGAGCATCTGCCC
pVD211  (1)   ACGGCGGGGTTCTACGAGATTGTGATTAAGGTCCCCAGCGACCTTGACGAGCATCTGCCC
pVD212  (1)   ACGGCGGGGTTCTACGAGATTGTGATTAAGGTCCCCAGCGACCTTGACGAGCATCTGCCC
pVD214  (1)   ACGGCGGGGTTCTACGAGATTGTGATTAAGGTCCCCAGCGACCTTGACGAGCATCTGCCC
pVD215  (1)   ACGGCGGGGTTCTACGAGATTGTGATTAAGGTCCCCAGCGACCTTGACGAGCATCTGCCC
pVD216  (1)   ACGGCGGGGTTCTACGAGATTGTGATTAAGGTCCCCAGCGACCTTGACGAGCATCTGCCC
pVD217  (1)   ACGGCGGGGTTCTACGAGATTGTGATTAAGGTCCCCAGCGACCTTGACGAGCATCTGCCC
pVD218  (1)   ACGGCGGGGTTCTACGAGATTGTGATTAAGGTCCCCAGCGACCTTGACGAGCATCTGCCC
pVD220  (1)   ACGGCGGGGTTCTACGAGATTGTGATTAAGGTCCCCAGCGACCTTGACGAGCATCTGCCC 61                                                          120
pVD88   (61)  GGCATTTCTGACAGCTTTGTGAACTGGGTGGCCGAGAAGGAATGGGAGTTGCCGCCAGAT
pVD210  (61)  GGCATTTCTGACAGCTTTGTGAACTGGGTGGCCGAGAAGGAATGGGAGTTGCCGCCAGAT
pVD211  (61)  GGCATTTCTGACAGCTTTGTGAACTGGGTGGCCGAGAAGGAATGGGAGTTGCCGCCAGAT
pVD212  (61)  GGCATTTCTGACAGCTTTGTGAACTGGGTGGCCGAGAAGGAATGGGAGTTGCCGCCAGAT
pVD214  (61)  GGCATTTCTGACAGCTTTGTGAACTGGGTGGCCGAGAAGGAATGGGAGTTGCCGCCAGAT
pVD215  (61)  GGCATTTCTGACAGCTTTGTGAACTGGGTGGCCGAGAAGGAATGGGAGTTGCCGCCAGAT
pVD216  (61)  GGCATTTCTGACAGCTTTGTGAACTGGGTGGCCGAGAAGGAATGGGAGTTGCCGCCAGAT
pVD217  (61)  GGCATTTCTGACAGCTTTGTGAACTGGGTGGCCGAGAAGGAATGGGAGTTGCCGCCAGAT
pVD218  (61)  GGCATTTCTGACAGCTTTGTGAACTGGGTGGCCGAGAAGGAATGGGAGTTGCCGCCAGAT
pVD220  (61)  GGCATTTCTGACAGCTTTGTGAACTGGGTGGCCGAGAAGGAATGGGAGTTGCCGCCAGAT 121                                                         180
pVD88   (121) TCTGACATGGATCTGAATCTGATTGAGCAGGCACCCCTGACCGTGGCCGAGAAGCTGCAG
pVD210  (121) TCTGACATGGATCTGAATCTGATTGAGCAGGCACCCCTGACCGTGGCCGAGAAGCTGCAG
pVD211  (121) TCTGACATGGATCTGAATCTGATTGAGCAGGCACCCCTGACCGTGGCCGAGAAGCTGCAG
pVD212  (121) TCTGACATGGATCTGAATCTGATTGAGCAGGCACCCCTGACCGTGGCCGGAAGCTGCAG
pVD214  (121) TCTGACATGGATCTGAATCTGATTGAGCAGGCACCCCTGACCGTGGCCGGAAGCTGCAG
pVD215  (121) TCTGACTGGATCTGAATCTGATTGAGCAGGCACCCCTGACCGTGGCCGAGAAGCTGCAG
pVD216  (121) TCTGACTGGATCTGAATCTGATTGAGCAGGCACCCCTGACCGTGGCCGAGAAGCTGCAG
pVD217  (121) TCTGACATGGATCTGAATCTGATTGAGCAGGCACCCCTGACCGTGGCCGAGAAGCTGCAG
pVD218  (121) TCTGACATGGATCTGAATCTGATTGAGCAGGCACCCCTGACCGTGGCCGAGAAGCTGCAG
pVD220  (121) TCTGACATGGATCTGAATCTGATTGAGCAGGCACCCCTGACCGTGGCCGGAAGCTGCAG 181                                                         240
pVD88   (181) CGCGACTTTCTGACGGAATGGCGCCGTGTGAGTAAGGCCCCGGAGGCCCTTTTCTTTGTG
pVD210  (181) CGCGACTTTCTGACGGAATGGCGCCGTGTGAGTAAGGCCCCGGAGGCCCTTTTCTTTGTG
pVD211  (181) CGCGACTTTCTGACGGAATGGCGCCGTGTGAGTAAGGCCCCGGAGGCCCTTTTCTTGTG
pVD212  (181) CGCGACTTTCTGACGGAATGGCGCCGTGTGAGTAAGGCCCCGGAGGCCCTTTTCTTTGTG
pVD214  (181) CGCGACTTTCTGACGGAATGGCGCCGTGTGAGTAAGGCCCCGGAGGCCCTTTTCTTTGTG
pVD215  (181) CGCGACTTTCTGACGGAATGGCGCCGTGTGAGTAAGGCCCCGGAGGCCCTTTTCTTGTG
pVD216  (181) CGCGACTTTCTGACGGAATGGCGCCGTGTGAGTAAGGCCCCGGAGGCCCTTTTCTTGTG
pVD217  (181) CGCGACTTTCTGACGGAATGGCGCCGTGTGAGTAAGGCCCCGGAGGCCCTTTTCTTGTG
pVD218  (181) CGCGACTTTCTGACGGAATGGCGCCGTGTGAGTAAGGCCCCGGAGGCCCTTTTCTTGTG
pVD220  (181) CGCGACTTTCTGACGGAATGGCGCCGTGTGAGTAAGGCCCCGGAGGCCCTTTTCTTTGTG 241                                                         300
pVD88   (241) CAATTTGAGAAGGGAGAGAGCTACTTCCACATGCACGTGCTCGTGGAAACCACCGGGGTG
pVD210  (241) CAATTTGAGAAGGGAGAGAGCTACTTCCACATGCACGTGCTCGTGGAAACCACCGGGGTG
pVD211  (241) CAATTTGAGAAGGGAGAGAGCTACTTCCACATGCACGTGCTCGTGGAAACCACCGGGGTG
pVD212  (241) CAATTTGAGAAGGGAGAGAGCTACTTCCACATGCACGTGCTCGTGGAACCACCGGGGTG
pVD214  (241) CAATTTGAGAAGGGAGAGAGCTACTTCCACATGCACGTGCTCGTGGAACCACCGGGGTG
pVD215  (241) CAATTTGAGAAGGGAGAGAGCTACTTCCACATGCACGTGCTCGTGGAAACCACCGGGGTG
pVD216  (241) CAATTTGAGAAGGGAGAGAGCTACTTCCACATGCACGTGCTCGTGGAAACCACCGGGGTG
pVD217  (241) CAATTTGAGAAGGGAGAGAGCTACTTCCACATGCACGTGCTCGTGGAAACCACCGGGGTG
pVD218  (241) CAATTTGAGAAGGGAGAGAGCTACTTCCACATGCACGTGCTCGTGGAAACCACCGGGGTG
pVD220  (241) CAATTTGAGAAGGGAGAGAGCTACTTCCACATGCACGTGCTCGTGGAACCACCGGGGTG
```

Fig. 16A

```
              301                                                          360
pVD88   (301) AAATCCATGGTTTTGGGACGTTTCCTGAGTCAGATTCGCGAAAAACTGATTCAGAGAATT
pVD210  (301) AAATCCATGGTTTTGGGACGTTTCCTGAGTCAGATTCGCGAAAAACTGATTCAGAGAATT
pVD211  (301) AAATCCATGGTTTTGGGACGTTTCCTGAGTCAGATTCGCGAAAAACTGATTCAGAGA TT
pVD212  (301) AAATCCATGGTTTTGGGACGTTTCCTGAGTCAGATTCGCGAAAAACTGATTCAGAGAATT
pVD214  (301) AAATCCATGGTTTTGGGACGTTTCCTGAGTCAGATTCGCGAAAAACTGATTCAGAGAATT
pVD215  (301) AAATCCATGGTTTTGGGACGTTTCCTGAGTCAGATTCGCGAAAAACTGATTCAGAGA TT
pVD216  (301) AAATCCATGGTTTTGGGACGTTTCCTGAGTCAGATTCGCGAAAAACTGATTCAGAGAATT
pVD217  (301) AAATCCATGGTTTTGGGACGTTTCCTGAGTCAGATTCGCGAAAAACTGATTCAGAGA TT
pVD218  (301) AAATCCATGGTTTTGGGACGTTTCCTGAGTCAGATTCGCGAAAAACTGATTCAGAGA TT
pVD220  (301) AAATCCATGGTTTTGGGACGTTTCCTGAGTCAGATTCGCGAAAAACTGATTCAGAGAATT 361                                                          420
pVD88   (361) TACCGCGGGATCGAGCCGACTTTGCCAAACTGGTTCGCGGTCACAAAGACCAGAAATGGC
pVD210  (361) TACCGCGGGATCGAGCCGACTTTGCCAAACTGGTTCGCGGTCACAAAGACCAGAAATGGC
pVD211  (361) TACCGCGGGATCGAGCCGACTTTGCCAAACTGGTTCGCGGTCACAAAGACCAGAAATGGC
pVD212  (361) TACCGCGGGATCGAGCCGACTTTGCCAAACTGGTTCGCGGTCACAAAGACCAGAAATGGC
pVD214  (361) TACCGCGGGATCGAGCCGACTTTGCCAAACTGGTTCGCGGTCACAAAGACCAGAAATGGC
pVD215  (361) TACCGCGGGATCGAGCCGACTTTGCCAAACTGGTTCGCGGTCACAAAGACCAGAAATGGC
pVD216  (361) TACCGCGGGATCGAGCCGACTTTGCCAAACTGGTTCGCGGTCACAAAGACCAGAAATGGC
pVD217  (361) TACCGCGGGATCGAGCCGACTTTGCCAAACTGGTTCGCGGTCACAAAGACCAGAAATGGC
pVD218  (361) TACCGCGGGATCGAGCCGACTTTGCCAAACTGGTTCGCGGTCACAAAGACCAGAAATGGC
pVD220  (361) TACCGCGGGATCGAGCCGACTTTGCCAAACTGGTTCGCGGTCACAAAGACCAGAAATGGC 421                                                          480
pVD88   (421) GCCGGAGGCGGGAACAAGGTGGTGGATGAGTGCTACATCCCCAATTACTTGCTCCCCAAA
pVD210  (421) GCCGGAGGCGGGAACAAGGTGGTGGATGAGTGCTACATCCCCAATTACTTGCTCCCCAAA
pVD211  (421) GCCGGAGGCGGGAACAAGGTGGTGGATGAGTGCTACATCCCCAATTACTTGCTCCCCAAA
pVD212  (421) GCCGGAGGCGGGAACAAGGTGGTGGATGAGTGCTACATCCCCAATTACTTGCTCCCCAAA
pVD214  (421) GCCGGAGGCGGGAACAAGGTGGTGGATGAGTGCTACATCCCCAATTACTTGCTCCCCAAA
pVD215  (421) GCCGGAGGCGGGAACAAGGTGGTGGATGAGTGCTACATCCCCAATTACTTGCTCCCCAAA
pVD216  (421) GCCGGAGGCGGGAACAAGGTGGTGGATGAGTGCTACATCCCCAATTACTTGCTCCCCAAA
pVD217  (421) GCCGGAGGCGGGAACAAGGTGGTGGATGAGTGCTACATCCCCAATTACTTGCTCCCCAAA
pVD218  (421) GCCGGAGGCGGGAACAAGGTGGTGGATGAGTGCTACATCCCCAATTACTTGCTCCCCAAA
pVD220  (421) GCCGGAGGCGGGAACAAGGTGGTGGATGAGTGCTACATCCCCAATTACTTGCTCCCCAAA 481                                                          540
pVD88   (481) ACCCAGCCTGAGCTCCAGTGGGCGTGGACTAATATGGAACAGTATTTAAGCGCCTGTTTG
pVD210  (481) ACCCAGCCTGAGCTCCAGTGGGCGTGGACTAATATGGAACAGTATTTAAGCGCCTGTTTG
pVD211  (481) ACCCAGCCTGAGCTCCAGTGGGCGTGGACTAATATGGAACAGTATTTAAGCGCCTGTTTG
pVD212  (481) ACCCAGCCTGAGCTCCAGTGGGCGTGGACTAATATGGAACAGTATTTAAGCGCC TGTTTG
pVD214  (481) ACCCAGCCTGAGCTCCAGTGGGCGTGGACTAATATGGAACAGTATTTAAGCGCC GTTTG
pVD215  (481) ACCCAGCCTGAGCTCCAGTGGGCGTGGACTAATATGGAACAGTATTTAAGCGCCTGTTTG
pVD216  (481) ACCCAGCCTGAGCTCCAGTGGGCGTGGACTAATATGGAACAGTATTTAAGCGCCTGTTTG
pVD217  (481) ACCCAGCCTGAGCTCCAGTGGGCGTGGACTAATATGGAACAGTATTTAAGCGCCTGTTTG
pVD218  (481) ACCCAGCCTGAGCTCCAGTGGGCGTGGACTAATATGGAACAGTATTTAAGCGCCTGTTTG
pVD220  (481) ACCCAGCCTGAGCTCCAGTGGGCGTGGACTAATATGGAACAGTATTTAAGCGCC GTTTG 541                                                          600
pVD88   (541) AATCTCACGGAGCGTAAACGGTTGGTGGCGCAGCATCTGACGCACGTGTCGCAGACGCAG
pVD210  (541) AATCTCACGGAGCGTAAACGGTTGGTGGCGCAGCATCTGACGCACGTGTCGCAGACGCAG
pVD211  (541) AATCTCACGGAGCGTAAACGGTTGGTGGCGCAGCATCTGACGCACGTGTCGCAGACGCAG
pVD212  (541) AATCTCACGGAGCGTAAACGGTTGGTGGCGCAGCATCTGACGCACGTGTCGCAGACGCAG
pVD214  (541) AATCTCACGGAGCGTAAACGGTTGGTGGCGCAGCATCTGACGCACGTGTCGCAGACGCAG
pVD215  (541) AATCTCACGGAGCGTAAACGGTTGGTGGCGCAGCATCTGACGCACGTGTCGCAGACGCAG
pVD216  (541) AATCTCACGGAGCGTAAACGGTTGGTGGCGCAGCATCTGACGCACGTGTCGCAGACGCAG
pVD217  (541) AATCTCACGGAGCGTAAACGGTTGGTGGCGCAGCATCTGACGCACGTGTCGCAGACGCAG
pVD218  (541) AATCTCACGGAGCGTAAACGGTTGGTGGCGCAGCATCTGACGCACGTGTCGCAGACGCAG
pVD220  (541) AATCTCACGGAGCGTAAACGGTTGGTGGCGCAGCATCTGACGCACGTGTCGCAGACGCAG
```

Fig. 16B

```
              601                                                           660
pVD88   (601) GAGCAGAACAAAGAGAATCAGAATCCCAATTCTGATGCGCCGGTGATCAGATCAAAAACT
pVD210  (601) GAGCAGAACAAAGAGAATCAGAATCCCAATTCTGATGCGCCGGTGATCAGATCAAAAACT
pVD211  (601) GAGCAGAACAAAGAGAATCAGAATCCCAATTCTGATGCGCCGGTGATCAGATCAAAAACT
pVD212  (601) GAGCAGAACAAAGAGAATCAGAATCCCAATTCTGATGCGCC GTGATCAGATCAAAAACT
pVD214  (601) GAGCAGAACAAAGAGAATCAGAATCCCAATTCTGATGCGCC GTGATCAGATCAAAAACT
pVD215  (601) GAGCAGAACAAAGAGAATCAGAATCCCAATTC GATGCGCCGGTGATCAGATCAAAAACT
pVD216  (601) GAGCAGAACAAAGAGAATCAGAATCCCAATTCTGATGCGCCGGTGATCAGATCAAAAACT
pVD217  (601) GAGCAGAACAAAGAGAATCAGAATCCCAATTCTGATGCGCCGGTGATCAGATCAAAAACT
pVD218  (601) GAGCAGAACAAAGAGAATCAGAATCCCAATTCTGATGCGCCGGTGATCAGATCAAAAACT
pVD220  (601) GAGCAGAACAAAGAGAATCAGAATCCCAATTCTGATGCGCC GTGATCAGATCAAAAACT 661                                                           720
pVD88   (661) TCAGCCAGGTACATGGAGCTGGTCGGGTGGCTCGTGGACAAGGGGATTACCTCGGAGAAG
pVD210  (661) TCAGCCAGGTACATGGAGCTGGTCGGGTGGCTCGTGGACAAGGGGATTACCTCGGAGAAG
pVD211  (661) TCAGCCAGGTACATGGAGCTGGTCGGGTGGCTCGTGGACAAGGGGATTACCTCGGAGAAG
pVD212  (661) CAGTGGATCCAGGAGGACCAGGCCTCATACATCTCCTTCAATGCGGCCTCCAACTCGCGG
pVD214  (661) TCAGCCAGGTACATGGAGCTGGTCGGGTGGCTCGTGGACAAGGGGATTACCTCGGAGAAG
pVD215  (661) TCAGCCAGGTACATGGAGCTGGTCGGGTGGCTCGTGGACAAGGGGATTACCTCGGAGAAG
pVD216  (661) TCAGCCAGGTACATGGAGCTGGTCGGGTGGCTCGTGGACAAGGGGATTACCTCGGAGAAG
pVD217  (661) TCAGCCAGGTACATGGAGCTGGTCGGGTGGCTCGTGGACAAGGGGATTACCTCGGAGAAG
pVD218  (661) TCAGCCAGGTACATGGAGCTGGTCGGGTGGCTCGTGGACAAGGGGATTACCTCGGAGAAG
pVD220  (661) TCAGCCAGGTACATGGAGCTGGTCGGGTGGCTCGTGGACAAGGGGATTACCTCGGAGAAG 721                                                           780
pVD88   (721) CAGTGGATCCAGGAGGACCAGGCCTCATACATCTCCTTCAATGCGGCCTCCAACTCGCGG
pVD210  (721) CAGTGGATCCAGGAGGACCAGGCCTCATACATCTCCTTCAATGCGGCCTCCAACTCGCGG
pVD211  (721) CAGTGGATCCAGGAGGACCAGGCCTCATACATCTCCTTCAATGCGGCCTCCAACTCGCGG
pVD212  (721) CAGTGGATCCAGGAGGACCAGGCCTCATACATCTCCTTCAATGCGGCCTCCAACTCGCGG
pVD214  (721) CAGTGGATCCAGGAGGACCAGGCCTCATACATCTCCTTCAATGCGGCCTCCAACTCGCGG
pVD215  (721) CAGTGGATCCAGGAGGACCAGGCCTCATACATCTCCTTCAATGCGGCCTCCAACTCGCGG
pVD216  (721) CAGTGGATCCAGGAGGACCAGGCCTCATACATCTCCTTCAATGCGGCCTCCAACTCGCGG
pVD217  (721) CAGTGGATCCAGGAGGACCAGGCCTCATACATCTCCTTCAATGCGGCCTCCAACTCGCGG
pVD218  (721) CAGTGGATCCAGGAGGACCAGGCCTCATACATCTCCTTCAATGCGGCCTCCAACTCGCGG
pVD220  (721) CAGTGGATCCAGGAGGACCAGGCCTCATACATCTCCTTCAATGCGGCCTCCAACTCGCGG 781                                                           840
pVD88   (781) TCCCAAATCAAGGCTGCCTTGGACAATGCGGGAAAGATTATGAGCCTGACTAAAACCGCC
pVD210  (781) TCCCAAATCAAGGCTGCCTTGGACAATGCGGGAAAGATTATGAGCCTGACTAAAACCGCC
pVD211  (781) TCCCAAATCAAGGCTGCCTTGGACAATGCGGGAAAGATTATGAGCCTGACTAAAACCGCC
pVD212  (781) TCCCAAATCAAGGCTGCCTTGGACAATGCGGGAAAGATTATGAGCCTGACTAAAACCGCC
pVD214  (781) TCCCAAATCAAGGCTGCCTTGGACAATGCGGGAAAGATTATGAGCCTGACTAAAACCGCC
pVD215  (781) TCCCAAATCAAGGCTGCCTTGGACAATGCGGGAAAGATTATGAGCCTGACTAAAACCGCC
pVD216  (781) TCCCAAATCAAGGCTGCCTTGGACAATGCGGGAAAGATTATGAGCCTGACTAAAACCGCC
pVD217  (781) TCCCAAATCAAGGCTGCCTTGGACAATGCGGGAAAGATTATGAGCCTGACTAAAACCGCC
pVD218  (781) TCCCAAATCAAGGCTGCCTTGGACAATGCGGGAAAGATTATGAGCCTGACTAAAACCGCC
pVD220  (781) TCCCAAATCAAGGCTGCCTTGGACAATGCGGGAAAGATTATGAGCCTGACTAAAACCGCC 841                                                           900
pVD88   (841) CCCGACTACCTGGTGGGCCAGCAGCCCGTGGAGGACATTTCCAGCAATCGGATTTATAAA
pVD210  (841) CCCGACTACCTGGTGGGCCAGCAGCCCGTGGAGGACATTTCCAGCAATCGGATTTATAAA
pVD211  (841) CCCGACTACCTGGTGGGCCAGCAGCCCGTGGAGGACATTTCCAGCAATCGGATTTATAAA
pVD212  (841) CCCGACTACCTGGTGGGCCAGCAGCCCGTGGAGGACATTTCCAGCAATCGGATTTATAAA
pVD214  (841) CCCGACTACCTGGTGGGCCAGCAGCCCGTGGAGGACATTTCCAGCAATCGGAT TATAAA
pVD215  (841) CCCGACTACCTGGTGGGCCAGCAGCCCGTGGAGGACATTTCCAGCAATCGGATTTATAAA
pVD216  (841) CCCGACTACCTGGTGGGCCAGCAGCCCGTGGAGGACATTTCCAGCAATCGGATTTATAAA
pVD217  (841) CCCGACTACCTGGTGGGCCAGCAGCCCGTGGAGGACATTTCCAGCAATCGGATTTATAAA
pVD218  (841) CCCGACTACCTGGTGGGCCAGCAGCCCGTGGAGGACATTTCCAGCAATCGGATTTATAAA
```

Fig. 16C

```
              901                                                          960
pVD88   (901) ATTTTGGAACTAAACGGGTACGATCCCCAATATGCGGCTTCCGTCTTTCTGGGATGGGCC
pVD210  (901) ATTTTGGAACTAAACGGGTACGATCCCCAATATGCGGCTTCCGTCTTTCTGGGATGGGCC
pVD211  (901) ATTTTGGAACTAAACGGGTACGATCCCCAATATGCGGCTTCCGTCTTTCTGGGATGGGCC
pVD212  (901) ATTTTGGAACTAAACGGGTACGATCCCCAATATGCGGCTTCCGTCTTTCTGGGATGGGCC
pVD214  (901) ATTTTGGAACTAAACGGGTACGATCCCCAATATGCGGCTTCCGTCTTTCTGGGATGGGCC
pVD215  (901) ATTTTGGAACTAAACGGGTACGATCCCCAATATGCGGCTTCCGTCTTTCTGGGATGGGCC
pVD216  (901) ATTTTGGAACTAAACGGGTACGATCCCCAATATGCGGCTTCCGTCTTTCTGGGATGGGCC
pVD217  (901) ATTTTGGAACTAAACGGGTACGATCCCCAATATGCGGCTTCCGTCTTTCTGGGATGGGCC
pVD218  (901) ATTTTGGAACTAA?CGGGTACGATCCCCAATATGCGGCTTCCGTCTTTCTGGGATGGGCC
pVD220  (901) ATTTTGGAACTAAACGGGTACGATCCCCAATATGCGGCTTCCGTCTTTCTGGGATGGGCC 961                                                         1020
pVD88   (961) ACGAAAAGTTCGGCAAGAGGAACACCATCTGGCTGTTTGGGCCTGCAACTACCGGGAAG
pVD210  (961) ACGAAAAGTTCGGCAAGAGGAACACCATCTGGCTGTTTGGGCCTGCAACTACCGGGAAG
pVD211  (961) ACGAAAAGTTCGGCAAGAGGAACACCATCTGGCTGTTTGGGCCTGCAACTACCGGGAAG
pVD212  (961) ACGAAAAGTTCGGCAAGAGGAACACCATCTGGCTGTTTGGGCCTGCAACTACCGGGAAG
pVD214  (961) ACGAAAAGTTCGGCAAGAGGAACACCATCTGGCTGTTTGGGCCTGCAACTACCGGGAAG
pVD215  (961) ACGAAAAGTTCGGCAAGAGGAACACCATCTGGCTGTTTGGGCCTGCAACTACCGGGAAG
pVD216  (961) ACGAAAAGTTCGGCAAGAGGAACACCATCTGGCTGTTTGGGCCTGCAACTACCGGGAAG
pVD217  (961) ACGAAAAGTTCGGCAAGAGGAACACCATCTGGCTGTTTGGGCCTGCAACTACCGGGAAG
pVD218  (961) ACGAAAAGTTCGGCAAGAGGAACACCATCTGGCTGTTTGGGCCTGCAACTACCGGGAAG
pVD220  (961) ACGAAAAGTTCGGCAAGAGGAACACCATCTGGCTGTTTGGGCCTGCAACTACCGGGAAG 1021                                                        1080
pVD88  (1021) ACCAACATCGCGGAGGCCATAGCCCACACTGTGCCCTTCTACGGGTGCGTAAACTGGACC
pVD210 (1021) ACCAACATCGCGGAGGCCATAGCCCACACTGTGCCCTTCTACGGGTGCGTAAACTGGACC
pVD211 (1021) ACCAACATCGCGGAGGCCATAGCCCACACTGTGCCCTTCTACGGGTGCGTAAACTGGACC
pVD212 (1021) ACCAACATCGCGGAGGCCATAGCCCACACTGTGCCCTTCTACGGGTGCGTAAACTGGACC
pVD214 (1021) ACCAACATCGCGGAGGCCATAGCCCACACTGTGCCCTTCTACGGGTGCGTAAACTGGACC
pVD215 (1021) ACCAACATCGCGGAGGCCATAGCCCACACTGTGCCCTTCTACGGGTGCGTAAACTGGACC
pVD216 (1021) ACCAACATCGCGGAGGCCATAGCCCACACTGTGCCCTTCTACGGGTGCGTAAACTGGACC
pVD217 (1021) ACCAACATCGCGGAGGCCATAGCCCACACTGTGCCCTTCTACGGGTGCGTAAACTGGACC
pVD218 (1021) ACCAACATCGCGGAGGCCATAGCCCACACTGTGCCCTTCTACGGGTGCGTAAACTGGACC
pVD220 (1021) ACCAACATCGCGGAGGCCATAGCCCACACTGTGCCCTTCTACGGGTGCGTAAACTGGACC 1081                                                        1140
pVD88  (1081) AATGAGAACTTTCCCTTCAACGACTGTGTCGACAAGATGGTGATCTGGTGGAGGAGGGG
pVD210 (1081) AATGAGAACTTTCCCTTCAACGACTGTGTCGACAAGATGGTGATCTGGTGGAGGAGGGG
pVD211 (1081) AATGAGAACTTTCCCTTCAACGACTGTGTCGACAAGATGGTGATCTGGTGGAGGAGGGG
pVD212 (1081) AATGAGAACTTTCCCTTCAACGACTGTGTCGACAAGATGGTGATCTGGTGGAGGAGGGG
pVD214 (1081) AATGAGAACTTTCCCTTCAACGACTGTGTCGACAAGATGGTGATCTGGTGGAGGAGGGG
pVD215 (1081) AATGAGAACTTTCCCTTCAACGACTGTGTCGACAAGATGGTGATCTGGTGGAGGAGGGG
pVD216 (1081) AATGAGAACTTTCCCTTCAACGACTGTGTCGACAAGATGGTGATCTGGTGGAGGAGGGG
pVD217 (1081) AATGAGAACTTTCCCTTCAACGACTGTGTCGACAAGATGGTGATCTGGTGGAGGAGGGG
pVD218 (1081) AATGAGAACTTTCCCTTCAACGACTGTGTCGACAAGATGGTGATCTGGTGGAGGAGGGG
pVD220 (1081) AATGAGAACTTTCCCTTCAACGACTGTGTCGACAAGATGGTGATCTGGTGGAGGAGGGG 1141                                                        1200
pVD88  (1141) AAGATGACCGCCAAGGTCGTGGAGTCGGCCAAAGCCATTCTCGGAGGAAGCAAGGTGCGC
pVD210 (1141) AAGATGACCGCCAAGGTCGTGGAGTCGGCCAAAGCCATTCTCGGAGGAAGCAAGGTGCGC
pVD211 (1141) AAGATGACCGCCAAGGTCGTGGAGTCGGCCAAAGCCATTCTCGGAGGAAGCAAGGTGCGC
pVD212 (1141) AAGATGACCGCCAAGGTCGTGGAGTCGGCCAAAGCCATTCTCGGAGGAAGCAAGGTGCGC
pVD214 (1141) AAGATGACCGCCAAGGTCGTGGAGTCGGCCAAAGCCATTCTCGGAGGAAGCAAGGTGCGC
pVD215 (1141) AAGATGACCGCCAAGGTCGTGGAGTCGGCCAAAGCCATTCTCGGAGGAAGCAAGGTGCGC
pVD216 (1141) AAGATGACCGCCAAGGTCGTGGAGTCGGCCAAAGCCATTCTCGGAGGAAGCAAGGTGCGC
pVD217 (1141) AAGATGACCGCCAAGGTCGTGGAGTCGGCCAAAGCCATTCTCGGAGGAAGCAAGGTGCGC
pVD218 (1141) AAGATGACCGCCAAGGTCGTGGAGTCGGCCAAAGCCATTCTCGGAGGAAGCAAGGTGCGC
pVD220 (1141) AAGATGACCGCCAAGGTCGTGGAGTCGGCCAAAGCCATTCTCGGAGGAAGCAAGGTGCGC
```

Fig. 16D

```
                1201                                                      1260
pVD88   (1201)  GTGGACCAGAAATGCAAGTCCTCGGCCCAGATAGACCCGACTCCCGTGATCGTCACCTCC
pVD210  (1201)  GTGGACCAGAAATGCAAGTCCTCGGCCCAGATAGACCCGACTCCCGTGATCGTCACCTCC
pVD211  (1201)  GTGGACCAGAAATGCAAGTCCTCGGCCCAGATAGACCCGACTCCCGTGATCGTCACCTCC
pVD212  (1201)  GTGGACCAGAAATGCAAGTCCTCGGCCCAGATAGACCCGACTCCCGTGATCGTCACCTCC
pVD214  (1201)  GTGGACCAGAAATGCAAGTCCTCGGCCCAGATAGACCCGACTCCCGTGATCGTCACCTCC
pVD215  (1201)  GTGGACCAGAAATGCAAGTCCTCGGCCCAGATAGACCCGACTCCCGTGATCGTCACCTCC
pVD216  (1201)  GTGGACCAGAAATGCAAGTCCTCGGCCCAGATAGACCCGACTCCCGTGATCGTCACCTCC
pVD217  (1201)  GTGGACCAGAAATGCAAGTCCTCGGCCCAGATAGACCCGACTCCCGTGATCGTCACCTCC
pVD218  (1201)  GTGGACCAGAAATGCAAGTCCTCGGCCCAGATAGACCCGACTCCCGTGATCGTCACCTCC
pVD220  (1201)  GTGGACCAGAAATGCAAGTCCTCGGCCCAGATAGACCCGACTCCCGTGATCGTCACCTCC 1261                                                      1320
pVD88   (1261)  AACACCAACATGTGCGCCGTGATTGACGGGAACTCAACGACCTTCGAACACCAGCAGCCG
pVD210  (1261)  AACACCAACATGTGCGCCGTGATTGACGGGAACTCAACGACCTTCGAACACCAGCAGCCG
pVD211  (1261)  AACACCAACATGTGCGCCGTGATTGACGGGAACTCAACGACCTTCGAACACCAGCAGCCG
pVD212  (1261)  AACACCAACATGTGCGCCGTGATTGACGGGAACTCAACGACCTTCGAACACCAGCAGCCG
pVD214  (1261)  AACACCAACATGTGCGCCGTGATTGACGGGAACTCAACGACCTTCGAACACCAGCAGCCG
pVD215  (1261)  AACACCAACATGTGCGCCGTGATTGACGGGAACTCAACGACCTTCGAACACCAGCAGCCG
pVD216  (1261)  AACACCAACATGTGCGCCGTGATTGACGGGAACTCAACGACCTTCGAACACCAGCAGCCG
pVD217  (1261)  AACACCAACATGTGCGCCGTGATTGACGGGAACTCAACGACCTTCGAACACCAGCAGCCG
pVD218  (1261)  AACACCAACATGTGCGCCGTGATTGACGGGAACTCAACGACCTTCGAACACCAGCAGCCG
pVD220  (1261)  AACACCAACATGTGCGCCGTGATTGACGGGAACTCAACGACCTTCGAACACCAGCAGCCG 1321                                                      1380
pVD88   (1321)  TTGCAAGACCGGATGTTCAAATTTGAACTCACCCGCCGTCTGGATCATGACTTTGGGAAG
pVD210  (1321)  TTGCAAGACCGGATGTTCAAATTTGAACTCACCCGCCGTCTGGATCATGACTTTGGGAAG
pVD211  (1321)  TTGCAAGACCGGATGTTCAAATTTGAACTCACCCGCCGTCTGGATCATGACTTTGGGAAG
pVD212  (1321)  TTGCAAGACCGGATGTTCAAATTTGAACTCACCCGCCGTCTGGATCATGACTTTGGGAAG
pVD214  (1321)  TTGCAAGACCGGATGTTCAAATTTGAACTCACCCGCCGTCTGGATCATGACTTTGGGAAG
pVD215  (1321)  TTGCAAGACCGGATGTTCAAATTTGAACTCACCCGCCGTCTGGATCATGACTTTGGGAAG
pVD216  (1321)  TTGCAAGACCGGATGTTCAAATTTGAACTCACCCGCCGTCTGGATCATGACTTTGGGAAG
pVD217  (1321)  TTGCAAGACCGGATGTTCAAATTTGAACTCACCCGCCGTCTGGATCATGACTTTGGGAAG
pVD218  (1321)  TTGCAAGACCGGATGTTCAAATTTGAACTCACCCGCCGTCTGGATCATGACTTTGGGAAG
pVD220  (1321)  TTGCAAGACCGGATGTTCAAATTTGAACTCACCCGCCGTCTGGATCATGACTTTGGGAAG 1381                                                      1440
pVD88   (1381)  GTCACCAAGCAGGAAGTCAAAGACTTTTTCCGGTGGGCAAAGGATCACGTGGTTGAGGTG
pVD210  (1381)  GTCACCAAGCAGGAAGTCAAAGACTTTTTCCGGTGGGCAAAGGATCACGTGGTTGAGGTG
pVD211  (1381)  GTCACCAAGCAGGAAGTCAAAGACTTTTTCCGGTGGGCAAAGGATCACGTGGTTGAGGTG
pVD212  (1381)  GTCACCAAGCAGGAAGTCAAAGACTTTTTCCGGTGGGCAAAGGATCACGTGGTTGAGGTG
pVD214  (1381)  GTCACCAAGCAGGAAGTCAAAGACTTTTTCCGGTGGGCAAAGGATCACGTGGTTGAGGTG
pVD215  (1381)  GTCACCAAGCAGGAAGTCAAAGACTTTTTCCGGTGGGCAAAGGATCACGTGGTTGAGGTG
pVD216  (1381)  GTCACCAAGCAGGAAGTCAAAGACTTTTTCCGGTGGGCAAAGGATCACGTGGTTGAGGTG
pVD217  (1381)  GTCACCAAGCAGGAAGTCAAAGACTTTTTCCGGTGGGCAAAGGATCACGTGGTTGAGGTG
pVD218  (1381)  GTCACCAAGCAGGAAGTCAAAGACTTTTTCCGGTGGGCAAAGGATCACGTGGTTGAGGTG
pVD220  (1381)  GTCACCAAGCAGGAAGTCAAAGACTTTTTCCGGTGGGCAAAGGATCACGTGGTTGAGGTG 1441                                                      1500
pVD88   (1441)  GAGCATGAATTCTACGTCAAAAAGGGTGGAGCCAAGTAA
pVD210  (1441)  GAGCATGAATTCTACGTCAAAAAGGGTGGAGCCAAGTAA
pVD211  (1441)  GAGCATGAATTCTACGTCAAAAAGGGTGGAGCCAAGTAA
pVD212  (1441)  GAGCATGAATTCTACGTCAAAAAGGGTGGAGCCAAGTAA
pVD214  (1441)  GAGCATGAATTCTACGTCAAAAAGGGTGGAGCCAAGTAA
pVD215  (1441)  GAGCATGAATTCTACGTCAAAAAGGGTGGAGCCAAGTAA
pVD216  (1441)  GAGCATGAATTCTACGTCAAAAAGGGTGGAGCCAAGTAA
pVD217  (1441)  GAGCATGAATTCTACGTCAAAAAGGGTGGAGCCAAGTAA
pVD218  (1441)  GAGCATGAATTCTACGTCAAAAAGGGTGGAGCCAAGTAA
pVD220  (1441)  GAGCATGAATTCTACGTCAAAAAGGGTGGAGCCAAGTAA
```

MUTATED REP ENCODING SEQUENCES FOR USE IN AAV PRODUCTION

CROSS-REFERENCE TO RELATED APPLICATIONS

This application is a Continuation of U.S. patent application Ser. No. 15/862,997, filed Jan. 5, 2018, which is a Continuation of U.S. patent application Ser. No. 14/952,303, filed Nov. 25, 2015, now U.S. Pat. No. 9,885,022, which is a Continuation of U.S. patent application Ser. No. 13/583, 920, filed Sep. 10, 2012, now U.S. Pat. No. 9,228,174, filed as the National Phase of International Patent Application No. PCT/NL2011/050170, filed Mar. 11, 2011, published on Sep. 15, 2011 as WO 2011/112089 A2, which claims priority to U.S. Provisional Application No. 61/312,845, filed Mar. 11, 2010. The contents of these applications are herein incorporated by reference in their entirety.

The instant application contains a Sequence Listing which has been submitted in ASCII format via EFS-WEB and is hereby incorporated by reference in its entirety. Said ASCII copy, created on Jul. 17, 2019, is named 069818-6978Sequence.txt and is 143 KB.

FIELD OF THE INVENTION

The present invention relates to nucleic acids which encode mutant Parvoviral Rep sequences. The invention also relates to nucleic acid constructs and cells, such as insect cells, which comprise the nucleic acids. The invention further relates to a method for producing a recombinant Parvoviral virion using the nucleic acids.

BACKGROUND OF THE INVENTION

Adeno-associated virus (AAV) is considered one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans, it has never been associated with any disease. In view of these advantages, recombinant adeno-associated virus (rAAV) is being evaluated in gene therapy clinical trials, inter alia, for hemophilia B, malignant melanoma, cystic fibrosis.

Host cells that sustain AAV replication in vitro are all derived from mammalian cell types. Therefore, rAAV for use in gene therapy has traditionally been produced on mammalian cell lines such as e.g. 293 cells, COS cells, HeLa cells, KB cells, and other mammalian cell lines. However, in most mammalian cell culture systems, the number of AAV particles generated per cell is of the order of $10^4$ particles (reviewed in Clark, 2002, Kidney Int. 61(Suppl. 1): 9-15). For a clinical study, more than $10^{15}$ particles of rAAV may be required. To produce this number of rAAV particles, transfection and culture with approximately $10^{11}$ cultured human 293 cells, the equivalent of 5,000 175-cm$^2$ flasks of cells, would be required, which means transfecting up to $10^{11}$ 293 cells. Therefore, large scale production of rAAV using mammalian cell culture systems to obtain material for clinical trials has already proven to be problematic, production at commercial scale may not even be feasible. Furthermore there is always the risk, that a vector for clinical use that is produced in a mammalian cell culture will be contaminated with undesirable, perhaps pathogenic, material present in the mammalian host cell.

To overcome these problems of mammalian productions systems, recently, an AAV production system has been developed using insect cells (Urabe et al., 2002, Hum. Gene Ther. 13: 1935-1943; US 20030148506 and US 20040197895). This baculovirus expression vector system (BEVS) is based on infection of insect cells with baculoviruses containing a gene to be expressed flanked by AAV ITRs, a baculovirus expressing the AAV rep gene and a baculovirus encoding the AAV cap gene leading to production of infectious rAAV particles. If desired, the AAV rep and cap genes may be present on the same baculovirus However, despite various improvements to the basic system, it is still problematic that more capsids appear to be empty rather than being loaded with the therapeutic gene of interest. There is thus still a need to overcome this limitation so as to improve large scale (commercial) production of AAV vectors in insect cells. Thus it is an object of the present invention to provide for means and methods that allow for stable and high yield (large scale) production of AAV vectors in insect cells.

BRIEF DESCRIPTION OF THE INVENTION

The invention relates to mutant Parvoviral Rep polypeptides/proteins, such as AAV Rep polypeptides/proteins, and to nucleic acids which encode those mutant polypeptides. The nucleic acids may be used in the preparation of Parvoviruses, in particular in the preparation of recombinant adeno-associated viruses (AAV). A mutant/mutated polypeptide/protein is one which is different from its corresponding wild type sequence. A mutant/mutated polypeptide/protein may typically be one which does not exist in nature.

The mutant Parvoviral Rep polypeptides typically possess one or more improved properties as compared with their corresponding wild type Rep polypeptide. Thus they may be used to prepare higher virus titres, for example, than a corresponding wild type Rep polypeptide. In addition, or alternatively, they may be able to allow the production of better quality viral particles or sustain more stable production of virus.

According to the invention, there is thus provided a nucleic acid comprising a nucleotide sequence encoding a Parvoviral Rep protein, wherein a nuclear localization signal (NLS) in said Parvoviral Rep protein is mutated as compared with a corresponding wild type sequence.

The invention also provides a nucleic acid comprising a nucleotide sequence encoding a Parvoviral Rep protein, wherein the zinc finger domain in said Parvoviral Rep protein is mutated as compared with a corresponding wild type sequence.

Further, the invention provides a nucleic acid according to any one of the preceding claims which encodes a Parvoviral Rep protein, wherein the codon encoding the amino acid at position 493 or 571 is substituted with a stop codon, said amino acid position being defined with reference to SEQ ID NO: 1.

In addition, the invention provides:
a nucleic acid comprising a nucleotide sequence encoding a Parvoviral Rep protein, wherein an amino acid at position 43, 57, 79, 97, 120, 179, 305, 484, 493 or 571 of the said Parvoviral Rep protein is mutated in comparison to a corresponding wild type sequence, said amino acid position being defined with reference to SEQ ID NO: 2;
a nucleic acid comprising the nucleotide sequence set out in any one of SEQ ID NOs: 5, 7, 9, 11, 13, 15, 17, 19 or 21;

a nucleic acid comprising a nucleotide sequence encoding the Rep protein as set out in any one of SEQ ID NOs: 6, 8, 10, 12, 14, 16, 18, 20 or 22;

a nucleic acid comprising two or more nucleotide sequences which encode a Parvoviral Rep protein, one or more of which is a nucleic acid as described herein;

a Parvoviral Rep protein as defined above or as encoded by a nucleic acid as defined above;

a nucleic acid construct comprising a nucleic acid as described herein, wherein the said nucleic acid is operably linked to an expression control sequence for expression in an insect cell;

an insect cell comprising a nucleic acid or a nucleic acid construct as described herein; and a method for the production of a recombinant Parvoviral virion in an insect cell, the virion comprising a nucleic acid of the invention operably linked to an expression control sequence for expression in an insect cell, which method comprises:

(i) culturing an insect cell as defined above,
wherein the insect cell further comprises: a nucleic acid comprising at least one Parvoviral inverted terminal repeat (ITR) nucleotide sequence; and a nucleic acid sequence comprising a nucleotide sequence encoding Parvoviral capsid protein coding sequence operably linked to expression control sequences for expression in an insect cell, under conditions such that a recombinant parvoviral virion is produced; and, (ii) recovering the recombinant parvoviral virion.

BRIEF DESCRIPTION OF THE DRAWINGS

FIGS. 4A, 4B, and 4C show the restriction analysis of the two different pVD142-Rep-EP libraries A) PstI-EagI restriction fragments of pVD142. B) PstI-EagI restriction fragments of pVD143.C) An agarose gel showing restriction fragments of pVD142 (1), pVD143 (2), pVD142-Rep-EP1 (3) and pVD142-Rep-EP3 (4) digested with PstI-EagI. M, Smartladder (Eurogentec). The lower panel is overexposed to detect the 175 bp fragment.

Figure 16F:
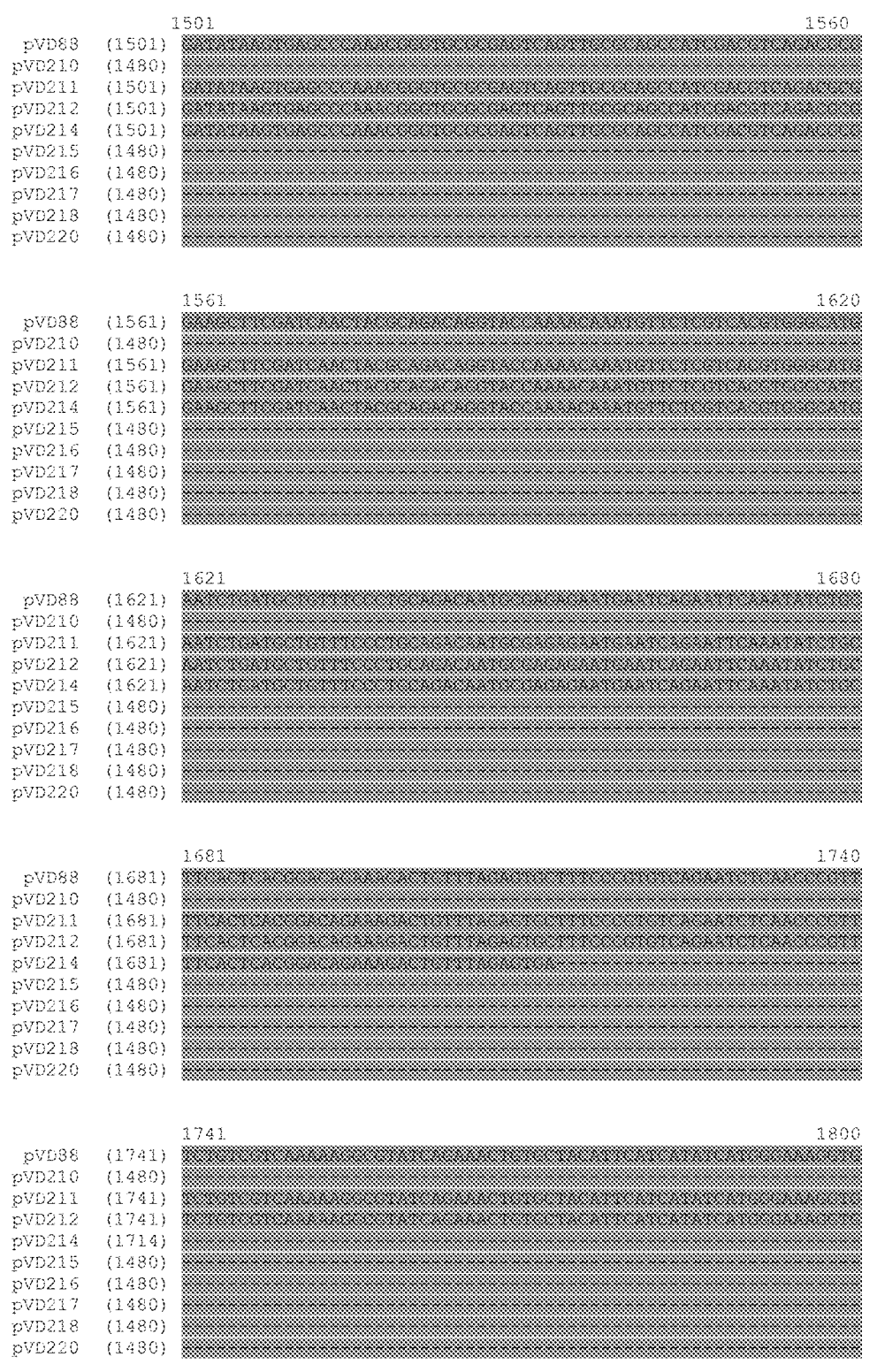

FIGS. 16A, 16B, 16C, 16D, 16E, 16F, and 16G show a sequence comparison of VD88 (SEQ ID NO:3), VD210 (SEQ ID NO:5), VD211 (SEQ ID NO:7), VD212 (SEQ ID NO:9), VD214 (SEQ ID NO:11), VD215 (SEQ ID NO:13), VD216 VD217 (SEQ ID NO:17), VD218 (SEQ ID NO:19) and VD220 (SEQ ID NO:21).

BRIEF DESCRIPTION OF THE SEQUENCE LISTING

Figure 1:
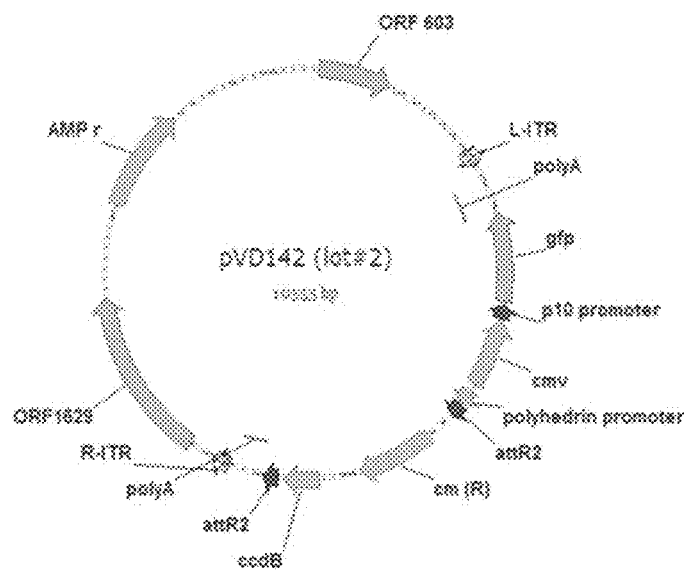
FIG. 1 shows a schematic representation of pVD142(lot #2).

SEQ ID NO: 1 sets out the full length nucleotide sequence of Rep78 from AAV2.
SEQ ID NO: 2 sets out the full length amino acid sequence of Rep78 from AAV2.
SEQ ID NO: 3 sets out the nucleotide sequence of VD88.
SEQ ID NO: 4 sets out the amino acid sequence of VD88.
SEQ ID NO: 5 sets out the nucleotide sequence of VD210.
SEQ ID NO: 6 sets out the amino acid sequence of VD210.
SEQ ID NO: 7 sets out the nucleotide sequence of VD211.
SEQ ID NO: 8 sets out the amino acid sequence of VD211.
SEQ ID NO: 9 sets out the nucleotide sequence of VD212.
SEQ ID NO: 10 sets out the amino acid sequence of VD212.
SEQ ID NO: 11 sets out the nucleotide sequence of VD214.
SEQ ID NO: 12 sets out the amino acid sequence of VD214.
SEQ ID NO: 13 sets out the nucleotide sequence of VD215.
SEQ ID NO: 14 sets out the amino acid sequence of VD215.
SEQ ID NO: 15 sets out the nucleotide sequence of VD216.
SEQ ID NO: 16 sets out the amino acid sequence of VD216.
SEQ ID NO: 17 sets out the nucleotide sequence of VD217.
SEQ ID NO: 18 sets out the amino acid sequence of VD217.
SEQ ID NO: 19 sets out the nucleotide sequence of VD218.
SEQ ID NO: 20 sets out the amino acid sequence of VD218.
SEQ ID NO: 21 sets out the nucleotide sequence of VD220.
SEQ ID NO: 22 sets out the amino acid sequence of VD220.

DETAILED DESCRIPTION OF THE INVENTION

The present invention concerns animal parvoviruses, in particular dependoviruses such as infectious human or simian AAV, and the components thereof (e.g., an animal parvovirus genome). In particular, the invention relates to nucleic acids which encode mutant Rep polypeptides/proteins.

Parvoviruses may be used as vectors for introduction and/or expression of nucleic acids in mammalian cells. Thus, the invention concerns improvements to productivity and/or quality of such parvoviral vectors when produced in insect cells.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture.

The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein largely by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promotor, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The invention relates to a nucleic acid comprising a nucleotide sequence encoding a mutant Parvoviral Rep protein. That is to say, a nucleic acid of the invention encodes a non-wild type Parvoviral Rep protein. Typically, a nucleic acid of the invention encodes a non-wild type AAV Rep protein.

As set out above, the present invention provides a nucleic acid encoding the variant polypeptides of the invention. The invention also relates to an isolated polynucleotide encoding at least one functional domain of a polypeptide variant of the invention. Typically, such a domain will comprise one or more of the mutations described herein.

In one embodiment of the invention, the nucleic acid sequence according to the invention encodes a polypeptide, wherein the polypeptide is a variant comprising an amino acid sequence that has a mutation, for example one or more truncation(s), and/or at least one substitution, deletion and/or insertion of an amino acid as compared to a corresponding wild type Rep protein. Typically, mutations in the invention are substitutions, i.e. one amino acid is replaced with an amino acid that does not typically appear at the relevant position in the corresponding wild type sequence. Such a polypeptide will, however, typically comprise one or more of the mutations, in particular substitutions, described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein. For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well know to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent asparaginase. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" may be a nucleic acid fragment that is not naturally occurring as a fragment and would not be found in the natural state.

As used herein, the terms "polynucleotide" or "nucleic acid (molecule)" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

A nucleotide sequence encoding a mutant Parvoviral Rep protein, is herein understood as a nucleotide sequence encoding a non-structural Rep protein. A nucleic acid sequence of the invention may comprise sequences encoding more than one Rep protein (at least one of which is a mutant Rep protein), in particular those that are required and sufficient for parvoviral vector production in insect cells such the Rep78, Rep52, Rep 68 or Rep 40 proteins.

The Parvovirus nucleic acid of the invention preferably is from a dependovirus, more preferably from a human or simian adeno-associated virus (AAV) and most preferably from an AAV which normally infects humans (e.g., serotypes 1, 2, 3A, 3B, 4, 5, 6, 7, 8 or 9) or primates (e.g., serotypes 1 and 4).

An example of a nucleotide sequence encoding animal parvoviruses Rep proteins is given in SEQ ID NO: 1, which depicts the wild type sequence encoding the Rep 78 and Rep 52 proteins from AAV2. The full length coding sequence encodes the Rep 78 protein. It is understood that the exact molecular weights of the Rep78 and Rep52 proteins, as well as the exact positions of the translation initiation codons may differ between different parvoviruses. However, the skilled person will know how to identify the corresponding position(s) in a nucleotide sequence from parvoviruses other than AAV2, for example by carrying out an alignment.

A nucleotide sequence encoding an animal parvovirus Rep protein may thus also be defined as a nucleotide sequence:

a) that encodes a polypeptide comprising an amino acid sequence that has at least 50, 60, 70, 80, 88, 89, 90, 95, 97, 98, or 99% sequence identity with the amino acid sequence of SEQ ID NO. 2;

b) that has at least 50, 60, 70, 80, 81, 82, 85, 90, 95, 97, 98, or 99% sequence identity with the nucleotide sequence of positions 11-1876 of SEQ ID NO: 1;

c) the complementary strand of which hybridises to a nucleic acid molecule sequence of (a) or (b);

d) nucleotide sequences the sequence of which differs from the sequence of a nucleic acid molecule of (c) due to the degeneracy of the genetic code.

A nucleic acid of the invention may encode more than one animal Parvoviruse Rep protein and may encode the Rep proteins that are required and sufficient for parvoviral vector production in insect cells.

A nucleic acid of the invention may comprise a nucleotide sequence encoding a Parvoviral Rep protein, wherein a nuclear localization signal (NLS) in said Parvoviral Rep protein is mutated with respect to the wild type sequence.

In the wild type AAV2 Rep78 protein, there are three putative NLS sequences located at positions 484-491, 492-494 and 506-509 of SEQ ID NO: 2. One, two or all three of said sites may be mutated, in particular carry one or more substituted amino acids, in a mutant Parvoviral Rep protein encoded by a nucleic acid of the invention. These mutations typically reduce the ability of the NLS to act as an NLS.

A nucleic acid of the invention may encode a mutant Parvoviral Rep protein, wherein an NLS (or two or more NLSs) is at least partially truncated and/or deleted.

A nucleic acid of the invention may be truncated such that the encoded Rep protein is truncated in comparison to the corresponding wild type sequence such that said truncation results in mutation of an NLS (or two or more NLSs) encoded by the nucleic acid. The truncation may result in partial or complete deletion of one or more NLS sequences.

According to the invention, there is also provided a nucleic acid comprising a nucleotide sequence encoding a Parvoviral Rep protein, wherein the zinc finger domain in said Parvoviral Rep protein is mutated with respect to the corresponding wild type sequence.

Herein, reference to a corresponding wild type sequence indicates the wild type sequence from which a variant nucleic acid of the invention is derived, for example the wild type sequence of AAV2 Rep78 where the variant is a variant of that sequence.

With reference to the wild type AAV2 Rep78 protein (SEQ ID NO: 2), the zinc finger sequence is located at from about amino acid 526 to about amino acid 621.

A nucleic acid according of the invention may encode a Rep protein in which the zinc finger domain is at least partially mutated, such as carrying one or more substitutions or is truncated and/or deleted.

Accordingly, a nucleic acid of the invention may encode a Rep protein which is truncated with respect to the corresponding wild type sequence such that said truncation results in mutation of the zinc finger domain encoded by the nucleic acid.

These mutations will typically result in the zinc finger domain having a reduced ability to operate as a zinc finger domain.

The invention provides, in particular, a nucleic acid according to any one of the preceding claims which encodes a Parvoviral Rep protein, wherein the codon encoding the amino acid at position 493 or 571 is substituted with a stop codon, said amino acid position being defined with reference to SEQ ID NO: 2 (wild type Rep78 from AAV2). That is to say, the nucleic acid is truncated at one of the two positions mentioned.

A nucleic acid of the invention may comprise mutations both to the sequences encoding the zinc finger domain and to one or more sequence encoding an NLS. That is to say, these types of mutations may be combined in a single nucleic acid of the invention.

Further provided by the invention is a nucleic acid comprising a nucleotide sequence encoding a Parvoviral Rep protein, wherein an amino acid at position 43, 57, 79, 97, 120, 179, 305, 484, 493 or 571 of the said Parvoviral Rep protein is mutated with respect to the wild type sequence, said amino acid position being defined with reference to SEQ ID NO: 2. Typically, these mutations will be substitutions, i.e. the amino acid which appears at a position in the wild type is replaced with an amino acid that does not typically appear at that position.

A nucleic acid of the invention may be defined by a combination of two or more of the above-mentioned mutations.

Such a nucleic acid of the invention may encode a Rep polypeptide, wherein amino acids at positions:

79 and 120;
57, 97 and 179;
57, 97, 179 and 484;
43, 79 and 120;
79 and 120; or
79, 120 and 305.

are mutated with respect to the corresponding wild type sequence, said amino acid positions being defined with reference to SEQ ID NO: 2.

Any one of these combinations may further be combined with the mutations at positions 493 or 571, said amino acid positions being defined with reference to SEQ ID NO: 2.

The following two Tables set out combinations of mutations which may be used to define a nucleic acid of the invention. The positions set out in the Tables are defined with reference to the Rep78 sequence from AAV2 (SEQ ID NO: 2). Clearly, at the nucleotide sequence level, any mutation may be used which effects the amino acid mutation set out in Table 2. Table 1 gives specific, non-limiting examples of how that may be achieved.

TABLE 1

Nucleotide mutations in Rep baculovirus constructs

| Baculovirus | Rep sequence (bp) | Nucleotide mutations |
|---|---|---|
| Bac. VD210 | 1476 | |
| Bac. VD211 | 1866 | nt236(T > A)  nt358(A > T) |
| Bac. VD212 | 1866 | nt170(A > G)  nt289(A > C)  nt535(T > C)  nt642(G > T) |
| Bac. VD214 | 1720 | nt170(A > G)  nt289(A > C)  nt535(T > C)  nt642(G > T)  nt894(T > A)  nt1450(T > C) |
| Bac. VD215 | 1476 | nt127(A > G)  nt236(T > A)  nt358(A > T)  nt633(T > C) |
| Bac. VD216 | 1476 | nt127(A > G)  nt236(T > A)  nt358(A > T) |
| Bac. VD217 | 1476 | nt236(T > A)  nt358(A > T) |
| Bac. VD218 | 1476 | nt236(T > A)  nt358(A > T)  nt914(A > G) |
| Bac. VD219 | 1476 | nt236(T > A)  nt358(A > T) |
| Bac. VD220 | 1476 | nt170(A > G)  nt289(A > C)  nt535(T > C)  nt642(G > T) |

TABLE 2

Amino acids mutations in Rep baculovirus constructs

| Baculovirus | Rep sequence (bp) | Amino acids mutations | | | | | |
|---|---|---|---|---|---|---|---|
| Bac. VD210 | 1476 | | | | | | 493K –> stop |
| Bac. VD211 | 1866 | | 79F –> Y | 120I –> F | | | |
| Bac. VD212 | 1866 | 57E –> G | 97T –> P | 179C –> R | | | |
| Bac. VD214 | 1720 | 57E –> G | 97T –> P | 179C –> R | 484F –> L | | 571C –> stop |
| Bac. VD215 | 1476 | 43M –> V | 79F –> Y | 120I –> F | | | 493K –> stop |
| Bac. VD216 | 1476 | 43M –> V | 79F –> Y | 120I –> F | | | 493K –> stop |
| Bac. VD217 | 1476 | | 79F –> Y | 120I –> F | | | 493K –> stop |
| Bac. VD218 | 1476 | | 79F –> Y | 120I –> F | | 305N –> S | 493K –> stop |
| Bac. VD219 | 1476 | | 79F –> Y | 120I –> F | | | 493K –> stop |
| Bac. VD220 | 1476 | 57E –> G | 97T –> P | 179C –> R | | | |

A nucleic acid as described above may encode a Rep protein having at least about 50%, at least about 60%, at least about 70%, at least about 80%, at least about 90%, at least about 95%, at least about 98% or at least about 99% or higher sequence similarity to a corresponding wild type Rep protein sequence, i.e. to the wild type sequence from which it is derived. That is to say, a nucleic acid of the invention may have additional differences from a wild type sequence other than those described above.

A nucleic acid of the invention will typically display improved properties as compared to its corresponding wild type sequence. For example, it may lead to improved Parvoviral product (i.e. higher virus titre) when used to produce recombinant Parvovirus, such as rAAV, as compared to the corresponding wild type. It may lead to a better quality product in terms of having fewer empty virions in comparison to full virions (i.e. virions filled with vector) or to put it another way, a lower (i.e. improved) total/full particle ratio. It may also lead to the accumulation of less residual DNA than a corresponding wild type sequence.

A nucleic acid of the invention may be one which produces a measurable improvement in any such relevant property, for example one of those mentioned above, in comparison to the corresponding wild type sequence. Preferred nucleic acids are those which show an improvement as compared to the wild type in any relevant property of at least about 10%, at least about 25%, at least about 50%, at least about 100%, at least about 200%, at least about 500% or at least about 1000% or more.

The positions in the variant/mutant sequences of the invention set out above are defined with reference to SEQ ID NO: 2 which is the AAV2 Rep78 sequence. A corresponding position in a different Parvoviral Rep sequence, say an AAV5 sequence, may be identified by aligning the two sequences, typically in an optimal way. That would allow the corresponding positions in a wild type sequence (other than that of SEQ ID NO: 2) to be identified and thus the positions at which mutations (such as substitutions) may be incorporated to derive a nucleic acid of the invention.

The terms "percent identity" or "homology" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues (or nucleotide residues).

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleotide sequences referred to herein may further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

Nucleotide sequences encoding parvoviral Rep proteins of the invention may also be defined by their capability to hybridise with the nucleotide sequence of SEQ ID NO.1, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A nucleic acid as described herein may encode a parvoviral Rep protein which is an adeno-associated virus (AAV) Rep protein. A nucleic acid of the invention may encode a Rep78, a Rep68, a Rep 52 or a Rep 40 protein. A nucleic acid of the invention may be based on an AAV1, AAV2, AAV3, AAV4, AAV5, AAV6, AAV7, AAV8 or AAV9 or any other AAV serotype.

More specifically, a nucleic acid of the invention may comprise a nucleotide sequence as set out in any one of SEQ ID NOs: 5, 7, 9, 11, 13, 15, 17, 19 or 21;

A nucleic acid of the invention may comprise a nucleotide sequence encoding the Rep protein as set out in any one of SEQ ID NOs: 6, 8, 10, 12, 14, 16, 18, 20, or 22.

A nucleic acid comprising two or more nucleotide sequences which encode Rep a protein, one or more of which nucleic acids is as according to any one of the preceding claims.

The invention also provides a Parvoviral Rep protein encoded by a nucleic acid of the invention as defined above.

A nucleic acid of the invention sequence may comprise one open reading frame comprising nucleotide sequences encoding more than one parvoviral Rep protein, wherein the initiation codon for translation of the parvoviral Rep78 protein is a suboptimal initiation codon. The suboptimal initiation codon preferably is an initiation codon that effects partial exon skipping. Partial exon skipping is herein understood to mean that at least part of the ribosomes do not initiate translation at the suboptimal initiation codon of the Rep78 protein but at an initiation codon further downstream, whereby preferably the initiation codon further downstream is the initiation codon of the Rep52 protein. The suboptimal initiation codon preferably effects partial exon skipping upon expression of the nucleotide sequence in an insect cell. Preferably, the suboptimal initiation codon effects partial exon skipping in an insect cell so as to produce in the insect cell a molar ratio of Rep78 to Rep52 in the range of 1:10 to 10:1, 1:5 to 5:1, or 1:3 to 3:1, preferably at about 20-40 hours post infection, more preferably at about 30-40 hours post infection, using a baculovirus expression. The molar ration of the Rep78 and Rep52 may be determined by means of Western blotting as described in Example 2.1.5, preferably using a monoclonal antibody that recognizes a common epitope of both Rep78 and Rep52, or using the antibody described in Example 2.1.5.

The term "suboptimal initiation codon" herein not only refers to the tri-nucleotide initiation codon itself but also to its context. Thus, a suboptimal initiation codon may consist of an "optimal" ATG codon in a suboptimal context, e.g. a non-Kozak context. However, more preferred are suboptimal initiation codons wherein the tri-nucleotide intitiation codon itself is suboptimal, i.e. is not ATG. Suboptimal is herein understood to mean that the codon is less efficient in the inititiation of translation in an otherwise identical context as compared to the normal ATG codon. Preferably, the efficiency of suboptimal codon is less than 90, 80, 60, 40 or 20% of the efficiency of the normal ATG codon in an otherwise identical context. Methods for comparing the relative efficiency of inititiation of translation are known per se to the skilled person. Preferred suboptimal initiation codons may be selected from ACG, TTG, CTG, and GTG. More preferred is ACG.

Elimination of possible false translation initiation sites in the mutant Rep protein encoding sequences of the invention, other than the Rep78 and Rep52 translation initiation sites, of other parvoviruses will be well understood by an artisan of skill in the art, as will be the elimination of putative splice sites that may be recognised in insect cells. The various modifications of the wild-type parvoviral sequences for proper expression in insect cells is achieved by application of well-known genetic engineering techniques such as described e.g. in Sambrook and Russell (2001) "Molecular Cloning: A Laboratory Manual (3rd edition), Cold Spring Harbor Laboratory, Cold Spring Harbor Laboratory Press, New York. Various further modifications of Rep protein coding regions are known to the skilled artisan which could increase yield of Rep protein. These modifications are within the scope of the present invention.

A nucleic acid of the invention may be comprised within a nucleic acid construct. That is to say, the invention provides a nucleic acid construct comprising a nucleotide sequence as described above, wherein the nucleotide sequence is operably linked to expression control sequences for expression in a host cell, for example an insect cell.

These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of the nucleotide sequence of the invention encoding of the parvoviral Rep proteins is e.g. the polyhedron promoter. However, other promoters that are active in insect cells are known in the art, e.g. the p10, p35, IE-1 or ΔIE-1 promoters and further promoters described in the above references.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

In the event that expression of a Rep protein in an insect cell is required, in a nucleic acid construct of the invention, the nucleotide sequence may be operably linked to a polyhedron promoter, for example.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue
☐ ☐☐e in specific types of tissues or cells.

A further preferred nucleotide sequence of the invention comprises an expression control sequence that comprising a nine nucleotide sequence as described at page 9, lines 14 to 21 of WO2007/148971 or a nucleotide sequence substantially homologous thereto, upstream of the initiation codon of the nucleotide sequence encoding the parvoviral Rep78 protein. A sequence with substantial identity to the nucleotide sequence of SEQ. ID NO: 7 and that will help increase expression of the parvoviral Rep78 protein is e.g. a sequence which has at least 60%, 70%, 80% or 90% identity to the nine nucleotide sequence disclosed in WO2007/148971.

A nucleic acid construct according to the invention may be any suitable vector, for example an insect cell-compatible vector, preferably a baculoviral vector. Thus, preferably the nucleic acid construct for expression of a parvoviral Rep protein in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

The invention further provides an insect cell comprising a nucleic acid or a nucleic acid construct as described herein. A further preferred insect cell may comprise a nucleotide sequence or nucleic acid construct as defined above encoding two or more mutant parvoviral Rep proteins.

Such an insect cell may comprise no more than one type of nucleotide sequence comprising a single open reading frame encoding a parvoviral Rep protein. Preferably the single open reading frame encodes one or more of the parvoviral Rep proteins, more preferably the open reading frame encodes all of the parvoviral Rep proteins, most preferably the open reading frame encodes the full-length Rep 78 protein from which preferably at least both Rep 52 and Rep 78 proteins may be expressed in the insect cell. One or both of said proteins may be encoded by a nucleic acid of the invention.

It is understood herein that the insect cell may comprise more than one copy of the single type of nucleotide sequence, e.g. in a multicopy episomal vector, but that these are multiple copies of essentially one and the same nucleic acid molecule, or at least nucleic acid molecules that encode one and the same Rep amino acid sequence, e.g. nucleic acid molecules that only differ between each other due to the degeneracy of the genetic code. The presence of only a single type of nucleic acid molecule encoding the parvoviral Rep proteins avoids recombination between homologous sequences as may be present in different types of vectors comprising Rep sequences, which may give rise to defective Rep expression constructs that affect (stability of) parvoviral production levels in insect cells. Preferably, in the insect cell, the nucleotide sequence comprising the single open reading frame encoding one or more parvoviral Rep proteins is part of a nucleic acid construct wherein the nucleotide sequence is operably linked to expression control sequences for expression in an insect cell.

Any insect cell which allows for replication of a recombinant parvoviral (rAAV) vector and which can be maintained in culture can be used in accordance with the present invention. For example, the cell line used can be from *Spodoptera frugiperda*, *drosophila* cell lines, or mosquito cell lines, e.g., *Aedes albopictus* derived cell lines. Preferred insect cells or cell lines are cells from the insect species which are susceptible to baculovirus infection, including e.g. Se301, SeIZD2109, SeUCR1, Sf9, Sf900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

An insect cell of the invention may further comprise:
a) a nucleic acid comprising at least one parvoviral inverted terminal repeat (ITR) nucleotide sequence; and;
b) a nucleic acid sequence comprising a nucleotide sequence encoding parvoviral capsid protein coding sequence operably linked to expression control sequences for expression in an insect cell.

In an insect cell of the invention, the nucleic acids in the cell may be comprised within one or more insect cell-compatible vectors, preferably baculoviral vectors.

In an insect cell of the invention, the nucleic acid comprising at least one parvoviral inverted terminal repeat (ITR) nucleotide sequence may further comprise at least one nucleotide sequence encoding a gene product of interest.

The nucleic acid present in the insect cells of the invention, i.e. the sequence comprising at least one parvoviral (AAV) ITR, further comprises at least one nucleotide sequence encoding a gene product of interest, whereby preferably the at least one nucleotide sequence encoding a gene product of interest becomes incorporated into the genome of a recombinant parvoviral (rAAV) vector produced in the insect cell. Preferably, at least one nucleotide sequence encoding a gene product of interest is a sequence suitable for expression in a mammalian cell. Preferably, the nucleotide sequence comprises two parvoviral (AAV) ITR nucleotide sequences and wherein the at least one nucleotide sequence encoding a gene product of interest is located between the two parvoviral (AAV) ITR nucleotide sequences. Preferably, the nucleotide sequence encoding a gene product of interest (for expression in the mammalian cell) will be incorporated into the recombinant parvoviral (rAAV) vector produced in the insect cell if it is located between two regular ITRs, or is located on either side of an ITR engineered with two D regions.

The nucleic acid defined herein above may thus comprise a nucleotide sequence encoding at least one "gene product of interest" for expression in a mammalian cell, located such that it will be incorporated into an recombinant parvoviral (rAAV) vector replicated in the insect cell. Any nucleotide sequence can be incorporated for later expression in a mammalian cell transfected with the recombinant parvoviral (rAAV) vector produced in accordance with the present invention. The nucleotide sequence may e.g. encode a protein it may express an RNAi agent, i.e. an RNA molecule that is capable of RNA interference such as e.g. a shRNA (short hairpinRNA) or an siRNA (short interfering RNA). "siRNA" means a small interfering RNA that is a short-length double-stranded RNA that are not toxic in mammalian cells (Elbashir et al., 2001, Nature 411: 494-98; Caplen et al., 2001, Proc. Natl. Acad. Sci. USA 98: 9742-47). In a preferred embodiment, such a nucleotide sequence may comprise two nucleotide sequences and each encodes one gene product of interest for expression in a mammalian cell. Each of the two nucleotide sequences encoding a product of interest is located such that it will be incorporated into a recombinant parvoviral (rAAV) vector replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), and cytokines or interleukins like e.g. IL-10.

Alternatively, or in addition as a second gene product, a nucleic acid may comprise a nucleotide sequence encoding a polypeptide that serves as a marker protein to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York. Furthermore, a nucleic acid used in the invention may comprise a nucleotide sequence encoding a polypeptide that may serve as a fail-safe mechanism that allows curing of a subject from cells transduced with the recombinant parvoviral (rAAV) vector of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob. Agents Chemother. 31: 844-849).

In another embodiment one of the gene products of interest can be an AAV protein. In particular, a Rep protein, such as Rep78 or Rep68, or a functional fragment thereof. A nucleotide sequence encoding a Rep78 and/or a Rep68, if present on the genome of a recombinant parvoviral (rAAV) vector of the invention and expressed in a mammalian cell transduced with the vector, allows for integration of the recombinant parvoviral (rAAV) vector into the genome of the transduced mammalian cell. Expression of Rep78 and/or Rep68 in an rAAV-transduced or infected mammalian cell can provide an advantage for certain uses of the recombinant parvoviral (rAAV) vector, by allowing long term or permanent expression of any other gene product of interest introduced in the cell by the vector.

In the recombinant parvoviral (rAAV) vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Contitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an al-antitrypsin promoter, a thyroid hormone-binding globulin promoter, an albumin promoter, LPS (thyroxine-binding globlin) promoter, HCR-ApoCII hybrid promoter, HCR-hAAT hybrid promoter and an apolipoprotein E promoter. Other examples include the E2F promoter for tumor-selective, and, in particular, neurological cell tumor-selective expression (Parr et al., 1997, Nat. Med. 3:1145-9) or the IL-2 promoter for use in mononuclear blood cells (Hagenbaugh et al., 1997, J Exp Med; 185: 2101-10).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR).

Nicking of single-stranded DNA occurs at the junction between the A and D regions. It is the region where new DNA synthesis initiates. The D region normally sits to one side of the palindrome and provides directionality to the nucleic acid replication step. An parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs may be used. Most preferably, two ITR sequences are used. A preferred parvoviral ITR is an AAV ITR. For safety reasons it may be desirable to construct a recombinant parvoviral (rAAV) vector that is unable to further propagate after initial introduction into a cell. Such a safety mechanism for limiting undesirable vector propagation in a recipient may be provided by using rAAV with a chimeric ITR as described in US2003148506.

The number of nucleic acid constructs employed in the insect cell for the production of the recombinant parvoviral (rAAV) vector is not limiting in the invention. For example, one, two, three, four, five, or more separate constructs can be employed to produce rAAV in insect cells in accordance with the methods of the present invention. If five constructs are employed, one construct encodes AAV VP 1, another construct encodes AAV VP2, yet another construct encodes AAV VP3, still yet another construct encodes the Rep protein as defined above and a final construct comprises at least one AAV ITR. If fewer than five constructs are used, the constructs can comprise various combinations of the at least one AAV ITR and the VP1, VP2, VP3, and the Rep protein coding sequences. Preferably, two constructs or three constructs are used, with two constructs being more preferred as described above. If two constructs are used, preferably the insect cell comprises: (a) a nucleic acid construct for expression of the Rep proteins as defined above, which construct further comprises nucleotide sequences as defined in (b) above (comprising parvoviral Cap protein coding sequences operably linked to at least one expression control sequence for expression in an insect cell; see also below); and (c) a nucleic acid construct comprising the nucleotide sequence as defined in (a) above (comprising at least one parvoviral/AAV ITR nucleotide sequence). If three constructs are used, preferably the same configuration as used for two constructs is used except that separate constructs are used for expression of the capsid proteins and for expression of the Rep proteins. The sequences on each construct can be in any order relative to each other. For example, if one construct comprises ITRs and an ORF comprising nucleotide sequences encoding VP capsid proteins, the VP ORF can be located on the construct such that, upon replication of the DNA between ITR sequences, the VP ORF is replicated or not replicated. For another example, the Rep coding sequences and/or the ORF comprising nucleotide sequences encoding VP capsid proteins can be in any order on a construct. In is understood that also the further nucleic acid construct(s) preferably are an insect cell-compatible vectors, preferably a baculoviral vectors as described above. Alternatively, in the insect cell of the invention, one or more of the nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

In the invention, the nucleotide sequence comprising parvoviral capsid (Cap) protein coding sequences is herein understood to comprises sequences encoding each of the three parvoviral capsid proteins, VP1, -2 and -3. The nucleotide sequence comprising the capsid protein coding sequences may be present in various forms. E.g. separate coding sequences for each of the capsid proteins VP1, -2 and -3 may used, whereby each coding sequence is operably linked to expression control sequences for expression in an insect cell. More preferably, however, such a nucleotide sequence comprises a single open reading frame encoding all three of the animal parvoviral (AAV) VP1, VP2, and VP3 capsid proteins, wherein the initiation codon for translation of the VP1 capsid protein is a suboptimal initiation codon that is not ATG as e.g. described by Urabe et al. (2002, supra). A suboptimal initiation codon for the VP1 capsid protein may be as defined above for the Rep78 protein. More preferred suboptimal initiation codons for the VP1 capsid protein may be selected from ACG, TTG, CTG and GTG, of which CTG and GTG are most preferred. A preferred nucleotide sequence for the expression of the capsid proteins further comprises an expression control sequence comprising a nine nucleotide sequence as disclosed at page 9, lines 14 to 21 of WO2007/148971 or a nucleotide sequence substantially homologous thereto, upstream of the initiation codon of the nucleotide sequence encoding the VP1 capsid protein. A sequence with substantial identity to the nucleotide sequence of disclosed in WO2007/148971 and that will help increase expression of VP1 is e.g. a sequence which has at least 60%, 70%, 80% or 90% identity to the said nine nucleotide. A further preferred third nucleotide sequence for expression of the capsid proteins further preferably comprises at least one modification of the nucleotide sequence encoding the VP1 capsid protein selected from among a C at nucleotide position 12, an A at nucleotide position 21, and a C at nucleotide position 24 (with reference to position 1 being the first nucleotide of the translation initiation codon; see the VP capsid sequence as disclosed in WO2007/148971. Elimination of possible false initiation codons for translation of VP1 of other serotypes will be well understood by an artisan of skill in the art, as will be the elimination of putative splice sites that may be recognised in insect cells. Various further modifications of VP coding regions are known to the skilled artisan which could either increase yield of VP and virion or have other desired effects, such as altered tropism or reduce antigenicity of the virion. These modifications are within the scope of the present invention. Preferably the nucleotide sequence of the invention encoding the parvoviral capsid proteins is operably linked to expression control sequences for expression in an insect cell, which will at least include a promoter that is active in insect cells. Such control sequences and further techniques and materials (e.g. vectors) for expressing parvoviral capsid proteins in insect host cells are already described above for the Rep proteins.

AAV is able to infect a number of mammalian cells. See, e.g., Tratschin et al. (1985, Mol. Cell Biol. 5:3251-3260) and Grimm et al. (1999, Hum. Gene Ther. 10:2445-2450). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al. (2000, Proc. Natl. Acad. Sci. USA, 97:3428-3432), who discuss differences among AAV2, AAV4, and AAV5 with respect to mammalian CNS cell tropism and transduction efficiency.

AAV sequences that may be used in the present invention for the production of recombinant AAV vectors in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are preferred source of AAV nucleotide sequences for use in the context of the present invention. Preferably the AAV ITR sequences for use in the context of the present invention are derived from AAV1, AAV2, and/or AAV4. Likewise, the Rep (Rep78 and Rep52) coding sequences are preferably derived from AAV1, AAV2, and/or AAV4. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of a serotype (e.g., AAV3) and the Rep and/or ITR sequences of another AAV serotype (e.g., AAV2). Such pseudotyped rAAV particles are a part of the present invention.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 vectors in the insect cell.

In an insect cell of the invention, the Parvovirus may be adeno-associated virus (AAV).

The invention also provides a method for producing a recombinant parvoviral virion in an insect cell, the virion comprising a nucleotide sequence the nucleic acid comprising at least one parvoviral inverted terminal repeat (ITR) nucleotide sequence and, optionally, at least one nucleotide sequence encoding a gene product of interest, which method comprises:
  a) culturing an insect cell as defined herein which comprises at least one parvoviral inverted terminal repeat (ITR) nucleotide sequence and, optionally, at least one nucleotide sequence encoding a gene product of interest under conditions such that a recombinant parvoviral virion is produced; and,
  b) recovering the recombinant parvoviral virion.

A "recombinant parvoviral virion or AAV vector" (or "rAAV virion or vector") herein refers to a vector comprising one or more polynucleotide sequences of interest, genes of interest or "transgenes" that are flanked by parvoviral or AAV inverted terminal repeat sequences (ITRs). Such rAAV vectors can be replicated and packaged into infectious viral particles when present in an insect host cell that is expressing AAV rep and cap gene products (i.e. AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

In another aspect the invention thus relates to a method for producing a recombinant parvoviral (rAAV) virion (comprising a recombinant parvoviral (rAAV) vector as defined above) in an insect cell. Preferably, the method comprises the steps of: (a) culturing an insect cell as defined in herein above under conditions such that recombinant parvoviral (rAAV) vector is produced; and, (b) recovering of the recombinant parvoviral (rAAV) vector. It is understood here that the recombinant parvoviral (rAAV) vector produced in the method preferably is an infectious parvoviral or AAV virion that comprise the recombinant parvoviral (rAAV) vector nucleic acids. Growing conditions for insect cells in culture, and production of heterologous products in insect cells in culture are well-known in the art and described e.g. in the above cited references on molecular engineering of insects cells.

Preferably the method further comprises the step of affinity-purification of the (virions comprising the) recombinant parvoviral (rAAV) vector using an anti-AAV antibody, preferably an immobilised antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of rAAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In a further aspect the invention relates to a rAAV virion produced in the above described methods of the invention, using the nucleic acid constructs and cells as defined above. Preferably the rAAV virion comprises in its genome at least one nucleotide sequence encoding a gene product of interest, whereby the at least one nucleotide sequence is not a native AAV nucleotide sequence, and whereby in the stoichiometry of the AAV VP1, VP2, and VP3 capsid proteins the amount of VP1: (a) is at least 100, 105, 110, 120, 150, 200 or 400% of the amount of VP2; or (b) is at least 8, 10, 10.5, 11, 12, 15, 20 or 40% of the amount of VP3; or (c) is at least as defined in both (a) and (b). Preferably, the amount of VP1, VP2 and VP3 is determined using an antibody recognising an epitope that is common to each of VP1, VP2 and VP3. Various immunoassays are available in the art that will allow quantify the relative amounts of VP1, VP2 and/or VP3 (see e.g. Using Antibodies, E. Harlow and D. Lane, 1999, Cold Spring Harbor Laboratory Press, New York). An suitable antibody recognising an epitope that is common to each of the three capsid proteins is e.g. the mouse anti-Cap B1 antibody (as is commercially available from Progen, Germany). A preferred rAAV virion according to the invention is a virion comprising in its genome at least one nucleotide sequence encoding a gene product of interest, whereby the at least one nucleotide sequence is not a native AAV nucleotide sequence, and whereby the AAV virion comprises a VP1 capsid protein comprises a leucine or a valine at amino acid position 1. A more preferred AAV virion according to the invention has the ratio's of capsid proteins as defined above and comprises a VP1 capsid protein comprises a leucine or a valine at amino acid position 1.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The disclosure of each reference set forth herein is incorporated herein by reference in its entirety.

The following Examples illustrate the invention:

EXAMPLES

Example 1

1.1 Materials and Methods
1.1.1 Cloning of Constructs
1.1.1.1 Construction of Baculovirus Transfer Vector pVD142

Plasmid pVD142 is constructed by inserting the baculovirus p10 promoter in front of the GFP expression cassette in pVD111. Plasmid pVD111 is constructed in several consecutive steps. First, an EcoRV-SapI linker was ligated into SnaBI linearized pDEST8 plasmid (Invitrogen) which comprises the Gateway destination cassette under control of the polyhedrin promoter resulting in pDEST8-linker plasmid. Then, the BBsIxAvrII Gateway destination fragment was isolated from this plasmid, blunted and cloned in between AAV2 ITR sequences by ligating it into pTRCGW that was digested with KpnIxSphI, blunted and dephosphorylated. Subsequently, the ITR-Gateway destination cassette-ITR fragment was obtained by digesting the plasmid with DraIIIxPciI and after blunting it was ligated into the baculovirus transfer vector pAcDB3. In the last step the CMV-GFP expression cassette was isolated from pFBGFPR using SspIxBstAPI, blunted and cloned into the EcoRV linearized pAcDB3 plasmid comprising the Gateway cassette flanked by ITRs resulting in pVD111. Finally, a p10 promoter fragment was amplified from pFBGFPR using the following primers:

The forward primer (AMT primer #327) sequence contains a XbaI site (underlined)

(SEQ ID NO: 23)
5'- TCCGGAC<u>TCTAGA</u>GGACCTTTAATTCAACCCAACAC -3'

The reverse primer (AMT primer #332) sequence contains a XhoI site (underlined)

(SEQ ID NO: 24)
5'- GCCTTCG<u>CTCGAG</u>CTCCTTTGATTGTAAATAAAATG -3'

This fragment was digested with XhoIxXbaI and ligated into the pVD111 plasmid which was linearized with the same enzymes resulting in pVD142. The presence of intact ITRs was checked by sequencing, but were not correct. For this reason pVD142 (lot #2) was constructed.
1.1.1.2 Construction of Baculovirus Transfer Vector pVD142(Lot #2)

The vector pVD111 was digested with XhoI*NotI and the 9517 bp fragment was purified from agarose gel using the QIAquick Gel Extraction Kit (Qiagen). The plasmid pVD142 was digested with XhoI*NotI and the 1038 bp fragment was isolated from agarose gel, purified and ligated into the XhoI*NotI digested vector pVD111. Subsequently, the ligation mix was transformed into chemically competent One Shot CcdB survival cells (Invitrogen) plated onto LB plates containing ampicilin and chloramphenicol and grown overnight at 30° C. After miniprep DNA isolation using the GenElute Plasmid Miniprep kit (Sigma-Aldrich) a restriction analysis with XhoI*NotI, MscI, AhdI and SmaI was performed to check on the presence of the p10 promoter and the viral ITRs. To reselect DNA of clone #1 it was transformed into chemically competent SURE-2 cells (Stratagene) and plated onto LB plates containing ampicilin.

Maxiprep DNA of pVD142 (lot #2, clone 1.1) was checked with control digestions using EagI*PstI, MscI and SmaI. Furthermore, ITRs were checked by sequencing performed by Seqwright. FIG. 1 shows a schematic representation of pVD142(lot #2).

1.1.1.3 Construction of pVD156

To construct the entry vector pVD156 containing the AAV2 Rep78/ACG sequence a PCR was performed on REP-ACG/PSC (patent application WO2007148971; herein also referred to as pVD88) using the following primers:

The forward primer (AMT primer #321) sequence contains a part of the AttB1 site (underlined):

```
                                    (SEQ ID NO: 25)
5'- CAAAAAAGCAGGCTCCTGTTAAGACGGCGGGG -3'
```

The reverse primer (AMT primer #322) sequence contains a part of the AttB2 site (underlined)

```
                                    (SEQ ID NO: 26)
5'- TACAAGAAAGCTGGGTTTATTGTTCAAAGATGCAGTCAT -3'
```

The PCR protocol and program are described in attachment 3.1 and 3.2, respectively (A-0181 p 005). The PCR product of 1869 bp was purified from gel and used in a second PCR to add the complete AttB sites on each end of the PCR product. This PCR was performed with the following primers:

The forward primer (AMT primer #323) sequence contains the AttB1 site (underlined):

```
                                    (SEQ ID NO: 27)
5'- GGGGACAAGTTTGTACAAAAAAGCAGGCTCCTGTTA -3'
```

The reverse primer (AMT primer #324) sequence contains the AttB2 site (underlined)

```
                                    (SEQ ID NO: 28)
5'- GGGGACCA CTTTGTACAAGAAAGCTGGGTTTATTG -3'
```

Figure 2:
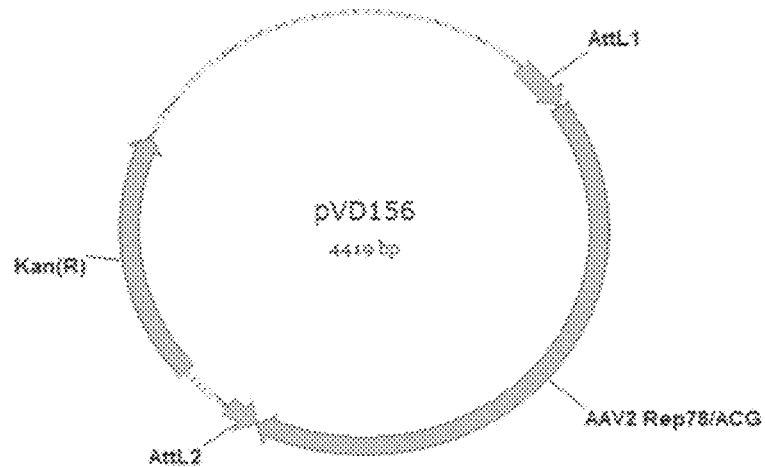
FIG. 2 shows a schematic representation of pVD156

Subsequently, the 1915 bp PCR product was purified from gel and a BP Clonase reaction was performed with the Gateway BP Clonase II enzyme mix. The pDONR221 plasmid (Invitrogen) was used as the entry vector and the reaction was performed according to the Gateway® Technology with Clonase™ II manual Version A. The BP clonase mixture was transformed into chemically competent TOP10 cells (Invitrogen) and plated onto LB plates containing kanamycine. After miniprep DNA isolation using the GenElute Plasmid Miniprep kit (Sigma-Aldrich) a restriction analysis with NcoI and KpnI was performed on the clones to check on the presence of the AAV2 Rep78/ACG cDNA (A-0181 p 024). The sequence of pVD156 was checked by sequencing. Maxiprep DNA was checked again with restriction analysis using NcoI-KpnI and ApaI-EcoRV. FIG. 2 shows a schematic representation of pVD156.

1.1.1.4 Construction of Baculovirus Transfer Vector pVD143

Figure 3:
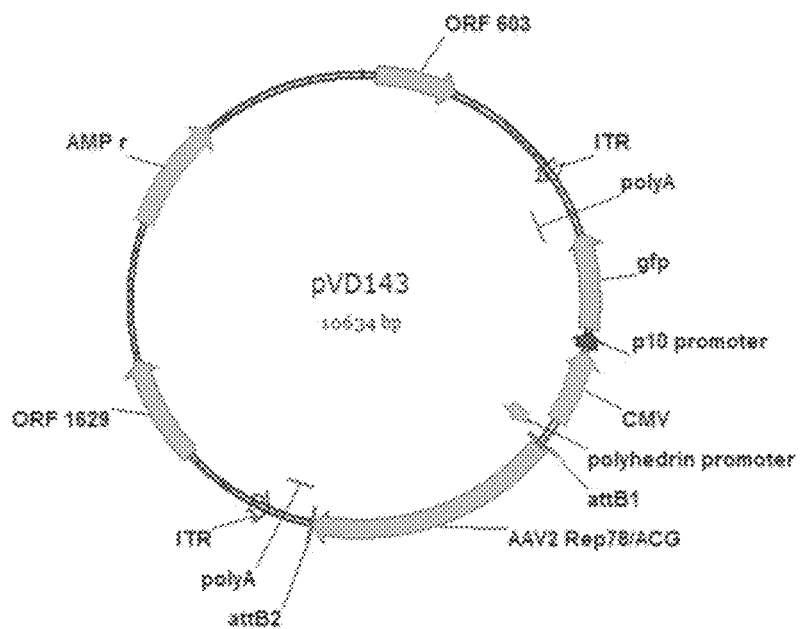
FIG. 3 shows a schematic representation of pVD143.

The baculovirus transfer vector pVD143 contains the pPolH-AAV2 Rep78/ACG and the pCMV-p10-GFP expression cassette between ITRs. This plasmid is constructed according to the Gateway® Technology using pVD142 (lot #2) as the destination vector and pVD156 as the entry clone. The LR reaction was performed as described in the Gateway® Technology with Clonase™ II manual Version A, but incubated o/n instead of 1 h. The LR clonase mixture was transformed into one vial of chemically competent TOP10 cells (Invitrogen) and added to 300 ml LB medium containing ampicilin. To preserve the two ITR sequences in pVD143 the culture was incubated o/n at 30° C. and thereafter maxiprep DNA was isolated using the QIAGEN Plasmid maxiprep kit (Qiagen). To check the presence of the AAV2 Rep78/ACG expression cassette a restriction analysis with EagI and PstI was performed on the maxiprep DNA and compared to the restriction pattern of the destination vector pVD142. FIG. 3 shows a schematic representation of pVD143.

1.1.1.5 Generation of Rep Error Prone (Rep-EP) Libraries

To introduce random point mutations into the AAV2 Rep78/ACG sequence an error prone (EP) PCR was performed using the GeneMorph II Random Mutagenesis Kit (Stratagene). First, the AAV2 Rep78/ACG sequence was amplified from plasmid pVD88 using the following primers:

The forward primer (AMT primer #321) sequence contains a part of the AttB1 site (underlined):

```
                                    (SEQ ID NO: 25)
5'- CAAAAAAGCAGGCTCCTGTTAAGACGGCGGGG -3'
```

The reverse primer (AMT primer #322) sequence contains a part of the AttB2 site (underlined)

```
                                    (SEQ ID NO: 26)
5'- TACAAGAAAGCTGGGTTTATTGTTCAAAGATGCAGTCAT -3'
```

The PCR product of 1869 bp was purified from gel and used in the EP-PCR to introduce the random point mutations. To generate Rep error prone (Rep-EP) libraries with different mutation frequencies the initial amount of target DNA was ranging from 0.1 ng to 250 ng, resulting in the libraries Rep-EP1 to Rep-EP5 (Table 1).

Five different EP-PCRs were performed with the AMT primerset #321/#322. Subsequently, the Rep-EP PCR products were purified from gel and to add the complete AttB sites a PCR was performed on 100 ng of each Rep-EP library with the following primers:

The forward primer (AMT primer #323) sequence contains the AttB1 site (underlined):

```
                                    (SEQ ID NO: 27)
5'- GGGGACAAGTTTGTACAAAAAAGCAGGCTCCTGTTA -3'
```

The reverse primer (AMT primer #324) sequence contains the AttB2 site (underlined)

```
                                    (SEQ ID NO: 28)
5'- GGGGACCA CTTTGTACAAGAAAGCTGGGTTTATTG -3'
```

Subsequently, the 1915 bp PCR products were purified from gel and a BP recombination reaction was performed with the Gateway BP Clonase II enzyme mix (Invitrogen). The pDONR221 plasmid (Invitrogen) was used as the entry vector and the reactions were performed according to the Gateway® Technology with Clonase™ II manual Version A, with the exception that the reactions were done o/n instead of 1 h. Thereafter, 1 ul of the BP Clonase reaction mixture was transformed into chemically competent TOP10 cells (Invitrogen) and plated onto LB plates containing kanamycine. After o/n culturing of several different clones of each library miniprep DNA was isolated and checked with restriction analysis using NcoI*KpnI. The mutation frequency of each library was estimated by sequencing of two clones of each library using AMT primer #210:

(SEQ ID NO: 29)
5'- AGGCCCAAACAGCCAGATG -3'

Subsequently, the remaining amount of BP reaction mixture of the Rep-EP1 and 3 was transformed into two vials of chemically competent TOP10 cells (Invitrogen), added to 500 ml LB medium containing kanamycine and grown o/n at 30° C. Maxiprep DNAs were isolated using the QIAGEN Plasmid maxiprep kit (Qiagen), checked by restriction analysis using NcoI*KpnI and are named pDONR221-Rep-EP1 and pDONR221-Rep-EP3, respectively.

The two generated pDONR221-Rep-EP libraries were cloned into the destination vector pVD142 with the LR recombination reaction and according to the Gateway® Technology with Clonase™ II manual Version A. For each library the reactions were performed in triplo and incubated for 2 h. Each LR reaction mixture was transformed into one vial of chemically competent TOP10 cells (Invitrogen) and after that the three transformations were combined. To determine the EP library size 30 µl of each transformed library was plated onto LB plates containing ampicilin and the remaining amount was added to 500 ml LB medium. The cultures were incubated o/n at 30° C. to preserve the two ITR sequences present in the destination plasmid and thereafter maxiprep DNA was isolated using the QIAGEN Plasmid maxiprep kit (Qiagen). To check the performance of the LR reaction a restriction analysis with EagI-PstI was performed on the maxiprep DNA and compared to the restriction pattern of the destination vector pVD142 and pVD143. The three pDONR221-Rep-EP libraries that were cloned to the baculovirus transfer vector pVD142 are named pVD142-Rep-EP1 and pVD142-Rep-EP3.

1.1.1.6 Generation of Baculovirus Rep-EP Libraries

To produce baculovirus Rep-EP libraries (Bac.Rep-EP) Sf9 cells were co-transfected with one of the different pVD142-Rep-EP libraries and the flashBAC viral DNA (Oxford Expression Technologies) according to the FlashBAC one-step baculovirus protein expression User Guide, but with the exception of some small changes. In brief, 1×10⁶ Sf9 cells were seeded in a well of 6-wells plate and incubated at 28° C. for 1 h to attach. During the incubation the co-transfection mix was prepared by diluting 20 ng of flashBAC DNA and 2 µg pVD142-Rep-EP1 or -EP3 in 500 µl of SF-900II medium (Invitrogen). The transfection reagent Cellfectin from Invitrogen (5 µl) was diluted separately in 500 µl SF-900II medium, added to the DNA mixture and incubated for 15 min at RT. The attached cells were washed once with SF-900II medium and incubated for 5 h with the DNA/Cellfectin mixture. Subsequently, 1 ml of fresh SF900II medium (supplemented with 20% FBS) wash added to the cells and 5 days after transfection the Bac.Rep-EP1 and EP-3 p0 were harvested by centrifugation the culture medium at 1900 g for 15 min. The supernatant containing the baculoviruses was transferred to new tubes and stored at 4° C. in the dark. The amplification of the Bac.Rep-EP libraries to p1 was performed in SF+ cells under serum free conditions. Briefly, the Bac.Rep-EP p0 libraries were diluted 1:100 in shaker flasks containing 50 ml SF+ cells at a density of ~2.0×10⁶ c/ml and harvested three days p.i. as described above. The baculovirus stocks Bac.VD142 and Bac.VD143 were generated simultaneously and in the same way as the Bac.Rep-EP libraries.

After the first selection round the baculovirus libraries Bac.select-EP3 p1 and Bac.EP-EP3 p1 were made in the same way.

The insert of the different Rep baculovirus libraries was checked by performing a PCR on baculoviral DNA isolated from these stocks using the forward primer (AMT primer #349): 5'-GCGGATCATCACAAGTTTGTAC-3' (SEQ ID NO: 30) And the reverse primer (AMT primer #350): 5'-ACCACTTTGTACAAGAAAGCTG-3' (SEQ ID NO: 31)

Baculovirus stocks with the correct insert should generate a 1935 bp fragment.

1.1.1.7 Generation of the Baculovirus Select-EP-EP3 Clones

The Bac.select-EP-EP3 clones were generated in the same manner as the baculovirus libraries. The ORF/Rep ratios of the Bac.select-EP-EP3 clones 1-20 p1 were determined by Q-PCR analysis using the primer sets pr180/181 and pr209/210.

(SEQ ID NO: 32)
Pr180: 5' CGAACCGATGGCTGGACTATC 3'

(SEQ ID NO: 33)
Pr181: 5' TGCTGCTACAAGATTTGGCAAGT 3'

(SEQ ID NO: 34)
Pr209: 5' CTAAACGGGTACGATCCCCAAT 3'

(SEQ ID NO: 29)
Pr210: 5' AGGCCCAAACAGCCAGATG 3'

Due to the variable ORF/Rep ratios a plaque assay was performed, single plaques were amplified to p1 and the ORF/Rep ratios was determined again. Baculovirus stocks with the best ORF/Rep ratio (around value 1) were used in the rAAV5 productions.

1.1.1.8 First Selection Round

During the first selection round rAAV5 productions were performed using the Rep libraries Bac.Rep-EP1 or Bac.Rep-EP3 and Bac.VD92 p5 in a 1:1 ratio. Productions with Bac.VD142 and Bac.VD143 were taken along as control productions. In brief, the different baculovirus stocks were diluted 1:100 in shaker flasks containing in log-phase growing SF+ cells at a density of ~2.0×10⁶ c/ml. Three days p.i. the rAAV5 productions were harvested by adding 10× lysisbuffer and after a 1 h incubation a benzonase treatment was performed at 37° C. Crude lysates were clarified by 1900 g centrifugation and the virus titers were determined using a Q-PCR method with the CMV promoter as target.

1.1.1.9 Second Selection Round

During the second selection round rAAV5 productions were performed using the selected Rep-EP3 library (Bac.selectEP3 p1) or the selected Rep-EP3 library that was subjected to a new mutation round (Bac.EP-EP3 p1) and Bac.VD92 p5 in a 1:1 ratio. Productions with Bac.VD142 and Bac.VD143 were taken along as control productions. Productions were performed as in the first selection round and repeated twice. The rAAV5 virus titers were determined using a Q-PCR method with the CMV promoter as target.

1.1.1.10 Purification of rAAV5 Particles

Crude lysates from the rAAV5 productions with Bac.Rep-EP3 p1 or Bac.EP-EP3 p1 were clarified by 1900 g centrifugation and subsequent filtration using a 0.45 µm Millipak 20 (Millipore) filter. Further purification of the different rAAV5 particles was performed by affinity chromatography AVB sepharose column (GE). The purified rAAV5 batches were stored at −20° C. Viral titers of crude lysates and affinity eluates were determined using a Q-PCR method with the CMV promoter as target.

1.1.1.11 Amplification and Cloning of Selected Rep Libraries

Viral DNA was isolated from the purified rAAV5 samples. In brief, 1/50 volume of DNAse I (Roche) was added to the purified rAAV5 sample and incubated for 20 min at 37° C. To optimize the reaction conditions for proteinase K treatment the end concentrations in the sample were next changed to 10 mM Tris-HCl (pH 8.0), 100 mM NaCl, 10 mM EDTA and 0.5% SDS. Proteinase K (Roche) was added to a final concentration of 2 mg/ml and the proteinase K treatment was performed for 1 h at 37° C. Subsequently, 0.92 volume of RNA lysis buffer (Promega) and poly(A) to a final concentration of 24 ng/ml was added. To bind the viral DNA 1/24 volume of MagneSil BLUE (Promega) was added and the sample was placed on a shaker for 5 min at RT. MagneSil beads were pelleted by 2800 g centrifugation for 5 min at RT, washed once with RNA lysis buffer and two times with 80% ethanol. The MagneSil beads were then transferred to an eppendorf tube and washed twice with 80% ethanol. After transferring to the eppendorf tubes the MagneSil beads were not pelleted by centrifugation, but separated by using the magnetic separation device for eppendorf tubes (Chemagen). The MagneSil beads were incubated at 65° C. until all ethanol was evaporated. Viral DNA was first eluted in 200 µl MQ by incubating for 5 min at 65° C. followed by thoroughly vortexing of the beads and then the supernatant was transferred to a new eppendorf tube. The second elution in 200 µl MQ was performed o/n at 4° C. The two eluates were combined and used in a PCR reaction to amplify and clone the selected Rep library.

To amplify the selected Rep-EP3 library a PCR using AMT primerset #321/#322 was performed on different amounts (2.5, 10 or 25 µl) of isolated viral DNA. The amplified fragments of ~1869 bp were purified from gel and 10 ng was used in the EP-PCR with AMT primerset #323/#324 to introduce new mutations. Subsequently, the ~1915 bp PCR products were purified from gel and cloned to pDONR221 as described in section 1.1.1.5, resulting in the pDONR221-EP-EP3 library. The pDONR221-select-EP3 library contains only the Rep-EP3 sequences that were selected in the first round and that were not subjected to a new mutation round. This library was made by performing a PCR on different amounts (2.5 or 10 µl) of isolated viral DNA using the AMT primerset #323/#324 and cloning the amplified products to pDONR221 as described above. Maxiprep DNA isolates from the different libraries were checked with restriction analysis using PstI. The mutation frequency was estimated by sequencing six clones of each library. This sequencing was performed using AMT primer #210. The pDONR221-select-EP3 and pDONR221-EP-EP3 libraries were cloned into the destination vector pVD142 (lot #2) as described in section 1.1.1.5 and are named pVD142-selectEP3 and pVD142-EP-EP3, respectively. To check the performance of the LR reaction a restriction analysis with EagI-PstI was performed on the maxiprep DNA isolates and compared to the restriction pattern of the destination vector pVD142 (lot #2) and pVD143. Recombinant baculovirus stocks comprising these libraries were generated as described in section 1.1.1.6 and are named Bac.select-EP3 and Bac.EP-EP3, respectively.

After the second selection round viral DNA was isolated from the purified rAAV5 sample that was produced with Bac.EP-EP3 p1. The viral DNA isolation, amplification and cloning of the selected EP-EP3 library was performed as described above. This results in the new library named pDONR221-selectEP-EP3. From this library 20 clones were randomly picked and checked with restriction analysis using BstXI. The pDONR221-select-EP-EP3 clones 1-20 were cloned into the destination vector pVD142 (lot #2) as described in section 1.1.1.5 and are named pVD142-select-EP-EP3 clones 1-20. The number of mutations in each clone and the overall mutation frequency was determined by sequence analysis. Subsequently, a baculovirus stock of each clone was generated as described in section 1.1.1.6 and were named Bac.select-EP-EP3 clone 1-20.

1.1.1.12 Productions with Bac.Select-EP-EP3 Clones 1-20

To test the Bac.select-EP-EP3 clones 1-20 in their ability to produce rAAV5 30 ml productions were performed. The Bac.select-EP-EP3 was added in 5:1:1 ratio compared to Bac.VD92 and Bac.VD43. The productions with Bac.VD143 or Bac.VD142 in a 5:1:1 ratio with Bac.VD92 and Bac.VD43 were used again as positive and negative controls, respectively. Finally, virus titers were determined using a Q-PCR method with the CMV promoter as target. Productions with the plaque purified clones were performed in the same way.

1.2 Results 1.2.1 Generation of Rep Error Prone (Rep-EP) Libraries

Five Rep-EP libraries were generated by performing an error prone PCR (EP-PCR) on the 1869 bp fragment that comprises the AAV2 Rep78/ACG expression cassette. By changing the amount of initial target DNA in the different EP-PCRs the number of introduced mutations will alter. After cloning the Rep-EP libraries into the Gateway entry vector pDONR221 the mutation frequencies were determined by partly sequencing of two clones of each library. The estimated amount of mutations per kbp in each library is shown in Table 3. As expected, the library made out of a low initial target DNA has a high mutation frequency and the one made out of a high initial target DNA has a low mutation frequency. The sizes of the five libraries ranged from ~0.7-1.3×10$^4$ clones and were estimated by counting the amount of bacterial colonies that were formed after plating a small percentage of the transformed cells, while the rest of the library was grown in a shaker flask.

TABLE 3

Mutation frequency in the five Rep-EP libraries. Two clones of each Rep-EP library were sequenced using the Rep specific AMT primer #210 and the number of mutations was determined by sequence analysis. The mutation frequency for each library was estimated and is represented as mutations/kbp.

| Rep library | Amount of target DNA | Mutations/kbp |
| --- | --- | --- |
| EP1 | 0.1 ng | ~9-13 |
| EP2 | 1.0 ng | ~7-11 |
| EP3 | 10 ng | ~3-5 |
| EP4 | 50 ng | ~3-6 |
| EP5 | 250 ng | ~0-1 |

Figure 4A:
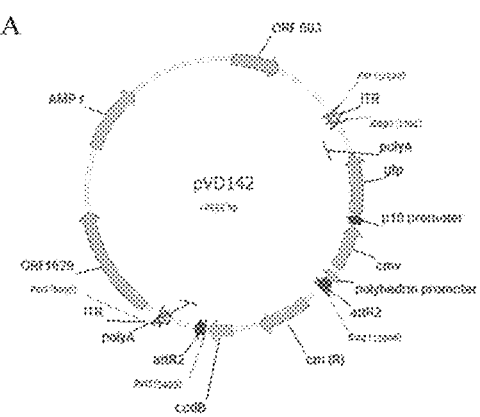
Figure 4B:
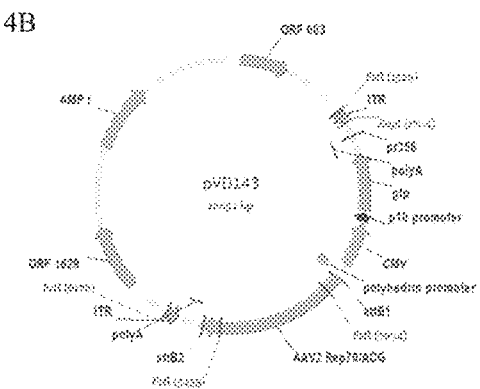
Figure 4B:
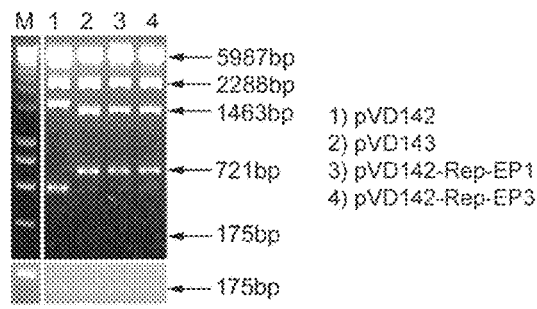

As the appropriate mutation frequency for the Rep directed evolution has not been established two different Rep-EP libraries were used in the first selection round. The Rep-EP1 and EP3 libraries were cloned to the baculovirus transfer plasmid pVD142(lot #2) using the LR recombination reaction. This results in the libraries pVD142-Rep-EP1 and 3 which were checked again with restriction analysis as shown in FIGS. 4A, 4B, and 4C. The obtained restriction fragments had the expected sizes and were identical to the restriction pattern of pVD143, which contains the non-mutated AAV2 Rep78/ACG expression cassette. The transfer plasmid pVD142 was used as the negative control and was shown to have a different restriction pattern.

1.2.2 First Selection Round

Figure 5:
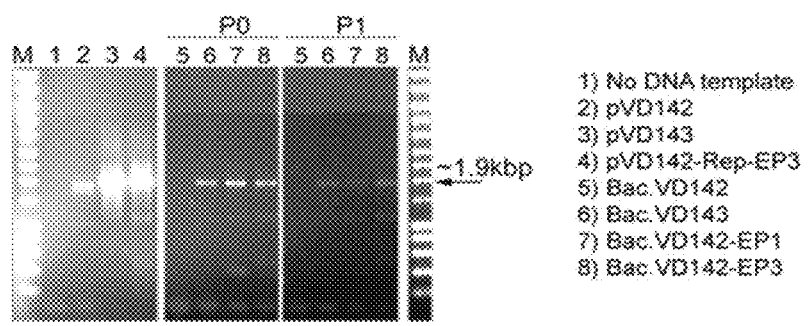
FIG. 5 shows the quality control of Bac.Rep-EP libraries. Baculoviral DNA was isolated from p0 and p1 baculovirus stocks and used in an insert control PCR using primerset #349/350. As shown for all baculovirus stocks this resulted predominantly in a ~1.9 kbp fragment. Four different plasmids were used as positive controls (lane 2-4). M, smartladder (Eurogentec).

Before starting the selection procedure the baculovirus libraries used were checked by performing a PCR on baculoviral DNA isolated from these stocks. This PCR specifically amplifies the DNA that is present between the two Att recombination sites, the part where the Rep-EP library is located. The PCR on viral DNA from Bac.VD143, Bac.Rep-EP1 and 3 amplified a DNA fragment from the expected size demonstrating that the baculoviruses contain the Rep libraries (FIG. 5). During the first selection round rAAV5 productions were performed using the Rep libraries Bac.Rep-EP1 or 3 p1 and Bac.VD92 p5 in a 1:1 ratio. Productions with Bac.VD142 p1 or Bac.VD143 p1 in a 1:1 ratio with Bac.VD92 p5 were taken along as a negative and positive control production, respectively. Three days p.i. the productions were harvested and the rAAV5 virus titers were determined in crude lysate using the CMV Q-PCR method. The virus titers of the different rAAV5 productions in two independent experiments are shown in Table 4. In both experiments the production with Bac.VD143 gave comparable virus titers. The production with Bac.Rep-EP1 gave a similar virus titer as the negative control production with Bac.VD142. Thus, this is background level. The production with Bac.Rep-EP3 resulted twice in a very low virus titer. However, this virus titer is slightly above background level and indicates that there is probably specific packaging of ssDNA encoding Rep-EP3 sequences. Therefore only the selected Rep-EP3 library was isolated, amplified and re-cloned to the entry vector.

TABLE 4

Virus titers of rAAV5 productions after first selection round. Virus titers of the rAAV5 productions performed in two independent experiments determined with Q-CPR analysis.

| Baculovirus | Virus titer (gc/ml) | |
| --- | --- | --- |
|  | Exp #1 | Exp #2 |
| Bac.VD142 | n.a. | 1.7E+07 |
| Bac.VD143 | 1.3E+09 | 1.7E+09 |
| Bac.Rep-EP1 | 8.5E+07 | 1.9E+07 |
| Bac.Rep-EP3 | 8.7E+07 | 9.7E+07 |

Figure 6A:
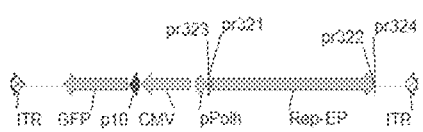
FIGS. 6A, 6B, and 6C show the amplified Rep-EP3 sequences selected after the first selection round, the introduction of new mutations and restriction analysis of the two new libraries. A) Schematic overview of the viral DNA isolated after the first selection round. The primer binding sites that flank the selected Rep-EP3 sequences are indicated by pr321-pr324. B) C) An agarose gel showing the amplified PCR products when using the AMT primer set #321/#322 and different amounts of viral DNA input isolated after the first selection round. The 1869 bp fragments were isolated from gel and 10 ng was used as a template in the EP-PCR to introduce new mutations. D) Restriction analysis of the two new libraries pVD142-select-EP3 and pVD142-EP-EP3 using PstI-EagI. M, smartladder (Eurogentec).
Figure 6B:
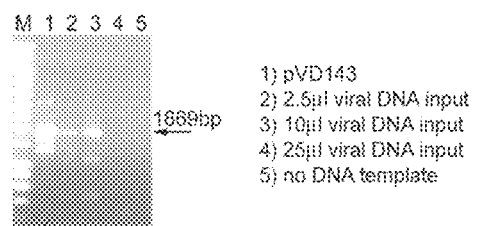

N.a., not applicable 1.2.3 Amplification and Cloning of Selected Rep-EP3 Library The rAAV5 particles that were produced during the first selection round with the Rep-EP3 library were purified using affinity chromatography and the viral DNA, presumably containing the selected Rep-EP3 library, was isolated. Subsequently, this selected Rep-EP3 library was amplified by PCR and different amounts of initial target DNA (FIG. 6B). After performing an additional PCR on selected Rep-EP3 library using primerset #323/324 the correct products (~1915 bp) were purified and cloned into the entry vector pDONR221, resulting in the new libraries pDONR221-select-EP3(2.5 µl) and pDONR221-select-EP3(10 µl). The selected Rep-EP3 library was also subjected to a new mutation round using the GeneMorph II Random Mutagenesis Kit. The 1869 bp fragments were used as a template in the error prone PCR using #323/324. The obtained fragments were purified and cloned to the entry vector resulting in pDONR221-EP-EP3(2.5 µl) and pDONR221-EP-EP3(10 µl). The mutation frequency of the different libraries was also determined again by partly sequencing of three clones of each library. As shown in Table 5 the average mutation frequency for the pDONR221-select-EP3 library is ~5.9 mutations/kbp and after a new mutation round the frequency was increased to ~8.2 mutations/kbp.

TABLE 5

Mutation frequency in the select-EP3 libraries. Three clones of each select-EP or EP-EP3 library were sequenced using the Rep specific AMT primer #210 and the number of mutations was determined by sequence analysis. The mutation frequency for each library was estimated and is represented as mutations/kbp.

| Rep library | Mutations/kbp | Average Mutations/kbp |
| --- | --- | --- |
| pDONR221-select-EP3(2.5 µl) | ~4.8 | ~5.9 |
| pDONR221-select-EP3(10 µl) | ~7.0 |  |
| pDONR221-EP-EP3(2.5 µl) | ~4.6 | ~8.2 |
| pDONR221-EP-EP3(10 µl) | ~11.7 |  |

Figure 6C:
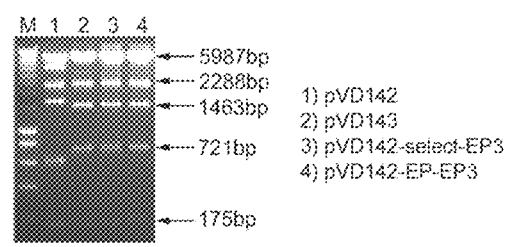

Maxiprep DNA of the two pDONR221-select-EP3 libraries was mixed in an equal ratio and cloned to the baculovirus transfer plasmid pVD142 using the LR recombination reaction, resulting in the library pVD142-select-EP3. The pVD142-EP-EP3 library was generated in the same way. The maxiprep DNA isolates from these two libraries were checked with restriction analysis as shown in FIG. 6C. The obtained restriction fragments had the expected sizes and were identical to the restriction pattern of pVD143. The transfer plasmid pVD142 was used as the negative control and was shown to have a different restriction pattern.

1.2.4 Second Selection Round

Figure 7:
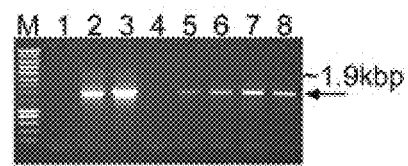
FIG. 7 shows the quality control of the Rep-EP libraries second selection round used in the second selection round. Baculoviral DNA isolated from p1 baculovirus stocks was used in an insert control PCR using primerset #349/350. Except for Bac.VD142, all baculovirus stocks revealed the presence of the correct 1.9 kbp fragment. Plasmids pVD142 and pVD143 were used as positive controls (lane 2-3).

Before starting the second selection round the new baculovirus libraries Bac.select-EP3 and Bac.EP-EP3 were generated by recombination of the plasmids libraries with the baculoviral flashBAC DNA and amplified to p1. The control baculoviruses Bac.VD142, Bac.VD143 and Bac.Rep-EP3 were made at the same moment and also amplified to p1. The new baculovirus libraries and control baculoviruses were also checked by PCR analysis. Bac.VD143 and the three Rep baculovirus libraries all revealed the presence of the correct fragment (FIG. 7). During the second selection round 400 ml rAAV5 productions were performed using the baculovirus libraries and Bac.VD92 p5 in a 1:1 ratio and three days p.i. the productions were harvested virus titers were determined in crude lysates using the CMV Q-PCR method. The control productions were performed in 25 ml volumes. The virus titers of the different rAAV5 productions are shown in Table 6.

The control productions with Bac.VD143 and Bac.VD142 gave virus titers of $2.3 \times 10^9$ and $7.4 \times 10^4$ gc/ml, respectively. The production with the selected Rep-EP3 library (Bac.select-EP3) was slightly higher than the production with the Rep-EP3 library used in the first selection round (Bac.Rep-EP3), but both were still very low. Remarkable, the production with Bac.EP-EP3 resulted in 3-fold higher virus titer as compared to Bac.VD143, which could indicate that this library contains more improved Rep proteins than the Bac.select-EP3 library.

TABLE 6

Virus titers of rAAV5 productions after second selection round. Virus titers of the rAAV5 productions were determined with Q-CPR analysis.

| Baculovirus | Virus titer (gc/ml) |
| --- | --- |
| Bac.VD142 | 7.4E+04 |
| Bac.VD143 | 2.3E+09 |

TABLE 6-continued

Virus titers of rAAV5 productions after second selection round. Virus titers of the rAAV5 productions were determined with Q-CPR analysis.

| Baculovirus | Virus titer (gc/ml) |
|---|---|
| Bac.Rep-EP3 | 2.7E+07 |
| Bac.select-EP3 | 5.7E+07 |
| Bac.EP-EP5 | 7.6E+09 |

1.2.5 Cloning of Selected Rep-EP-EP3 Library and Sequence Analysis of 20 Clones

Figure 8:
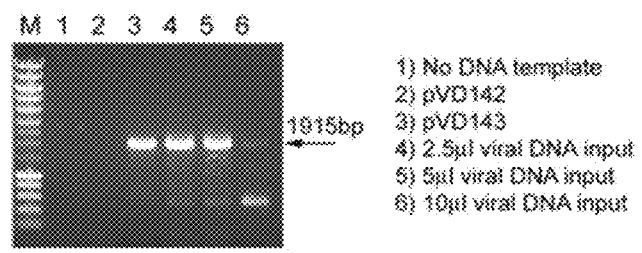
FIG. 8 shows the amplified selected Rep-EP-EP3 sequences after the second selection round when using the AMT primer set #323/#324 and different amounts of viral DNA template. The 1915 bp fragment obtained with the PCR in lane 5 was isolated from gel and cloned to pDONR221, resulting in the pDONR221-selectEP-EP3 library. Plasmids pVD142 and pVD143 are used as a negative control and positive control in the two different PCR reactions. M, smartladder (Eurogentec).

The rAAV5 particles that were produced during the second selection round of the Rep-EP-EP3 library (Table 6) were purified using affinity chromatography and the viral DNA (i.e. the selected Rep-EP-EP3 library) was isolated. Subsequently, this selected Rep-EP-EP3 library was amplified by PCR using primerset #323/324 (FIG. 8) and different amounts of initial target DNA. The ~1915 bp product obtained with 5 µl initial target DNA was purified and cloned into the entry vector pDONR221, resulting in the new library pDONR221-select-EP-EP3. From this new library 20 clones were randomly picked and checked by restriction analysis. Except for clone 6, the restriction analysis on the different clones and the pDONR221-select-EP-EP3 library revealed the same restriction fragments as the positive control pVD156. Thereafter, the 20 clones were transferred to the plasmid pVD142 using the LR recombination reaction, resulting in pVD142-select-EP-EP3 clones 1-20. Miniprep DNA isolates of these 20 clones were checked with restriction analysis using MscI. The obtained restriction fragments had the expected sizes and were comparable to the restriction pattern of pVD143. The destination plasmid pVD142 was used as the negative control and was shown to have a different restriction pattern.

Before testing all the different clones in rAAV5 productions the complete Rep expression cassette of all clones was sequenced by Baseclear. The mutation frequency is ranging from 2.1-6.4 mutations per kbp and the average frequency is 4.1 mutations per kbp (Table 7). Most mutations were missense mutations (65%) which result in aminoacids changes while the other 19% and 16% were silent and non-sense mutations, respectively. A deletion of 1 or 185 bp was also found in clones 4, 6 and 11.

TABLE 7

Mutation frequency and type of mutations determined in the select-EP-EP3 clones 1-20. Sequence analysis revealed that the average mutation frequency is 4.1 mutations/kbp and 65% of the mutations are missense. Clones 4, 6 and 11 have a 1 bp or 185 bp deletion.

| Clone | # mut | # mut/ kbp | missense | silent | non-sense | deletion (bp) |
|---|---|---|---|---|---|---|
| 1 | 6 | 3.2 | 4 | 1 | 1 | 0 |
| 2 | 5 | 2.7 | 4 | 1 | 0 | 0 |
| 3 | 6 | 3.2 | 3 | 2 | 1 | 0 |
| 4 | 9 | 4.8 | 6 | 1 | 2 | 1 |
| 5 | 11 | 5.9 | 8 | 2 | 1 | 0 |
| 6 | 6 | 3.2 | 5 | 1 | 0 | 185 |
| 7 | 10 | 5.4 | 5 | 3 | 2 | 0 |
| 8 | 11 | 5.9 | 7 | 2 | 2 | 0 |
| 9 | 12 | 6.4 | 7 | 4 | 1 | 0 |
| 10 | 4 | 2.1 | 3 | 1 | 0 | 0 |
| 11 | 9 | 4.8 | 8 | 1 | 0 | 1 |
| 12 | 8 | 4.3 | 4 | 3 | 1 | 0 |
| 13 | 8 | 4.3 | 5 | 1 | 2 | 0 |
| 14 | 10 | 5.4 | 7 | 2 | 1 | 0 |
| 15 | 6 | 3.2 | 4 | 1 | 1 | 0 |
| 16 | 5 | 2.7 | 3 | 0 | 2 | 0 |
| 17 | 6 | 3.2 | 4 | 0 | 2 | 0 |
| 18 | 7 | 3.8 | 5 | 0 | 2 | 0 |
| 19 | 5 | 2.7 | 2 | 2 | 1 | 0 |
| 20 | 8 | 4.3 | 5 | 1 | 2 | 0 |
| average | | 4.1 | 65% | 19% | | 16% |

1.2.6 Testing of Rep-Select-EP-EP3 Clones 1-20 on rAAV5 Virus Titers

Figure 9A:
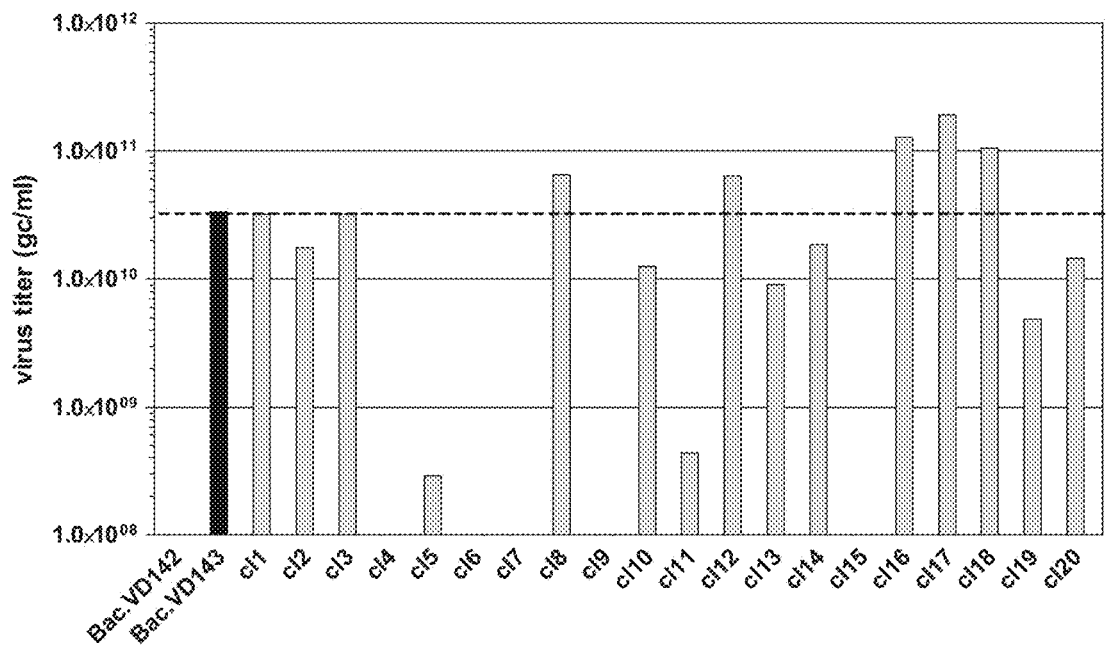
FIGS. 9A and 9B show the virus titers of rAAV5 productions with Bac.Rep-select-EP-EP3 clones 1-20 and the control productions with Bac.VD142 and Bac.VD143. A) Virus titers of the rAAV5 productions using the different clones were determined in crude lysates with the Q-PCR method. Clones 4, 6, 7, 9 and 15 generated virus titers that were comparable to background level (Bac.VD142). Clones 1 and 3 gave comparable titers as the positive control Bac.VD143 (FIG. 9A, black bar), while clones 8, 12 and 16-18 generated higher virus titers. Productions with all other clones resulted in lower virus titers as the Bac.VD143, but were above background level. B) Virus titers of the rAAV5 productions using plaque purified clones were determined in crude lysates using the Q-PCR method. Productions with clones 12, 13 and 16-20 gave virus titers that were in the range of $1-2 \times 10^{11}$ gc/ml, while the positive control production with Bac.VD143 (black bar) resulted in a titer of $4 \times 10^{10}$ gc/ml. The negative control production with Bac.VD142 generated a value of $8.4 \times 10^{7}$ gc/ml.

The Bac.select-EP-EP3 clones 1-20 were tested in rAAV5 productions and virus titers were compared to productions using Bac.VD143 or Bac.VD142. As shown in FIG. 9A productions with clones 4, 6, 7, 9 and 15 generated virus titers that were comparable to background level (Bac.VD142). Clones 1 and 3 gave comparable titers as the positive control Bac.VD183 (FIG. 9A, black bar), while clones 8, 12 and 16-18 generated higher virus titers. Productions with all other clones resulted in lower virus titers as the Bac.VD143, but were above background level.

Figure 9B:
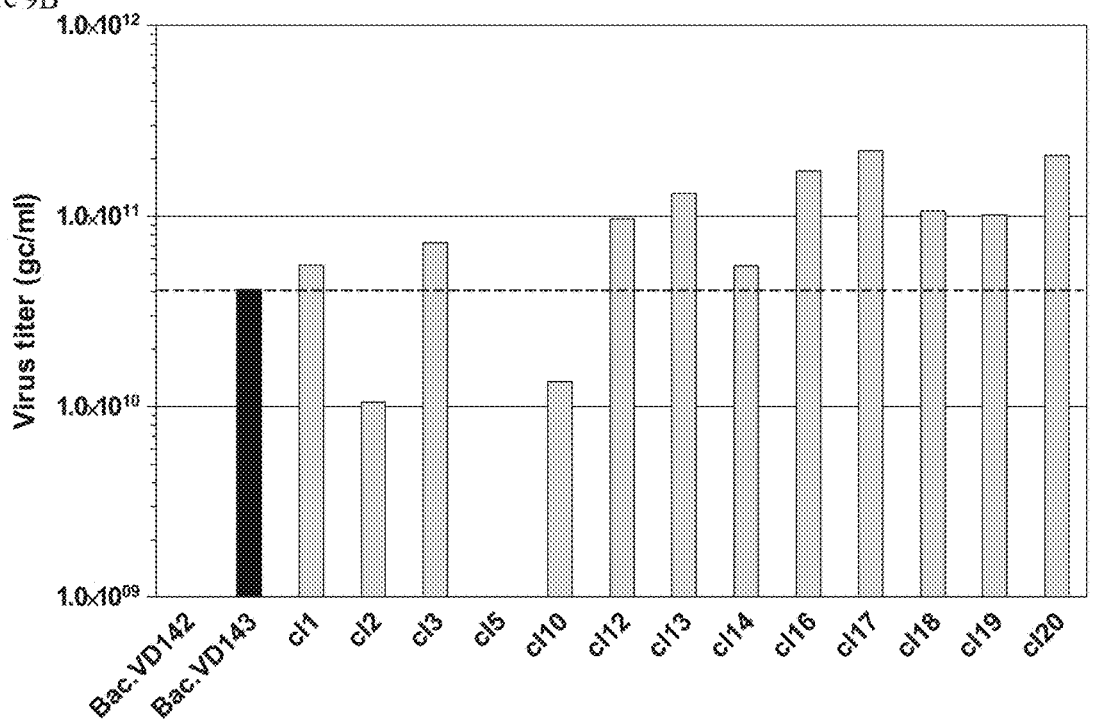

The product quality of these 20 clones was also checked by determining the ORF/Rep ratios and were shown to be very variable between the different clones. Therefore, the most interesting clones were plaque purified, checked on a correct ORF/Rep ratio (around value 1) and used in the experiment depicted in FIG. 9B. Clones 4, 6, 7, 9, 11 and 15 were excluded from this experiment, because these gave very low virus titers in the previous experiment (see FIG. 9A). Unfortunately, from the plaque assay of clone 8 no baculoviruses could be amplified to p1 and was therefore not included in this experiment. As shown in FIG. 9B the virus titers in the control production is ~3×10$^{10}$ gc/ml and the productions with clones 1, 3 and 14 gave virus titers of 6-7×10$^{10}$ gc/ml, while the productions with clones 2, 5 and 10 were lower than the control productions. Productions with clones 12, 13 and 16-20 resulted in virus titers of 1-2×10$^{11}$ gc/ml, which is 3-5 fold higher as compared to the control productions.

In conclusion, of 20 clones that were randomly picked from the selected Rep-EP-EP3 library 7 clones generated virus titers that were 3-5 folds higher as compared to the control production using the non-mutated AAV2 Rep78/ACG expression cassette.

Example 2

2.1 Materials and Methods
2.1.1 Cloning of Constructs
2.1.1.1 Construction of pVD210 and pVD215-218 and pVD220

The Rep sequences from REP-ACG/PSC (patent application WO2007148971; herein also referred to as pVD88), pVD142-selectEP-EP3 clone 13, 16-18 and 20 were amplified by PCR using primerset pr460/pr461, digested with PpuMI and XbaI and cloned into the vector pVD88 which was digested with PpuMI*XbaI resulting in the constructs pVD210, pVD215-218 and pVD220, respectively. The forward primer pr460 sequence contains the PpuMI restriction site (underlined): 5'-TACGAGATTGTGATTA AGGTCCCCAG-3' (SEQ ID NO: 35) The reverse primer pr461 sequence contains the XbaI restriction site (underlined) 5'-CATCAC TCTAGACTTACTTGGCTCCACCCTTTTTG-3' (SEQ ID NO: 36) To verify the cloned Rep sequences all constructs were sequenced.

2.1.1.2 Construction of pVD211 and pVD212

The plasmids pVD211 and pVD212 were generated by performing a PCR using primerset pr460/pr462 on pVD142-selectEP-EP3 clone 19 and 20, PCR fragments were digested with PpuMI and SexAI and by cloning these inserts into pVD88 which was digested with PpuMI*SexAI. The reverse primer pr462 sequence contains the SexAI restriction site (underlined): 5'-GCTGCTGG CCC ACCAGGTAG-3' (SEQ ID NO: 37)

2.1.1.3 Construction of pVD214

To construct pVD214 the Rep sequence was amplified from pVD142-selectEP-EP3 clone 12 (described in example 1) using primerset pr460/pr463. Plasmid pVD88 digested with PpuMI*XbaI was used as the vector. The reverse primer pr463 sequence contains the XbaI restriction site (underlined): 5'-CATCACTCTAGAATCACT CTAAACAGTCTTTCTGTC-3' (SEQ ID NO: 38)

2.1.1.3 Construction of pVD228

The Rep68/ACG sequence that is present in pVD228 was generated using primerset pr460/pr487 and pVD88 as template. The PCR fragment was digested with PpuMI and XbaI and cloned in pVD88 digested with the same enzymes resulting in pVD228. Primer pr487 consists of three parts, i.e. an additional sequence which contains an XbaI restriction site (underlined), the 25 bp unique sequence for Rep68 (bold), and the sequence which is homologous with Rep78 (italic): 5'-CATCACTCTAGATTATCAG AGAGAGTGTCCTCGAGCCAATCTGTCTGC GTAGTT-GATCG-3' (SEQ ID NO: 39)

2.1.2 Generation of Recombinant Rep Baculoviruses

Recombinant baculoviruses were generated by co-transfecting Sf9 with one of the different transfer plasmids (i.e. pVD210-212, pVD214-220 and pVD228) and BacPSC1 viral DNA (Protein Sciences). Five days after transfection, the culture medium was harvested and a plaque assay was performed. After 10 days of incubation, recombinant plaques were amplified to p1 and ORF/Rep ratios were determined with Q-PCR method. Correct clones which have an ORF/Rep around 1 were amplified to p2. The amplification of recombinant baculoviruses (p2, p3 and p4) were performed in expresSF+ cells (Protein Sciences, cat no 1000) under serum free conditions.

2.1.3 rAAV5 Productions

To test the different Rep constructs rAAV5 productions were performed in expresSF+ cells using the baculoviruses Bac.Rep:Bac.VD179:Bac.VD92. The baculovirus stock Bac.VD179 contains the SEAP reporter gene under control of the CMV promoter and is flanked by viral AAV2 ITRs. Bac.VD92 contains the AAV5 capsid gene coding for VP1, VP2 and VP3, under control of the Polh promoter. Each production is performed in duplo, repeated three times and compared to the control production with Bac.VD88. The rAAV5 virus titers were measured in the clarified crude lysate using a CMV-Q-PCR method. To isolate intact rAAV5 particles from the crude lysate batch affinity purifications were performed using the AVB Sepharose HP resin. Finally, the eluate was aliquoted and stored at −20° C.

2.1.4 Transgene Replication Assay

Low-molecular weight DNA was isolated from infected expresSF+ cells during rAAV5 productions according to a modified protocol published by Ziegler et al. (Ziegler, K., T. Bui, R. J. Frisque, A. Grandinetti, and V. R. Nerurkar. 2004. A rapid in vitro polyomavirus DNA replication assay. J. Virol. Methods 122:123-127) and using the GenElute plasmid miniprep kit (Sigma-Aldrich). Briefly, 500 µl cell suspension was centrifuged at 12000 g for 1 min. The cell pellet was resuspended in 200 µl Resuspension Solution. Cells were lysed in 200 µl Lysis Solution and incubated at RT for 5 min. Subsequently, 3 µl Proteinase K solution (20 mg/ml) was added and incubated at 55° C. for 30 min. Samples were neutralized by adding 380 µl Neutralization/Binding Solution and incubated on ice for 5 min. After centrifugation at 12000 g for 10 min supernatants were brought on prepared columns and centrifuged at 12000 g for 1 min. Columns were washed with 750 µl Wash Solution and centrifuged twice at 12000 g for 1 min. DNA was eluted in 50 µl 10 mM Tris-HCl (pH8.0) and 2 µl of each sample was separated on a 1% agarose gel containing ethidium bromide.

2.1.5 Western Blot Analyses of Rep Proteins

To the Rep protein expression derived from different Rep baculovirus constructs during rAAV5 production, cell lysates were taken and subjected to western blot analyses. In brief, 450 µl was taken from a production 24 h post infection (p.i.), 50 µl 10× lysis buffer and 8 µl Benzonase (diluted to 2.5 U/µl in PBS; Merck, cat no 1.01697.0001) was added. After mixing, the samples were incubated for 45 min on ice. Lysates were centrifuged at 1900 g and 300 uL of the supernatant was mixed with 100 uL 4× NuPage sample buffer containing 200 mM DTT. The samples were incubated at 95° C. for 5 minutes and stored at −20° C. Proteins were separated on a 4-12% Bis-Tris NuPAGE gel (Invitrogen, cat no NP0323BOX) and the proteins were thereafter blotted on a PVDF membrane. First antibody incubation was done with anti-Rep 303.9 antibody (dilution 1:500; Progen, cat. no. #65169). Polyclonal rabbit anti-mouse IgG-HRP (DAKO, cat no P0260) was used as the secondary antibody in a 1:1000 dilution. After three washes with TBS-T the membrane was incubated with 500 µl Lumi-Light plus substrate solution (Roche, cat no 12015196001) for 1-5 min. Subsequently, the chemiluminescent signal was detected with the Image Quant 400.

2.1.6 Residual Baculovirus DNA Analysis

Residual baculovirus DNA impurities present in the rAAV5 batch affinity purified samples were analyzed using the Q-PCR method. Total DNA was isolated from the rAAV5 particles and analysed using Q-PCR. Bac.VD43 baculovirus DNA was used as a standard line instead. The CMV primerset to quantify the amount of transgene and the different primersets used to determine the amount of residual baculovirus DNA are the following:

CMV primerset:

Pr59: 5' AATGGGCGGTAGGCGTGTA 3'  (SEQ ID NO: 40)

Pr60: 5' AGGCGATCTGACGGTTCACTAA 3'  (SEQ ID NO: 41)

Baculovirus ORF1629 primerset (595 bp downstream of R-ITR):

Pr180: 5' CGAACCGATGGCTGGACTATC 3'  (SEQ ID NO: 32)

Pr181: 5' TGCTGCTACAAGATTTGGCAAGT 3'  (SEQ ID NO: 33)

Right of baculovirus ORF603 primerset (249 bp upstream of L-ITR):

```
                                            (SEQ ID NO: 42)
Pr406: 5' ACAGCCATTGTAATGAGACGCACAA 3'

(SEQ ID NO: 43)
Pr407: 5' CCTAGCGCCCGATCAGCAACTATAT 3'
```

Baculovirus HR3 region primerset (65 kbp downstream of R-ITR):

```
                                            (SEQ ID NO: 44)
Pr340: 5' ATACAACCGTTGGTTGCACG 3'

(SEQ ID NO: 45)
Pr341: 5' CGGGACACGCCATGTATT 3'
```

Finally, the transgene/residual DNA ratios measured in the different rAAV5 samples were compared to rAAV5 particles produced with Bac.VD88.

2.1.7 Total Particle Assay

The amount of total rAAV5 particles present in the purified batches was determined SyproRuby staining. In brief, equal amounts of each sample were mixed with 4×LDS sample buffer containing 200 mM DTT and heated for 5 min at 90° C. Total protein was stained using Sypro-Ruby and VP3 bands were quantified with the ImageQuantT1 software 1D analysis version 7.0 (GE Healthcare). A rAAV5 control sample with known total particle concentration was taken along on each gel and used to determine to total particle concentration in each sample.

2.1.8 Statistical Analysis

All data are represented as means±S.E.M. and the statistical analyses involved the ANOVA single factor test using Excel 2003. Statistical significance was set at $p<0.05$.

2.2 Results 2.2.1 Rep Expression

Figure 10A:
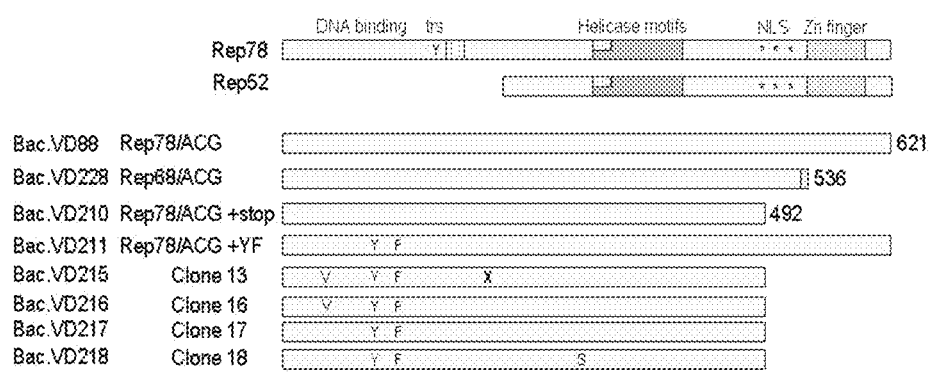
FIGS. 10A and 10B show the Rep protein expression from Rep baculovirus constructs comprising the YF mutations. A) Schematic overview of the different Rep baculovirus constructs comprising the YF mutations and the control constructs Bac.VD88, −228 and −210. Numbers indicate the amino acid numbering according to Rep78. Amino acid changes in the Rep proteins compared to Bac.VD88 are shown in capital letters and the silent mutations (only present in the DNA) are indicated by X. At the upper part a schematic overview of the Rep78 and Rep52 replication proteins is shown which are expressed by Bac.VD88. Functional domains present in the Rep proteins are indicated at the top (Chiorini, J. A., F. Kim, L. Yang, and R. M. Kotin. (1999) J. Virol. 73:1309-1319). Trs, terminal resolution site; NLS, nuclear localization signal; Zn finger, Zinc finger; regions necessary for multimerization are depicted by striped boxes. B) A representative western blot analysis showing the Rep protein expression from the different Rep baculovirus constructs during a rAAV5 production. Protein lysates were harvested 24 h p.i. The shortened Rep forms expressed from Bac.VD210 and Bac.VD215-218 are indicated with arrows and named Reppy78 and Reppy52.
Figure 10B:
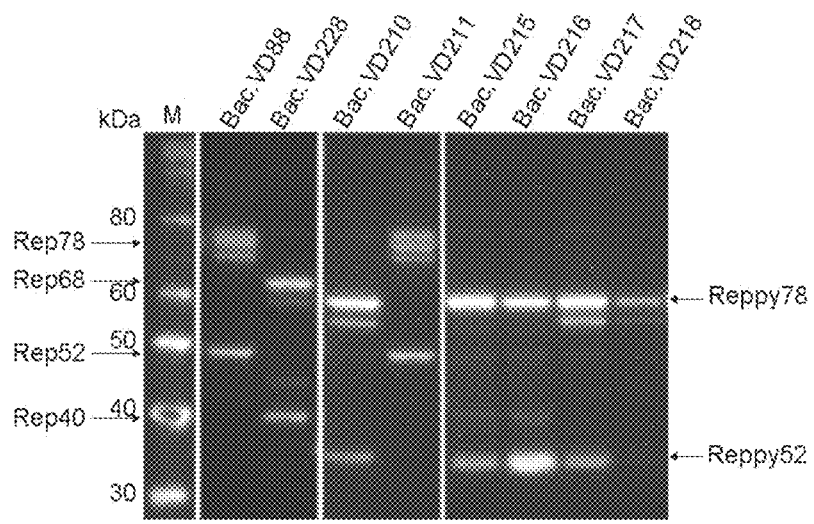
Figure 11A:
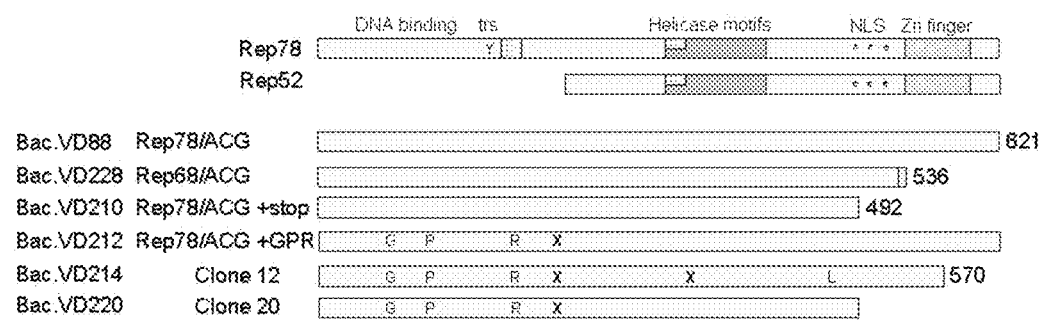
FIGS. 11A and 11B show the Rep protein expression from Rep baculovirus constructs comprising the GPR mutations. A) Schematic overview of the different Rep baculovirus constructs comprising the GPR mutations and the control constructs Bac.VD88, −228 and −210. Numbers indicate the amino acid numbering according to Rep78. Amino acid changes in the Rep proteins compared to Bac.VD88 are shown in capital letters and the silent mutations (only present in the DNA) are indicated by X. At the upper part a schematic overview of the Rep78 and Rep52 replication proteins is shown which are expressed by Bac.VD88. Functional domains present in the Rep proteins are indicated at the top (Chiorini, J. A., F. Kim, L. Yang, and R. M. Kotin. (1999) J. Virol. 73:1309-1319). Trs, terminal resolution site; NLS, nuclear localization signal; Zn finger, Zinc finger; regions necessary for multimerization are depicted by striped boxes. B) A representative western blot analysis showing the Rep protein expression from the different Rep baculovirus constructs during a rAAV5 production. Protein lysates were harvested 24 h p.i. The shortened Rep forms expressed from Bac.VD210, Bac.VD214 and Bac.VD220 are indicated with arrows and named Reppy78 and Reppy52.
Figure 11B:
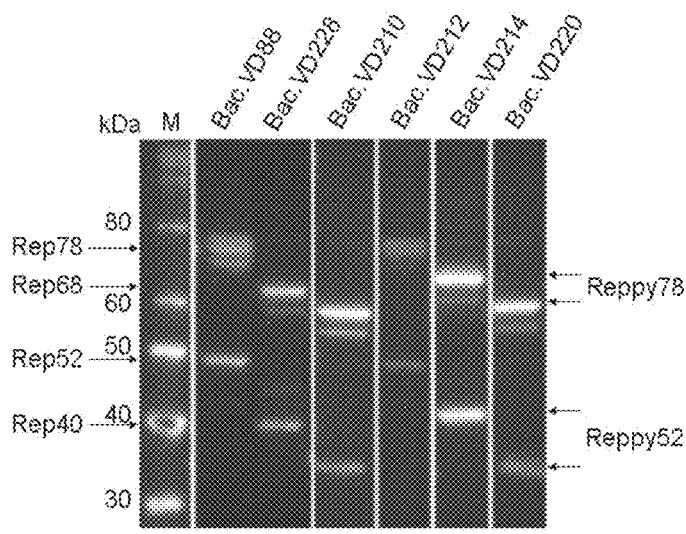

The Rep protein expression from the different Rep baculovirus constructs (FIGS. 10A and 11A) was determined by western blot analysis on lysates obtained 24 h p.i. (FIGS. 10B and 11B). The control construct Bac.VD88 expresses the Rep78 and Rep52 proteins and Bac.VD228 the two shorter Rep proteins Rep68 and Rep40, which lack the C-terminal Zinc-finger domain. The baculoviruses Bac.VD210 and Bac.VD215-218 express shortened Rep78 and Rep52 mutant forms that have a molecular weight of ~60 kDa and ~30 kDa and are indicated with Reppy78 and Reppy52 (FIG. 10B), respectively. Bac.VD211 encodes for the full length Rep proteins and the expression was shown to be comparable to Bac.VD88. Remarkably, all constructs except for Bac.VD215 and Bac.VD216 showed a cross reactive band which is migrating somewhat faster than the full length Rep78 or Reppy78. This could be the result of an alternative translation start site, because in the Rep sequence in Bac.VD215 and Bac.VD216 an ATG (M) was mutated to a GTG (V) and this constructs does not show this cross reactive band. Interestingly, Bac.VD216 expresses more Reppy52 as compared to the other constructs. The Rep expression pattern of Bac.VD212 which encodes for the full length Rep is comparable to Bac.VD88, but the expression levels are lower (FIG. 11B). Bac.VD220 expresses Reppy78 and Reppy52 mutant forms that have the same molecular weight as the ones expressed by Bac.VD210 and −215-218 (see FIG. 10B), while the shortened Rep proteins expressed by Bac.VD214 are larger and migrate at the expected sizes of ~65 kDa and ~39 kDa.

2.2.2 Transgene Replication

Figure 12A:
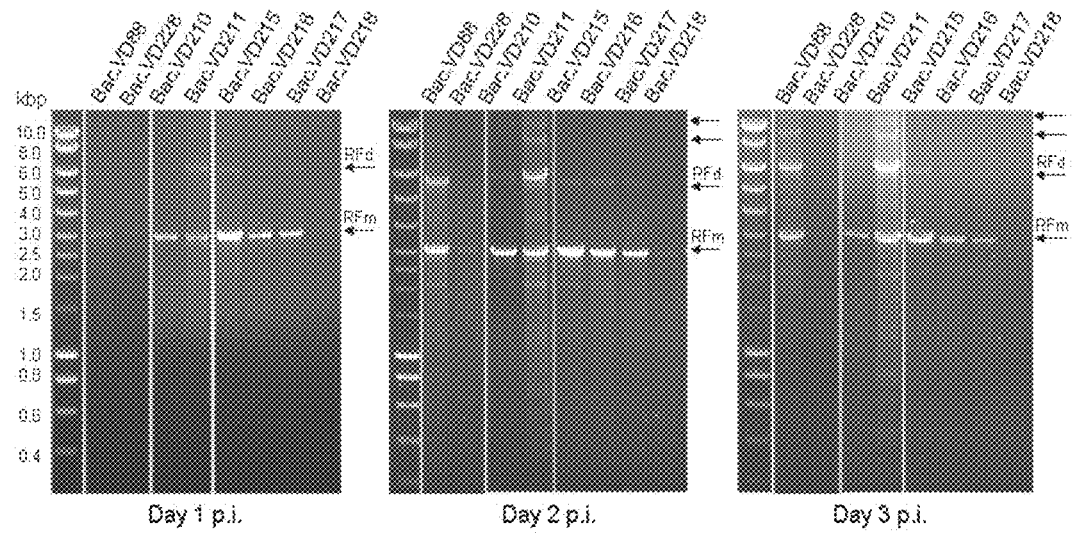
FIGS. 12A and 12B show the CMV-SEAP transgene replication during rAAV5 production using the different Rep baculovirus constructs. Representative agarose gels showing the LMW-DNA isolated from rAAV5 productions using the Rep baculovirus constructs comprising the YF (A) or GPR (B) mutations and the control constructs. LMW-DNA was isolated from cell pellets that were harvested 1, 2 and 3 days p.i. The monomeric and dimeric replicative forms of the transgene are indicated with RFm and RFd, respectively. Higher order forms are only indicated with arrows.
Figure 12B:
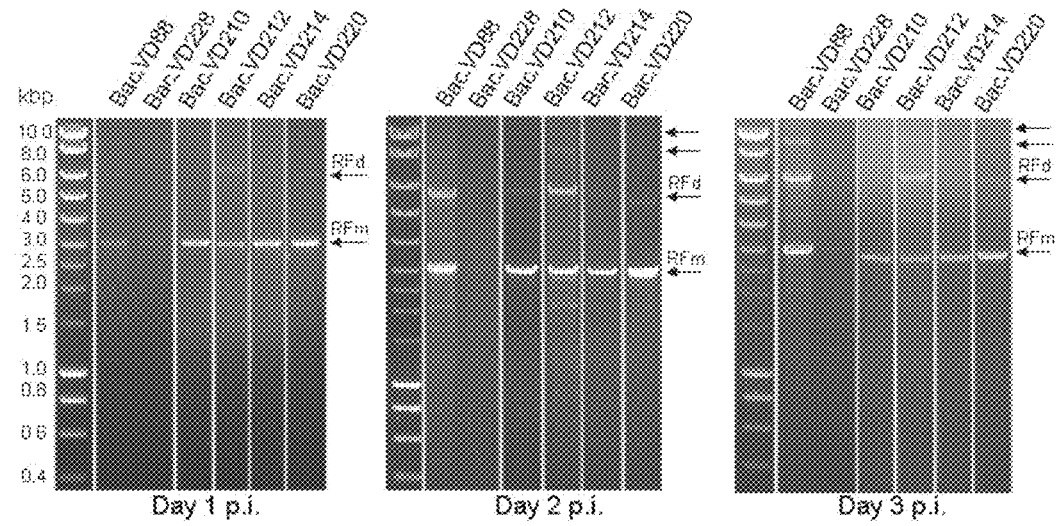

In the BEVS-based rAAV production process the expression of Rep78 is required for replicating the therapeutic gene that is flanked by viral ITRs and has to be packaged into the preformed capsids. The baculoviruses Bac.VD215-218 express the shortened Rep78 proteins which also have 1-3 point mutations in their N-terminal domain. This Rep78-specific part comprises the DNA binding domain and mutations in it could affect the binding to the viral ITRs maybe resulting in altered replication and/or packaging of the transgene. Replicative forms of the transgene can be detected relatively easily in insect cells (Urabe, M., T. Nakakura, K. Q. Xin, Y. Obara, H. Mizukami, A. Kume, R. M. Kotin, and K. Ozawa. (2006) J. Virol. 80:1874-1885) and was therefore being monitored during rAAV5 production. Bac.VD179 that is used in the different experiments comprises the CMV-SEAP transgene and is ~3.1 kbp. To get rid off host cell and baculovirus genomic DNA only low-molecular weight DNA was isolated from cell pellets 1, 2 and 3 days p.i. using a plasmid miniprep kit (Ziegler, K., T. Bui, R. J. Frisque, A. Grandinetti, and V. R. Nerurkar. (2004) J. Virol. Methods 122:123-127). The isolated DNA was separated on agarose gels and visualized using ethidium bromide staining as shown in FIGS. 12A and 12B. One day p.i. the monomeric replicative form of the transgene (RFm) is very well detectable in most productions, except for Bac.VD88, −228 and −218 in which only a very small amount of RFm is present. Also a very faint band of ~6 kbp, which represents the dimeric replicative form (RFd) of the transgene, is present in some productions. At day 2 p.i. (FIGS. 12A and 12B, middle panel) the amount of RFm increased as compared to day 1 and in the productions in which the full length Rep78 is expressed (i.e. Bac.VD88, −211 and −212) the RFd is more abundant as compared to the productions in which Reppy78 is expressed (i.e Bac.VD210 and Bac.VD214-218). The pattern of the replicated DNA at day 3 p.i. is comparable to that at day 2. Remarkably, in the productions with Bac.VD88, Bac.VD211 and Bac.VD212 much more additional bands and smears are present. In Bac.VD228 and −218 only the RFm is present, but hardly detectable as compared to other productions. In conclusion, in the productions in which the full length Rep78 protein is expressed, much more higher order RFs are detectable suggesting that the full length protein replicates the rAAV genome different than the shortened Reppy78 proteins.

2.2.3 rAAV Productions

Figure 13:
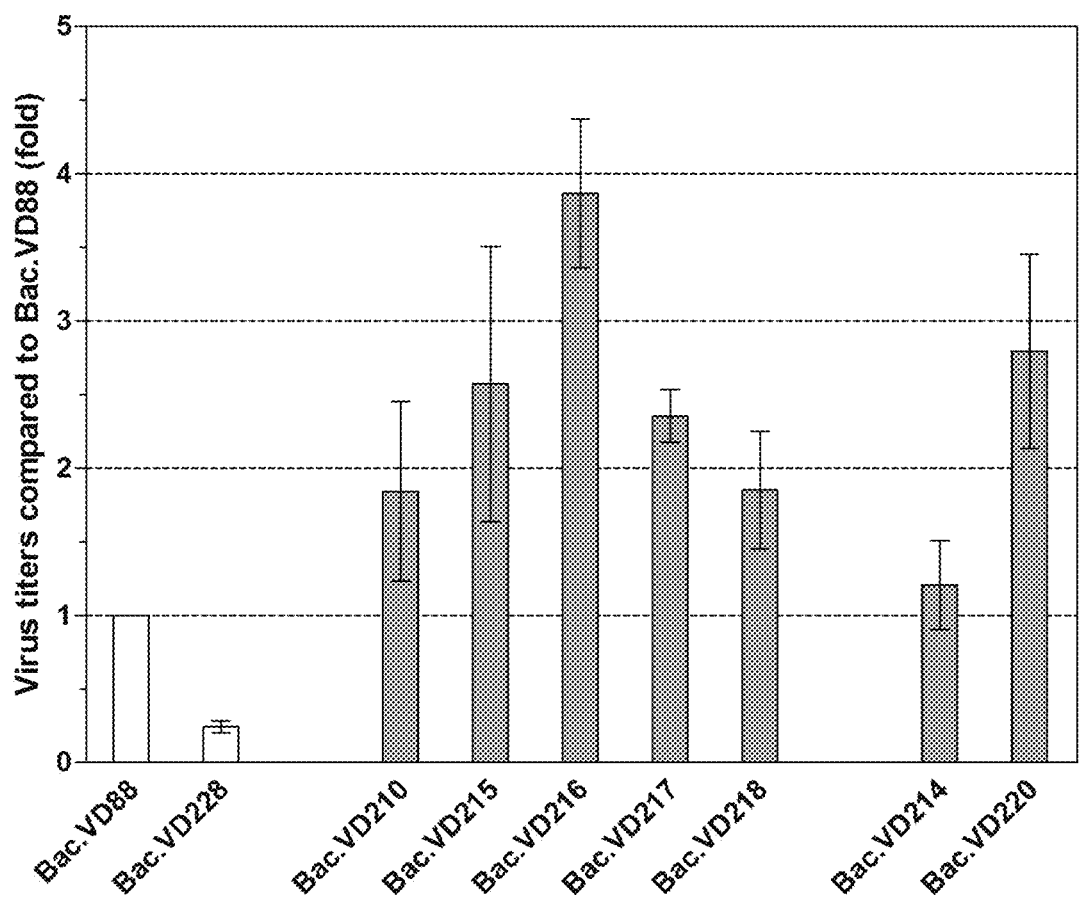
FIG. 13 shows the virus titers of rAAV5 productions performed with the different Rep baculovirus constructs. Virus titers were determined in clarified crude lysates using the CMV Q-PCR method. Productions with Bac.VD216 and Bac.VD217 significantly improved the virus titers, while Bac.VD228 reduced the virus titer. Results are indicated as mean±S.E.M. (n=3) and calculated as fold to Bac.VD88, which was set as 1 in all three experiments.

To determine whether the Rep mutant constructs can improve the production process rAAV5 productions were performed and virus titers were determined in clarified crude lysate using Q-PCR analysis. The virus titers were calculated as the fold difference to the production with Bac.VD88 and the results are shown in FIG. 13. Expression of Rep68/40 during production (i.e. Bac.VD228) results in a significant lower vector yield. Productions performed with Bac.VD210 and Bac.VD218 increase the vector yield with almost a 2-fold as compared to Bac.VD88. Bac.VD217 expresses the YF mutated Reppy78 and Reppy52 and results in a 2-fold higher vector yield. Bac.VD216 increases the vector yield significantly to almost a 4-fold while Bac.VD215 and Bac.VD220 seem to improve it with a 2.5-fold. Rep expression from Bac.VD214 does not increase the vector yield.

2.2.4 Product Quality

In principal, the most interesting Rep mutant constructs increase the vector yield and at the same moment also improve the product quality by reducing the amount of residual baculovirus DNA and the total/full particle ratio.

Figure 14:
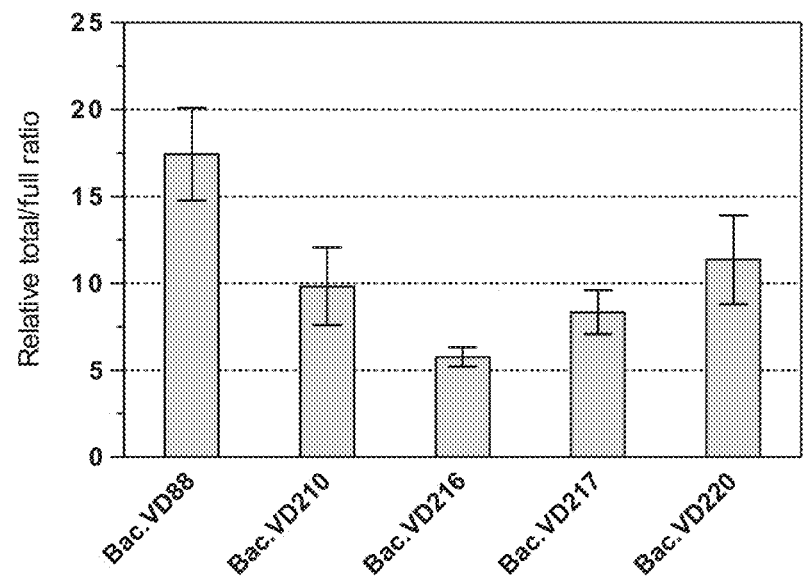
FIG. 14 shows the total/full particle ratio of rAAV5 particles produced with indicated Rep baculovirus constructs. Ratios were determined using SyproRuby staining of total proteins and Q-PCR analysis. Productions with Bac.VD216 and Bac.VD217 significantly improved the total/full ratio. Results are represented as mean±S.E.M and n=6.
Figure 15A:
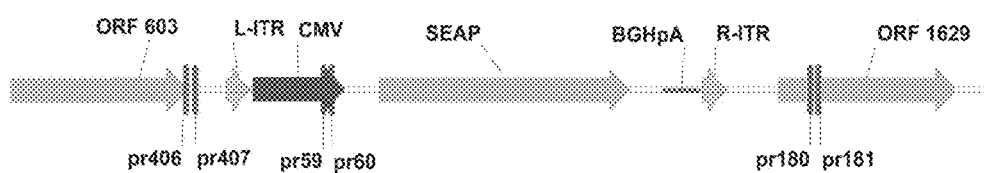
FIGS. 15A, 15B, 15C, and 15D show the amount of residual baculovirus DNA in rAAV5 batch purified samples as ratio from the transgene. A) Schematic overview of the transgene part in baculovirus Bac.VD179 which is flanked by ORF603 and ORF1629 and residual DNA primers that target the left ORF (pr406/407) and the right ORF (pr180/181) are shown in the picture. Primer set pr59/60 targets the CMV promoter and is used to determine the ratio between transgene and residual DNA present in the batches. The HR3 primer set is not shown. B) The amount of residual left ORF DNA determined with pr406/407 is shown as the CMV/left ORF ratio. Productions with Bac.VD210, -217 and -220 resulted in a 3-5 fold reduction of residual DNA in the rAAV5 batches as compared to Bac.VD88. C) The amount of residual right ORF DNA determined with pr180/181 is shown as the CMV/right ORF ratio. All Rep mutant constructs reduce the amount of right ORF residual DNA with a 5-13 fold as compared to Bac.VD88. D) The amount of residual HR3 DNA determined with pr340/341 is shown as the CMV/HR3 ORF ratio. All Rep mutant constructs reduce the amount of HR3 residual DNA with a 25-52 fold. All results are represented as mean±S.E.M and n=6. Statistical analysis involved the ANOVA single factor test and was compared to Bac.VD88. * p<0.05.
Figure 15B:
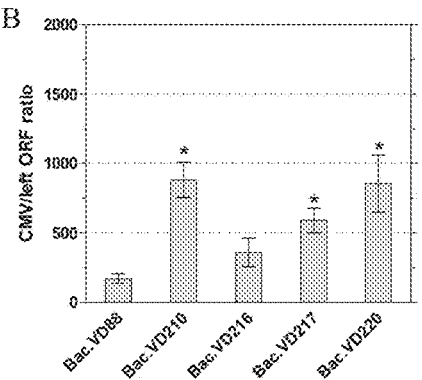
Figure 15C:
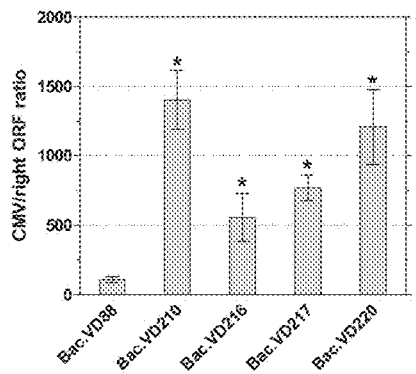
Figure 15D:
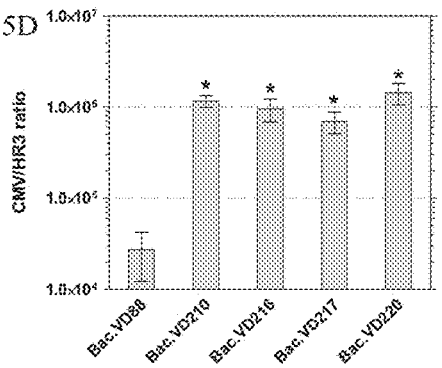
Figure 16G:
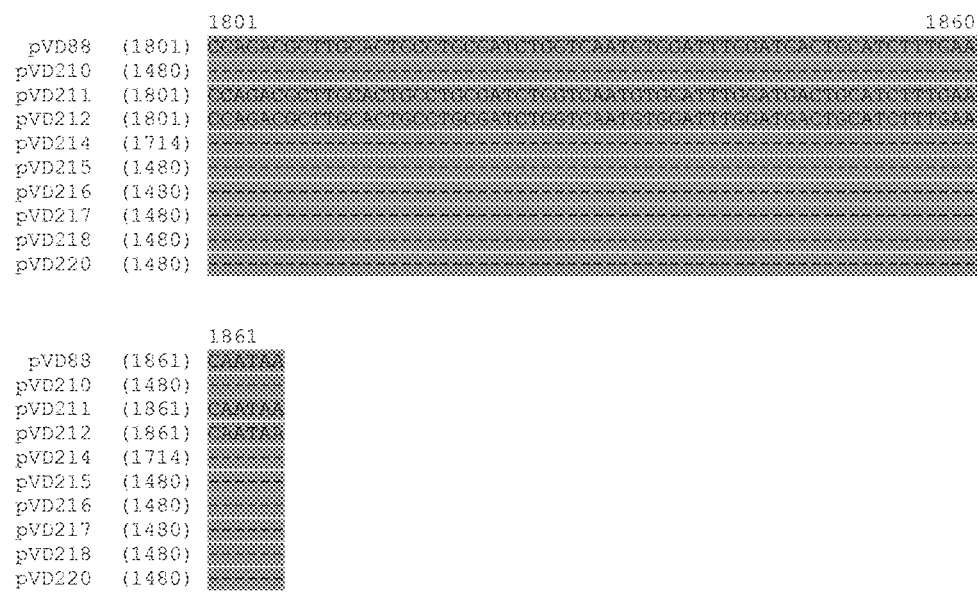

However, these parameters can only accurately be determined in purified batches and therefore the most interesting productions (i.e. Bac.VD88, −210, −216, −217 and −220) were purified using AVB Sepharorse resin. As shown in FIG. 14 productions with Bac.VD216 and Bac.VD217 improved the total/full ratios with a factor 3.0 and 2.1, respectively. In the rAAV5 batches produced with Bac.VD210 and Bac.VD220 the improvement was less pronounced. To determine whether the presence of unwanted baculovirus DNA is decreased in the rAAV5 batches produced with the Rep mutants three different primer sets that each target a different region in the baculovirus genome were used in Q-PCR performed on DNA isolated from the capsids. As shown in FIG. 15A primer set pr406/407 targets a region 249 bp upstream of the L-ITR which is close to baculovirus ORF603, the so-called left ORF. Primer pr180/181 targets a region 595 bp downstream of the R-ITR which is located in ORF1629, the so-called right ORF. The third primer set (not depicted in FIG. 15A) pr340/341 targets a region near HR3 which is located 65 kbp downstream from the R-ITR. This target is hypothesized to be a representative for the complete baculovirus genome that is present as residual DNA in the batches. The amount of residual DNA present in the purified rAAV5 batches are represented as transgene to residual DNA ratios and are shown in FIGS. 15B, 15C and 15D.

Productions with the Rep mutant constructs Bac.VD210, −216, −217 and −220 resulted in a significant reduction of the amount of residual baculovirus DNA in the rAAV5 batches. Batches produced with Bac.VD210 and Bac.VD220 were demonstrated to have a 5-fold reduction in the left ORF DNA, a 13- and 11-fold lower amount of right ORF and a 42- and 52-fold reduction of the HR3 region, respectively. Bac.VD217 also significantly reduces the left and right ORF DNA with a 3- and 7-fold and the HR3 region with a 25-fold. The Rep construct that generates the highest vector yields is Bac.VD216 (FIG. 13), but unfortunately only the right ORF and HR3 region are significantly reduced with a 5- and 35-fold and the left ORF DNA is not.

The invention claimed is:

1. A method for the production of a recombinant Parvoviral virion in an insect cell, which method comprises:
   (a) culturing an insect cell comprising one or more nucleic acid constructs under conditions such that a recombinant Parvoviral virion is produced, wherein the one or more nucleic acid constructs comprise:
      (i) a nucleic acid sequence encoding an adeno-associated virus (AAV) Rep protein comprising a mutation at position 43 of the wild-type Rep sequence of SEQ ID NO: 2, or a corresponding residue in a different wild-type Rep sequence, and being operably linked to an expression control sequence for expression of the AAV Rep protein in an insect cell, wherein at least one of the nuclear localization signals (NLS) of the AAV Rep protein comprises a mutation, thereby reducing the ability of the mutated NLS to function as an NLS;
      (ii) a nucleic acid sequence comprising at least one Parvoviral inverted terminal repeat (ITR) nucleotide sequence; and
      (iii) a nucleic acid sequence encoding a Parvoviral capsid protein operably linked to expression control sequences for expression in an insect cell,
   (b) recovering the recombinant Parvoviral virion.

2. The method of claim 1, wherein the at least one NLS mutation is a truncation or deletion of the at least one NLS of the AAV Rep protein.

3. The method of claim 2, wherein the at least one NLS mutation is a truncation of a nucleic acid sequence encoding the at least one NLS of the AAV Rep protein.

4. The method of claim 2, wherein the at least one NLS mutation is a deletion of a nucleic acid sequence encoding the at least one NLS of the AAV Rep protein.

5. The method of claim 1, wherein the at least one NLS mutation comprises one or more substitutions in a nucleic acid sequence encoding at least one NLS of the AAV Rep protein.

6. The method of claim 5, wherein the at least one NLS mutation results in the substitution of one or more amino acids in at least one NLS of the AAV Rep protein relative to a wild-type NLS amino acid nos. 484-491, 492-494 and 506-509 of SEQ ID NO: 2.

7. The method of claim 5, wherein the at least one NLS mutation results in the truncation of at least one NLS of the AAV Rep protein.

8. The method of claim 5, wherein the at least one NLS mutation results in the deletion of at least one NLS of the AAV Rep protein.

9. The method of claim 1, wherein the AAV Rep protein is an AAV Rep78 protein of SEQ ID NO: 2.

10. The method of claim 9, wherein the at least one NLS is located at amino acids 484-491, 492-494, or 506-509 of SEQ ID NO: 2.

11. The method of claim 10, wherein the at least one NLS is located at amino acids 484-491 of SEQ ID NO: 2 and is truncated or deleted.

12. The method of claim 10, wherein the at least one NLS is located at amino acids 492-494 of SEQ ID NO: 2 and is truncated or deleted.

13. The method of claim 10, wherein the at least one NLS is located at amino acids 506-509 of SEQ ID NO: 2 and is truncated or deleted.

14. The method of claim 9, further comprising at least one substitution mutation in the amino acid residues 57, 97, or 179 of the AAV Rep protein of SEQ ID NO: 2.

15. The method of claim 1, wherein two or more NLS are truncated or deleted.

16. The method of claim 1, further comprising a mutation in the zinc finger domain of the AAV Rep protein.

17. The method of claim 16, wherein the mutation in the zinc finger domain reduces the ability of the mutated zinc finger domain to operate as a zinc finger domain.

18. The method of claim 16, wherein the mutation in the zinc finger domain is a truncation or deleting deletion of the zinc finger domain.

19. The method of claim 16, wherein the mutation in the zinc finger domain comprises one or more amino acid substitutions in the zinc finger domain.

20. The method of claim 16, wherein the AAV Rep protein is an AAV Rep78 protein of SEQ ID NO: 2 comprising a mutation in the amino acid at position 43.

21. The method of claim 20, wherein the codon encoding the amino acid at position 493 or 571 of SEQ ID NO: 2 is substituted with a stop codon.

22. The method of claim 20, wherein the zinc finger domain is located at about amino acid 526 to about amino acid 621 of SEQ ID NO: 2.

23. The method of claim 1, wherein the AAV Rep protein encoded by said nucleic acid has at least 80% sequence similarity to SEQ ID NO:2.

24. The method of claim 1, wherein the AAV Rep protein is an AAV Rep78 protein comprising the amino acid sequence of SEQ ID NOs: 10, 12, or 22.

25. The method of claim 1, wherein the one or more nucleic acid constructs are one or more insect cell-compatible vectors.

26. The method of claim 25, wherein the one or more insect-compatible vectors are baculoviral vectors.

27. The method of claim 1, wherein the nucleic acid construct comprising at least one Parvoviral inverted terminal repeat (ITR) nucleotide sequence further comprises at least one nucleotide sequence encoding a gene product of interest.

28. The method of claim 1, wherein the mutation at position 43 is a substitution.

29. The method of claim 1, wherein the Rep protein further comprises mutations in an amino acid residues corresponding to positions 79 and 120 of the wild-type Rep sequence of SEQ ID NO: 2.

* * * * *

SEQUENCE LISTING

```
<160> NUMBER OF SEQ ID NOS: 45

<210> SEQ ID NO 1
<211> LENGTH: 1866
<212> TYPE: DNA
<213> ORGANISM: adeno-associated virus 2
<220> FEATURE:
<221> NAME/KEY: CDS
<222> LOCATION: (1)..(1866)

<400> SEQUENCE: 1 atg ccg ggg ttt tac gag att gtg att aag gtc ccc agc gac ctt gac      48
Met Pro Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttt ctg     192
Glu Gln Ala Pro Leu Thr Val Ala Glu Lys Leu Gln Arg Asp Phe Leu
    50                  55                  60 acg gaa tgg cgc cgt gtg agt aag gcc ccg gag gcc ctt ttc ttt gtg     240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att     336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg     384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160
```

```
acc cag cct gag ctc cag tgg gcg tgg act aat atg gaa cag tat tta    528
Thr Gln Pro Glu Leu Gln Trp Ala Trp Thr Asn Met Glu Gln Tyr Leu
            165                 170                 175 agc gcc tgt ttg aat ctc acg gag cgt aaa cgg ttg gtg gcg cag cat    576
Ser Ala Cys Leu Asn Leu Thr Glu Arg Lys Arg Leu Val Ala Gln His
        180                 185                 190 ctg acg cac gtg tcg cag acg cag gag cag aac aaa gag aat cag aat    624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac    672
Pro Asn Ser Asp Ala Pro Val Ile Arg Ser Lys Thr Ser Ala Arg Tyr
    210                 215                 220 atg gag ctg gtc ggg tgg ctc gtg gac aag ggg att acc tcg gag aag    720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc    768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag    816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag    864
Ile Met Ser Leu Thr Lys Thr Ala Pro Asp Tyr Leu Val Gly Gln Gln
        275                 280                 285 ccc gtg gag gac att tcc agc aat cgg att tat aaa att ttg gaa cta    912
Pro Val Glu Asp Ile Ser Ser Asn Arg Ile Tyr Lys Ile Leu Glu Leu
        290                 295                 300 aac ggg tac gat ccc caa tat gcg gct tcc gtc ttt ctg gga tgg gcc    960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca   1008
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc   1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac   1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc   1152
Cys Val Asp Lys Met Val Ile Trp Trp Glu Glu Gly Lys Met Thr Ala
        370                 375                 380 aag gtc gtg gag tcg gcc aaa gcc att ctc gga gga agc aag gtg cgc   1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg   1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca   1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt   1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag   1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg   1440
Glu Val Lys Asp Phe Phe Arg Trp Ala Lys Asp His Val Val Glu Val
465                 470                 475                 480
```

```
gag cat gaa ttc tac gtc aaa aag ggt gga gcc aag aaa aga ccc gcc     1488
Glu His Glu Phe Tyr Val Lys Lys Gly Gly Ala Lys Lys Arg Pro Ala
            485                 490                 495 ccc agt gac gca gat ata agt gag ccc aaa cgg gtg cgc gag tca gtt     1536
Pro Ser Asp Ala Asp Ile Ser Glu Pro Lys Arg Val Arg Glu Ser Val
        500                 505                 510 gcg cag cca tcg acg tca gac gcg gaa gct tcg atc aac tac gca gac     1584
Ala Gln Pro Ser Thr Ser Asp Ala Glu Ala Ser Ile Asn Tyr Ala Asp
    515                 520                 525 agg tac caa aac aaa tgt tct cgt cac gtg ggc atg aat ctg atg ctg     1632
Arg Tyr Gln Asn Lys Cys Ser Arg His Val Gly Met Asn Leu Met Leu
530                 535                 540 ttt ccc tgc aga caa tgc gag aga atg aat cag aat tca aat atc tgc     1680
Phe Pro Cys Arg Gln Cys Glu Arg Met Asn Gln Asn Ser Asn Ile Cys
545                 550                 555                 560 ttc act cac gga cag aaa gac tgt tta gag tgc ttt ccc gtg tca gaa     1728
Phe Thr His Gly Gln Lys Asp Cys Leu Glu Cys Phe Pro Val Ser Glu
                565                 570                 575 tct caa ccc gtt tct gtc gtc aaa aag gcg tat cag aaa ctg tgc tac     1776
Ser Gln Pro Val Ser Val Val Lys Lys Ala Tyr Gln Lys Leu Cys Tyr
            580                 585                 590 att cat cat atc atg gga aag gtg cca gac gct tgc act gcc tgc gat     1824
Ile His His Ile Met Gly Lys Val Pro Asp Ala Cys Thr Ala Cys Asp
        595                 600                 605 ctg gtc aat gtg gat ttg gat gac tgc atc ttt gaa caa taa             1866
Leu Val Asn Val Asp Leu Asp Asp Cys Ile Phe Glu Gln
    610                 615                 620

<210> SEQ ID NO 2
<211> LENGTH: 621
<212> TYPE: PRT
<213> ORGANISM: adeno-associated virus 2

<400> SEQUENCE: 2

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
```

```
            180                 185                 190
Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605
```

<210> SEQ ID NO 3
<211> LENGTH: 1866
<212> TYPE: DNA
<213> ORGANISM: Artificial Sequence
<220> FEATURE:
<223> OTHER INFORMATION: pVD88 variant of Rep78 from AAV2
<220> FEATURE:
<221> NAME/KEY: CDS
<222> LOCATION: (1)..(1866)

<400> SEQUENCE: 3

```
acg gcg ggg ttc tac gag att gtg att aag gtc ccc agc gac ctt gac      48
Thr Ala Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttt ctg     192
Glu Gln Ala Pro Leu Thr Val Ala Glu Lys Leu Gln Arg Asp Phe Leu
    50                  55                  60 acg gaa tgg cgc cgt gtg agt aag gcc ccg gag gcc ctt ttc ttt gtg     240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att     336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg     384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta     528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat     576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat     624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac     672
Pro Asn Ser Asp Ala Pro Val Ile Arg Ser Lys Thr Ser Ala Arg Tyr
    210                 215                 220 atg gag ctg gtc ggg tgg ctc gtg gac aag ggg att acc tcg gag aag     720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc     768
Gln Trp Ile Gln Glu Asp Gln Ala Ser Tyr Ile Ser Phe Asn Ala Ala
```

```
                     245                 250                 255
tcc aac tcg cgg tcc caa atc aag gct gcc ttg gac aat gcg gga aag      816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag      864
Ile Met Ser Leu Thr Lys Thr Ala Pro Asp Tyr Leu Val Gly Gln Gln
                275                 280                 285 ccc gtg gag gac att tcc agc aat cgg att tat aaa att ttg gaa cta      912
Pro Val Glu Asp Ile Ser Ser Asn Arg Ile Tyr Lys Ile Leu Glu Leu
    290                 295                 300 aac ggg tac gat ccc caa tat gcg gct tcc gtc ttt ctg gga tgg gcc      960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca     1008
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc     1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac     1104
Phe Tyr Gly Cys Val Asn Trp Thr Asn Glu Asn Phe Pro Phe Asn Asp
                355                 360                 365 tgt gtc gac aag atg gtg atc tgg tgg gag gag ggg aag atg acc gcc     1152
Cys Val Asp Lys Met Val Ile Trp Trp Glu Glu Gly Lys Met Thr Ala
    370                 375                 380 aag gtc gtg gag tcg gcc aaa gcc att ctc gga gga agc aag gtg cgc     1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg     1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca     1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt     1344
Thr Thr Phe Glu His Gln Gln Pro Leu Gln Asp Arg Met Phe Lys Phe
                435                 440                 445 gaa ctc acc cgc cgt ctg gat cat gac ttt ggg aag gtc acc aag cag     1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg     1440
Glu Val Lys Asp Phe Phe Arg Trp Ala Lys Asp His Val Val Glu Val
465                 470                 475                 480 gag cat gaa ttc tac gtc aaa aag ggt gga gcc aag aaa aga ccc gcc     1488
Glu His Glu Phe Tyr Val Lys Lys Gly Gly Ala Lys Lys Arg Pro Ala
                485                 490                 495 ccc agt gac gca gat ata agt gag ccc aaa cgg gtg cgc gag tca gtt     1536
Pro Ser Asp Ala Asp Ile Ser Glu Pro Lys Arg Val Arg Glu Ser Val
            500                 505                 510 gcg cag cca tcg acg tca gac gcg gaa gct tcg atc aac tac gca gac     1584
Ala Gln Pro Ser Thr Ser Asp Ala Glu Ala Ser Ile Asn Tyr Ala Asp
                515                 520                 525 agg tac caa aac aaa tgt tct cgt cac gtg ggc atg aat ctg atg ctg     1632
Arg Tyr Gln Asn Lys Cys Ser Arg His Val Gly Met Asn Leu Met Leu
    530                 535                 540 ttt ccc tgc aga caa tgc gag aga atg aat cag aat tca aat atc tgc     1680
Phe Pro Cys Arg Gln Cys Glu Arg Met Asn Gln Asn Ser Asn Ile Cys
545                 550                 555                 560 ttc act cac gga cag aaa gac tgt tta gag tgc ttt ccc gtg tca gaa     1728
```

```
                    Phe Thr His Gly Gln Lys Asp Cys Leu Glu Cys Phe Pro Val Ser Glu
                                        565                 570                 575 tct caa ccc gtt tct gtc gtc aaa aag gcg tat cag aaa ctg tgc tac                    1776
Ser Gln Pro Val Ser Val Val Lys Lys Ala Tyr Gln Lys Leu Cys Tyr
                580                 585                 590 att cat cat atc atg gga aag gtg cca gac gct tgc act gcc tgc gat                    1824
Ile His His Ile Met Gly Lys Val Pro Asp Ala Cys Thr Ala Cys Asp
                595                 600                 605 ctg gtc aat gtg gat ttg gat gac tgc atc ttt gaa caa taa                            1866
Leu Val Asn Val Asp Leu Asp Asp Cys Ile Phe Glu Gln
                610                 615                 620

<210> SEQ ID NO 4
<211> LENGTH: 621
<212> TYPE: PRT
<213> ORGANISM: Artificial Sequence
<220> FEATURE:
<223> OTHER INFORMATION: Synthetic Construct

<400> SEQUENCE: 4

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285
```

```
Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
610                 615                 620

<210> SEQ ID NO 5
<211> LENGTH: 1479
<212> TYPE: DNA
<213> ORGANISM: Artificial Sequence
<220> FEATURE:
<223> OTHER INFORMATION: pVD210 variant of Rep78 from AAV2
<220> FEATURE:
<221> NAME/KEY: CDS
<222> LOCATION: (1)..(1479)

<400> SEQUENCE: 5 acg gcg ggg ttc tac gag att gtg att aag gtc ccc agc gac ctt gac    48
Thr Ala Gly Phe Tyr Glu Ile Val Ile Lys Val Pro Ser Asp Leu Asp
1               5                   10                  15
```

```
gag cat ctg ccc ggc att tct gac agc ttt gtg aac tgg gtg gcc gag    96
Glu His Leu Pro Gly Ile Ser Asp Ser Phe Val Asn Trp Val Ala Glu
         20                  25                  30 aag gaa tgg gag ttg ccg cca gat tct gac atg gat ctg aat ctg att   144
Lys Glu Trp Glu Leu Pro Pro Asp Ser Asp Met Asp Leu Asn Leu Ile
         35                  40                  45 gag cag gca ccc ctg acc gtg gcc gag aag ctg cag cgc gac ttt ctg   192
Glu Gln Ala Pro Leu Thr Val Ala Glu Lys Leu Gln Arg Asp Phe Leu
 50                  55                  60 acg gaa tgg cgc cgt gtg agt aag gcc ccg gag gcc ctt ttc ttt gtg   240
Thr Glu Trp Arg Arg Val Ser Lys Ala Pro Glu Ala Leu Phe Phe Val
 65                  70                  75                  80 caa ttt gag aag gga gag agc tac ttc cac atg cac gtg ctc gtg gaa   288
Gln Phe Glu Lys Gly Glu Ser Tyr Phe His Met His Val Leu Val Glu
                 85                  90                  95 acc acc ggg gtg aaa tcc atg gtt ttg gga cgt ttc ctg agt cag att   336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg   384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg   432
Pro Asn Trp Phe Ala Val Thr Lys Thr Arg Asn Gly Ala Gly Gly Gly
130                 135                 140 aac aag gtg gtg gat gag tgc tac atc ccc aat tac ttg ctc ccc aaa   480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta   528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat   576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat   624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac   672
Pro Asn Ser Asp Ala Pro Val Ile Arg Ser Lys Thr Ser Ala Arg Tyr
210                 215                 220 atg gag ctg gtc ggg tgg ctc gtg gac aag ggg att acc tcg gag aag   720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc   768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag   816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag   864
Ile Met Ser Leu Thr Lys Thr Ala Pro Asp Tyr Leu Val Gly Gln Gln
        275                 280                 285 ccc gtg gag gac att tcc agc aat cgg att tat aaa att ttg gaa cta   912
Pro Val Glu Asp Ile Ser Ser Asn Arg Ile Tyr Lys Ile Leu Glu Leu
290                 295                 300 aac ggg tac gat ccc caa tat gcg gct tcc gtc ttt ctg gga tgg gcc   960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca  1008
Thr Lys Lys Phe Gly Lys Arg Asn Thr Ile Trp Leu Phe Gly Pro Ala
```

|  |  |  |  |  |  |  |  |  |  |  |  |  |  |  |  |
|---|---|---|---|---|---|---|---|---|---|---|---|---|---|---|---|

```
                    325                 330                 335
act acc ggg aag acc aac atc gcg gag gcc ata gcc cac act gtg ccc      1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac      1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc      1152
Cys Val Asp Lys Met Val Ile Trp Trp Glu Glu Gly Lys Met Thr Ala
    370                 375                 380 aag gtc gtg gag tcg gcc aaa gcc att ctc gga gga agc aag gtg cgc      1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg      1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca      1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt      1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag      1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg      1440
Glu Val Lys Asp Phe Phe Arg Trp Ala Lys Asp His Val Val Glu Val
465                 470                 475                 480 gag cat gaa ttc tac gtc aaa aag ggt gga gcc aag taa                  1479
Glu His Glu Phe Tyr Val Lys Lys Gly Gly Ala Lys
                485                 490

<210> SEQ ID NO 6
<211> LENGTH: 492
<212> TYPE: PRT
<213> ORGANISM: Artificial Sequence
<220> FEATURE:
<223> OTHER INFORMATION: Synthetic Construct

<400> SEQUENCE: 6

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140
```

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
            165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys
                485                 490

<210> SEQ ID NO 7
<211> LENGTH: 1866
<212> TYPE: DNA
<213> ORGANISM: Artificial Sequence
<220> FEATURE:
<223> OTHER INFORMATION: pVD211 variant of Rep78 from AAV2
<220> FEATURE:
<221> NAME/KEY: CDS
<222> LOCATION: (1)..(1866)

<400> SEQUENCE: 7

```
acg gcg ggg ttc tac gag att gtg att aag gtc ccc agc gac ctt gac        48
Thr Ala Gly Phe Tyr Glu Ile Val Ile Lys Val Pro Ser Asp Leu Asp
 1               5                  10                  15 gag cat ctg ccc ggc att tct gac agc ttt gtg aac tgg gtg gcc gag        96
Glu His Leu Pro Gly Ile Ser Asp Ser Phe Val Asn Trp Val Ala Glu
             20                  25                  30 aag gaa tgg gag ttg ccg cca gat tct gac atg gat ctg aat ctg att       144
Lys Glu Trp Glu Leu Pro Pro Asp Ser Asp Met Asp Leu Asn Leu Ile
         35                  40                  45 gag cag gca ccc ctg acc gtg gcc gag aag ctg cag cgc gac ttt ctg       192
Glu Gln Ala Pro Leu Thr Val Ala Glu Lys Leu Gln Arg Asp Phe Leu
     50                  55                  60 acg gaa tgg cgc cgt gtg agt aag gcc ccg gag gcc ctt ttc tat gtg       240
Thr Glu Trp Arg Arg Val Ser Lys Ala Pro Glu Ala Leu Phe Tyr Val
 65                  70                  75                  80 caa ttt gag aag gga gag agc tac ttc cac atg cac gtg ctc gtg gaa       288
Gln Phe Glu Lys Gly Glu Ser Tyr Phe His Met His Val Leu Val Glu
                 85                  90                  95 acc acc ggg gtg aaa tcc atg gtt ttg gga cgt ttc ctg agt cag att       336
Thr Thr Gly Val Lys Ser Met Val Leu Gly Arg Phe Leu Ser Gln Ile
            100                 105                 110 cgc gaa aaa ctg att cag aga ttt tac cgc ggg atc gag ccg act ttg       384
Arg Glu Lys Leu Ile Gln Arg Phe Tyr Arg Gly Ile Glu Pro Thr Leu
        115                 120                 125 cca aac tgg ttc gcg gtc aca aag acc aga aat ggc gcc gga ggc ggg       432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa       480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta       528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat       576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat       624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac       672
Pro Asn Ser Asp Ala Pro Val Ile Arg Ser Lys Thr Ser Ala Arg Tyr
    210                 215                 220 atg gag ctg gtc ggg tgg ctc gtg gac aag ggg att acc tcg gag aag       720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc       768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag       816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag       864
Ile Met Ser Leu Thr Lys Thr Ala Pro Asp Tyr Leu Val Gly Gln Gln
        275                 280                 285 ccc gtg gag gac att tcc agc aat cgg att tat aaa att ttg gaa cta       912
Pro Val Glu Asp Ile Ser Ser Asn Arg Ile Tyr Lys Ile Leu Glu Leu
    290                 295                 300 aac ggg tac gat ccc caa tat gcg gct tcc gtc ttt ctg gga tgg gcc       960
Asn Gly Tyr Asp Pro Gln Tyr Ala Ala Ser Val Phe Leu Gly Trp Ala
305                 310                 315                 320
```

```
acg aaa aag ttc ggc aag agg aac acc atc tgg ctg ttt ggg cct gca    1008
Thr Lys Lys Phe Gly Lys Arg Asn Thr Ile Trp Leu Phe Gly Pro Ala
            325                 330                 335 act acc ggg aag acc aac atc gcg gag gcc ata gcc cac act gtg ccc    1056
Thr Thr Gly Lys Thr Asn Ile Ala Glu Ala Ile Ala His Thr Val Pro
        340                 345                 350 ttc tac ggg tgc gta aac tgg acc aat gag aac ttt ccc ttc aac gac    1104
Phe Tyr Gly Cys Val Asn Trp Thr Asn Glu Asn Phe Pro Phe Asn Asp
    355                 360                 365 tgt gtc gac aag atg gtg atc tgg tgg gag gag ggg aag atg acc gcc    1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc    1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg    1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca    1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt    1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag    1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg    1440
Glu Val Lys Asp Phe Phe Arg Trp Ala Lys Asp His Val Val Glu Val
465                 470                 475                 480 gag cat gaa ttc tac gtc aaa aag ggt gga gcc aag aaa aga ccc gcc    1488
Glu His Glu Phe Tyr Val Lys Lys Gly Gly Ala Lys Lys Arg Pro Ala
                485                 490                 495 ccc agt gac gca gat ata agt gag ccc aaa cgg gtg cgc gag tca gtt    1536
Pro Ser Asp Ala Asp Ile Ser Glu Pro Lys Arg Val Arg Glu Ser Val
            500                 505                 510 gcg cag cca tcg acg tca gac gcg gaa gct tcg atc aac tac gca gac    1584
Ala Gln Pro Ser Thr Ser Asp Ala Glu Ala Ser Ile Asn Tyr Ala Asp
        515                 520                 525 agg tac caa aac aaa tgt tct cgt cac gtg ggc atg aat ctg atg ctg    1632
Arg Tyr Gln Asn Lys Cys Ser Arg His Val Gly Met Asn Leu Met Leu
    530                 535                 540 ttt ccc tgc aga caa tgc gag aga atg aat cag aat tca aat atc tgc    1680
Phe Pro Cys Arg Gln Cys Glu Arg Met Asn Gln Asn Ser Asn Ile Cys
545                 550                 555                 560 ttc act cac gga cag aaa gac tgt tta gag tgc ttt ccc gtg tca gaa    1728
Phe Thr His Gly Gln Lys Asp Cys Leu Glu Cys Phe Pro Val Ser Glu
                565                 570                 575 tct caa ccc gtt tct gtc gtc aaa aag gcg tat cag aaa ctg tgc tac    1776
Ser Gln Pro Val Ser Val Val Lys Lys Ala Tyr Gln Lys Leu Cys Tyr
            580                 585                 590 att cat cat atc atg gga aag gtg cca gac gct tgc act gcc tgc gat    1824
Ile His His Ile Met Gly Lys Val Pro Asp Ala Cys Thr Ala Cys Asp
        595                 600                 605 ctg gtc aat gtg gat ttg gat gac tgc atc ttt gaa caa taa            1866
Leu Val Asn Val Asp Leu Asp Asp Cys Ile Phe Glu Gln
    610                 615                 620

<210> SEQ ID NO 8
```

<211> LENGTH: 621
<212> TYPE: PRT
<213> ORGANISM: Artificial Sequence
<220> FEATURE:
<223> OTHER INFORMATION: Synthetic Construct

<400> SEQUENCE: 8

```
Thr Ala Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Tyr Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Phe Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
```

```
Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
    610                 615                 620

<210> SEQ ID NO 9
<211> LENGTH: 1866
<212> TYPE: DNA
<213> ORGANISM: Artificial Sequence
<220> FEATURE:
<223> OTHER INFORMATION: pVD212 variant of Rep78 from AAV2
<220> FEATURE:
<221> NAME/KEY: CDS
<222> LOCATION: (1)..(1866)

<400> SEQUENCE: 9 acg gcg ggg ttc tac gag att gtg att aag gtc ccc agc gac ctt gac      48
Thr Ala Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
        35                  40                  45 gag cag gca ccc ctg acc gtg gcc ggg aag ctg cag cgc gac ttt ctg     192
Glu Gln Ala Pro Leu Thr Val Ala Gly Lys Leu Gln Arg Asp Phe Leu
    50                  55                  60 acg gaa tgg cgc cgt gtg agt aag gcc ccg gag gcc ctt ttc ttt gtg     240
Thr Glu Trp Arg Arg Val Ser Lys Ala Pro Glu Ala Leu Phe Phe Val
65                  70                  75                  80
```

-continued

| | |
|---|---|
| caa ttt gag aag gga gag agc tac ttc cac atg cac gtg ctc gtg gaa<br>Gln Phe Glu Lys Gly Glu Ser Tyr Phe His Met His Val Leu Val Glu<br>                85                        90                        95 | 288 |
| ccc acc ggg gtg aaa tcc atg gtt ttg gga cgt ttc ctg agt cag att<br>Pro Thr Gly Val Lys Ser Met Val Leu Gly Arg Phe Leu Ser Gln Ile<br>                    100                      105                      110 | 336 |
| cgc gaa aaa ctg att cag aga att tac cgc ggg atc gag ccg act ttg<br>Arg Glu Lys Leu Ile Gln Arg Ile Tyr Arg Gly Ile Glu Pro Thr Leu<br>        115                      120                      125 | 384 |
| cca aac tgg ttc gcg gtc aca aag acc aga aat ggc gcc gga ggc ggg<br>Pro Asn Trp Phe Ala Val Thr Lys Thr Arg Asn Gly Ala Gly Gly Gly<br>130                      135                      140 | 432 |
| aac aag gtg gtg gat gag tgc tac atc ccc aat tac ttg ctc ccc aaa<br>Asn Lys Val Val Asp Glu Cys Tyr Ile Pro Asn Tyr Leu Leu Pro Lys<br>145                      150                      155                      160 | 480 |
| acc cag cct gag ctc cag tgg gcg tgg act aat atg gaa cag tat tta<br>Thr Gln Pro Glu Leu Gln Trp Ala Trp Thr Asn Met Glu Gln Tyr Leu<br>                165                      170                      175 | 528 |
| agc gcc cgt ttg aat ctc acg gag cgt aaa cgg ttg gtg gcg cag cat<br>Ser Ala Arg Leu Asn Leu Thr Glu Arg Lys Arg Leu Val Ala Gln His<br>        180                      185                      190 | 576 |
| ctg acg cac gtg tcg cag acg cag gag cag aac aaa gag aat cag aat<br>Leu Thr His Val Ser Gln Thr Gln Glu Gln Asn Lys Glu Asn Gln Asn<br>                195                      200                      205 | 624 |
| ccc aat tct gat gcg cct gtg atc aga tca aaa act tca gcc agg tac<br>Pro Asn Ser Asp Ala Pro Val Ile Arg Ser Lys Thr Ser Ala Arg Tyr<br>210                      215                      220 | 672 |
| atg gag ctg gtc ggg tgg ctc gtg gac aag ggg att acc tcg gag aag<br>Met Glu Leu Val Gly Trp Leu Val Asp Lys Gly Ile Thr Ser Glu Lys<br>225                      230                      235                      240 | 720 |
| cag tgg atc cag gag gac cag gcc tca tac atc tcc ttc aat gcg gcc<br>Gln Trp Ile Gln Glu Asp Gln Ala Ser Tyr Ile Ser Phe Asn Ala Ala<br>                    245                      250                      255 | 768 |
| tcc aac tcg cgg tcc caa atc aag gct gcc ttg gac aat gcg gga aag<br>Ser Asn Ser Arg Ser Gln Ile Lys Ala Ala Leu Asp Asn Ala Gly Lys<br>        260                      265                      270 | 816 |
| att atg agc ctg act aaa acc gcc ccc gac tac ctg gtg ggc cag cag<br>Ile Met Ser Leu Thr Lys Thr Ala Pro Asp Tyr Leu Val Gly Gln Gln<br>                275                      280                      285 | 864 |
| ccc gtg gag gac att tcc agc aat cgg att tat aaa att ttg gaa cta<br>Pro Val Glu Asp Ile Ser Ser Asn Arg Ile Tyr Lys Ile Leu Glu Leu<br>290                      295                      300 | 912 |
| aac ggg tac gat ccc caa tat gcg gct tcc gtc ttt ctg gga tgg gcc<br>Asn Gly Tyr Asp Pro Gln Tyr Ala Ala Ser Val Phe Leu Gly Trp Ala<br>305                      310                      315                      320 | 960 |
| acg aaa aag ttc ggc aag agg aac acc atc tgg ctg ttt ggg cct gca<br>Thr Lys Lys Phe Gly Lys Arg Asn Thr Ile Trp Leu Phe Gly Pro Ala<br>                    325                      330                      335 | 1008 |
| act acc ggg aag acc aac atc gcg gag gcc ata gcc cac act gtg ccc<br>Thr Thr Gly Lys Thr Asn Ile Ala Glu Ala Ile Ala His Thr Val Pro<br>        340                      345                      350 | 1056 |
| ttc tac ggg tgc gta aac tgg acc aat gag aac ttt ccc ttc aac gac<br>Phe Tyr Gly Cys Val Asn Trp Thr Asn Glu Asn Phe Pro Phe Asn Asp<br>                355                      360                      365 | 1104 |
| tgt gtc gac aag atg gtg atc tgg tgg gag gag ggg aag atg acc gcc<br>Cys Val Asp Lys Met Val Ile Trp Trp Glu Glu Gly Lys Met Thr Ala<br>370                      375                      380 | 1152 |
| aag gtc gtg gag tcg gcc aaa gcc att ctc gga gga agc aag gtg cgc<br>Lys Val Val Glu Ser Ala Lys Ala Ile Leu Gly Gly Ser Lys Val Arg<br>385                      390                      395                      400 | 1200 |

```
gtg gac cag aaa tgc aag tcc tcg gcc cag ata gac ccg act ccc gtg    1248
Val Asp Gln Lys Cys Lys Ser Ser Ala Gln Ile Asp Pro Thr Pro Val
            405                 410                 415 atc gtc acc tcc aac acc aac atg tgc gcc gtg att gac ggg aac tca    1296
Ile Val Thr Ser Asn Thr Asn Met Cys Ala Val Ile Asp Gly Asn Ser
        420                 425                 430 acg acc ttc gaa cac cag cag ccg ttg caa gac cgg atg ttc aaa ttt    1344
Thr Thr Phe Glu His Gln Gln Pro Leu Gln Asp Arg Met Phe Lys Phe
    435                 440                 445 gaa ctc acc cgc cgt ctg gat cat gac ttt ggg aag gtc acc aag cag    1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg    1440
Glu Val Lys Asp Phe Phe Arg Trp Ala Lys Asp His Val Val Glu Val
465                 470                 475                 480 gag cat gaa ttc tac gtc aaa aag ggt gga gcc aag aaa aga ccc gcc    1488
Glu His Glu Phe Tyr Val Lys Lys Gly Gly Ala Lys Lys Arg Pro Ala
                485                 490                 495 ccc agt gac gca gat ata agt gag ccc aaa cgg gtg cgc gag tca gtt    1536
Pro Ser Asp Ala Asp Ile Ser Glu Pro Lys Arg Val Arg Glu Ser Val
            500                 505                 510 gcg cag cca tcg acg tca gac gcg gaa gct tcg atc aac tac gca gac    1584
Ala Gln Pro Ser Thr Ser Asp Ala Glu Ala Ser Ile Asn Tyr Ala Asp
        515                 520                 525 agg tac caa aac aaa tgt tct cgt cac gtg ggc atg aat ctg atg ctg    1632
Arg Tyr Gln Asn Lys Cys Ser Arg His Val Gly Met Asn Leu Met Leu
    530                 535                 540 ttt ccc tgc aga caa tgc gag aga atg aat cag aat tca aat atc tgc    1680
Phe Pro Cys Arg Gln Cys Glu Arg Met Asn Gln Asn Ser Asn Ile Cys
545                 550                 555                 560 ttc act cac gga cag aaa gac tgt tta gag tgc ttt ccc gtg tca gaa    1728
Phe Thr His Gly Gln Lys Asp Cys Leu Glu Cys Phe Pro Val Ser Glu
                565                 570                 575 tct caa ccc gtt tct gtc gtc aaa aag gcg tat cag aaa ctg tgc tac    1776
Ser Gln Pro Val Ser Val Val Lys Lys Ala Tyr Gln Lys Leu Cys Tyr
            580                 585                 590 att cat cat atc atg gga aag gtg cca gac gct tgc act gcc tgc gat    1824
Ile His His Ile Met Gly Lys Val Pro Asp Ala Cys Thr Ala Cys Asp
        595                 600                 605 ctg gtc aat gtg gat ttg gat gac tgc atc ttt gaa caa taa             1866
Leu Val Asn Val Asp Leu Asp Asp Cys Ile Phe Glu Gln
    610                 615                 620

<210> SEQ ID NO 10
<211> LENGTH: 621
<212> TYPE: PRT
<213> ORGANISM: Artificial Sequence
<220> FEATURE:
<223> OTHER INFORMATION: Synthetic Construct

<400> SEQUENCE: 10

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Gly Lys Leu Gln Arg Asp Phe Leu
    50                  55                  60
```

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Pro Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Arg Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala

|  |  | 485 |  |  |  | 490 |  |  |  | 495 |  |
|---|---|---|---|---|---|---|---|---|---|---|---|

Pro Ser Asp Ala Asp Ile Ser Glu Pro Lys Arg Val Arg Glu Ser Val
            500                    505                510

Ala Gln Pro Ser Thr Ser Asp Ala Glu Ala Ser Ile Asn Tyr Ala Asp
           515               520              525

Arg Tyr Gln Asn Lys Cys Ser Arg His Val Gly Met Asn Leu Met Leu
   530                 535                540

Phe Pro Cys Arg Gln Cys Glu Arg Met Asn Gln Asn Ser Asn Ile Cys
545              550                555             560

Phe Thr His Gly Gln Lys Asp Cys Leu Glu Cys Phe Pro Val Ser Glu
           565               570              575

Ser Gln Pro Val Ser Val Val Lys Lys Ala Tyr Gln Lys Leu Cys Tyr
           580               585              590

Ile His His Ile Met Gly Lys Val Pro Asp Ala Cys Thr Ala Cys Asp
        595               600              605

Leu Val Asn Val Asp Leu Asp Asp Cys Ile Phe Glu Gln
   610                 615              620

<210> SEQ ID NO 11
<211> LENGTH: 1713
<212> TYPE: DNA
<213> ORGANISM: Artificial Sequence
<220> FEATURE:
<223> OTHER INFORMATION: pVD214 variant of Rep78 from AAV2
<220> FEATURE:
<221> NAME/KEY: CDS
<222> LOCATION: (1)..(1713)

<400> SEQUENCE: 11

```
acg gcg ggg ttc tac gag att gtg att aag gtc ccc agc gac ctt gac     48
Thr Ala Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag     96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att    144
Lys Glu Trp Glu Leu Pro Pro Asp Ser Asp Met Asp Leu Asn Leu Ile
        35                  40                  45 gag cag gca ccc ctg acc gtg gcc ggg aag ctg cag cgc gac ttt ctg    192
Glu Gln Ala Pro Leu Thr Val Ala Gly Lys Leu Gln Arg Asp Phe Leu
    50                  55                  60 acg gaa tgg cgc cgt gtg agt aag gcc ccg gag gcc ctt ttc ttt gtg    240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa    288
Gln Phe Glu Lys Gly Glu Ser Tyr Phe His Met His Val Leu Val Glu
                85                  90                  95 ccc acc ggg gtg aaa tcc atg gtt ttg gga cgt ttc ctg agt cag att    336
Pro Thr Gly Val Lys Ser Met Val Leu Gly Arg Phe Leu Ser Gln Ile
            100                 105                 110 cgc gaa aaa ctg att cag aga att tac cgc ggg atc gag ccg act ttg    384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg    432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa    480
Asn Lys Val Val Asp Glu Cys Tyr Ile Pro Asn Tyr Leu Leu Pro Lys
145                 150                 155                 160
```

| | |
|---|---|
| acc cag cct gag ctc cag tgg gcg tgg act aat atg gaa cag tat tta<br>Thr Gln Pro Glu Leu Gln Trp Ala Trp Thr Asn Met Glu Gln Tyr Leu<br>                165                              170                        175 | 528 |
| agc gcc cgt ttg aat ctc acg gag cgt aaa cgg ttg gtg gcg cag cat<br>Ser Ala Arg Leu Asn Leu Thr Glu Arg Lys Arg Leu Val Ala Gln His<br>                180                              185                        190 | 576 |
| ctg acg cac gtg tcg cag acg cag gag cag aac aaa gag aat cag aat<br>Leu Thr His Val Ser Gln Thr Gln Glu Gln Asn Lys Glu Asn Gln Asn<br>            195                              200                        205 | 624 |
| ccc aat tct gat gcg cct gtg atc aga tca aaa act tca gcc agg tac<br>Pro Asn Ser Asp Ala Pro Val Ile Arg Ser Lys Thr Ser Ala Arg Tyr<br>      210                              215                        220 | 672 |
| atg gag ctg gtc ggg tgg ctc gtg gac aag ggg att acc tcg gag aag<br>Met Glu Leu Val Gly Trp Leu Val Asp Lys Gly Ile Thr Ser Glu Lys<br>225                              230                            235                    240 | 720 |
| cag tgg atc cag gag gac cag gcc tca tac atc tcc ttc aat gcg gcc<br>Gln Trp Ile Gln Glu Asp Gln Ala Ser Tyr Ile Ser Phe Asn Ala Ala<br>                        245                              250                        255 | 768 |
| tcc aac tcg cgg tcc caa atc aag gct gcc ttg gac aat gcg gga aag<br>Ser Asn Ser Arg Ser Gln Ile Lys Ala Ala Leu Asp Asn Ala Gly Lys<br>                260                              265                        270 | 816 |
| att atg agc ctg act aaa acc gcc ccc gac tac ctg gtg ggc cag cag<br>Ile Met Ser Leu Thr Lys Thr Ala Pro Asp Tyr Leu Val Gly Gln Gln<br>            275                              280                        285 | 864 |
| ccc gtg gag gac att tcc agc aat cgg ata tat aaa att ttg gaa cta<br>Pro Val Glu Asp Ile Ser Ser Asn Arg Ile Tyr Lys Ile Leu Glu Leu<br>      290                              295                        300 | 912 |
| aac ggg tac gat ccc caa tat gcg gct tcc gtc ttt ctg gga tgg gcc<br>Asn Gly Tyr Asp Pro Gln Tyr Ala Ala Ser Val Phe Leu Gly Trp Ala<br>305                              310                            315                    320 | 960 |
| acg aaa aag ttc ggc aag agg aac acc atc tgg ctg ttt ggg cct gca<br>Thr Lys Lys Phe Gly Lys Arg Asn Thr Ile Trp Leu Phe Gly Pro Ala<br>                        325                              330                        335 | 1008 |
| act acc ggg aag acc aac atc gcg gag gcc ata gcc cac act gtg ccc<br>Thr Thr Gly Lys Thr Asn Ile Ala Glu Ala Ile Ala His Thr Val Pro<br>                340                              345                        350 | 1056 |
| ttc tac ggg tgc gta aac tgg acc aat gag aac ttt ccc ttc aac gac<br>Phe Tyr Gly Cys Val Asn Trp Thr Asn Glu Asn Phe Pro Phe Asn Asp<br>            355                              360                        365 | 1104 |
| tgt gtc gac aag atg gtg atc tgg tgg gag gag ggg aag atg acc gcc<br>Cys Val Asp Lys Met Val Ile Trp Trp Glu Glu Gly Lys Met Thr Ala<br>      370                              375                        380 | 1152 |
| aag gtc gtg gag tcg gcc aaa gcc att ctc gga gga agc aag gtg cgc<br>Lys Val Val Glu Ser Ala Lys Ala Ile Leu Gly Gly Ser Lys Val Arg<br>385                              390                            395                    400 | 1200 |
| gtg gac cag aaa tgc aag tcc tcg gcc cag ata gac ccg act ccc gtg<br>Val Asp Gln Lys Cys Lys Ser Ser Ala Gln Ile Asp Pro Thr Pro Val<br>                        405                              410                        415 | 1248 |
| atc gtc acc tcc aac acc aac atg tgc gcc gtg att gac ggg aac tca<br>Ile Val Thr Ser Asn Thr Asn Met Cys Ala Val Ile Asp Gly Asn Ser<br>                420                              425                        430 | 1296 |
| acg acc ttc gaa cac cag cag ccg ttg caa gac cgg atg ttc aaa ttt<br>Thr Thr Phe Glu His Gln Gln Pro Leu Gln Asp Arg Met Phe Lys Phe<br>            435                              440                        445 | 1344 |
| gaa ctc acc cgc cgt ctg gat cat gac ttt ggg aag gtc acc aag cag<br>Glu Leu Thr Arg Arg Leu Asp His Asp Phe Gly Lys Val Thr Lys Gln<br>      450                              455                        460 | 1392 |
| gaa gtc aaa gac ttt ttc cgg tgg gca aag gat cac gtg gtt gag gtg<br>Glu Val Lys Asp Phe Phe Arg Trp Ala Lys Asp His Val Val Glu Val<br>465                              470                            475                    480 | 1440 |

-continued

```
gag cat gaa ctc tac gtc aaa aag ggt gga gcc aag aaa aga ccc gcc      1488
Glu His Glu Leu Tyr Val Lys Lys Gly Gly Ala Lys Lys Arg Pro Ala
            485                 490                 495 ccc agt gac gca gat ata agt gag ccc aaa cgg gtg cgc gag tca gtt      1536
Pro Ser Asp Ala Asp Ile Ser Glu Pro Lys Arg Val Arg Glu Ser Val
        500                 505                 510 gcg cag cca tcg acg tca gac gcg gaa gct tcg atc aac tac gca gac      1584
Ala Gln Pro Ser Thr Ser Asp Ala Glu Ala Ser Ile Asn Tyr Ala Asp
    515                 520                 525 agg tac caa aac aaa tgt tct cgt cac gtg ggc atg aat ctg atg ctg      1632
Arg Tyr Gln Asn Lys Cys Ser Arg His Val Gly Met Asn Leu Met Leu
530                 535                 540 ttt ccc tgc aga caa tgc gag aga atg aat cag aat tca aat atc tgc      1680
Phe Pro Cys Arg Gln Cys Glu Arg Met Asn Gln Asn Ser Asn Ile Cys
545                 550                 555                 560 ttc act cac gga cag aaa gac tgt tta gag tga                          1713
Phe Thr His Gly Gln Lys Asp Cys Leu Glu
                565                 570
```

<210> SEQ ID NO 12
<211> LENGTH: 570
<212> TYPE: PRT
<213> ORGANISM: Artificial Sequence
<220> FEATURE:
<223> OTHER INFORMATION: Synthetic Construct

<400> SEQUENCE: 12

```
Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Gly Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Pro Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Arg Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240
```

Gln Trp Ile Gln Glu Asp Gln Ala Ser Tyr Ile Ser Phe Asn Ala Ala
                    245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Leu Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu
                565                 570

<210> SEQ ID NO 13
<211> LENGTH: 1479
<212> TYPE: DNA
<213> ORGANISM: Artificial Sequence
<220> FEATURE:
<223> OTHER INFORMATION: pVD215 variant of Rep78 from AAV2
<220> FEATURE:
<221> NAME/KEY: CDS
<222> LOCATION: (1)..(1479)

<400> SEQUENCE: 13 acg gcg ggg ttc tac gag att gtg att aag gtc ccc agc gac ctt gac       48
Thr Ala Gly Phe Tyr Glu Ile Val Ile Lys Val Pro Ser Asp Leu Asp -continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
gag cat ctg ccc ggc att tct gac agc ttt gtg aac tgg gtg gcc gag      96
Glu His Leu Pro Gly Ile Ser Asp Ser Phe Val Asn Trp Val Ala Glu
             20                  25                  30 aag gaa tgg gag ttg ccg cca gat tct gac gtg gat ctg aat ctg att     144
Lys Glu Trp Glu Leu Pro Pro Asp Ser Asp Val Asp Leu Asn Leu Ile
         35                  40                  45 gag cag gca ccc ctg acc gtg gcc gag aag ctg cag cgc gac ttt ctg     192
Glu Gln Ala Pro Leu Thr Val Ala Glu Lys Leu Gln Arg Asp Phe Leu
     50                  55                  60 acg gaa tgg cgc cgt gtg agt aag gcc ccg gag gcc ctt ttc tat gtg     240
Thr Glu Trp Arg Arg Val Ser Lys Ala Pro Glu Ala Leu Phe Tyr Val
 65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                 85                  90                  95 acc acc ggg gtg aaa tcc atg gtt ttg gga cgt ttc ctg agt cag att     336
Thr Thr Gly Val Lys Ser Met Val Leu Gly Arg Phe Leu Ser Gln Ile
             100                 105                 110 cgc gaa aaa ctg att cag aga ttt tac cgc ggg atc gag ccg act ttg     384
Arg Glu Lys Leu Ile Gln Arg Phe Tyr Arg Gly Ile Glu Pro Thr Leu
         115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
     130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta     528
Thr Gln Pro Glu Leu Gln Trp Ala Trp Thr Asn Met Glu Gln Tyr Leu
                 165                 170                 175 agc gcc tgt ttg aat ctc acg gag cgt aaa cgg ttg gtg gcg cag cat     576
Ser Ala Cys Leu Asn Leu Thr Glu Arg Lys Arg Leu Val Ala Gln His
             180                 185                 190 ctg acg cac gtg tcg cag acg cag gag cag aac aaa gag aat cag aat     624
Leu Thr His Val Ser Gln Thr Gln Glu Gln Asn Lys Glu Asn Gln Asn
         195                 200                 205 ccc aat tcc gat gcg ccg gtg atc aga tca aaa act tca gcc agg tac     672
Pro Asn Ser Asp Ala Pro Val Ile Arg Ser Lys Thr Ser Ala Arg Tyr
     210                 215                 220 atg gag ctg gtc ggg tgg ctc gtg gac aag ggg att acc tcg gag aag     720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc     768
Gln Trp Ile Gln Glu Asp Gln Ala Ser Tyr Ile Ser Phe Asn Ala Ala
                 245                 250                 255 tcc aac tcg cgg tcc caa atc aag gct gcc ttg gac aat gcg gga aag     816
Ser Asn Ser Arg Ser Gln Ile Lys Ala Ala Leu Asp Asn Ala Gly Lys
             260                 265                 270 att atg agc ctg act aaa acc gcc ccc gac tac ctg gtg ggc cag cag     864
Ile Met Ser Leu Thr Lys Thr Ala Pro Asp Tyr Leu Val Gly Gln Gln
         275                 280                 285 ccc gtg gag gac att tcc agc aat cgg att tat aaa att ttg gaa cta     912
Pro Val Glu Asp Ile Ser Ser Asn Arg Ile Tyr Lys Ile Leu Glu Leu
     290                 295                 300 aac ggg tac gat ccc caa tat gcg gct tcc gtc ttt ctg gga tgg gcc     960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca    1008
```

```
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc      1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac      1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc      1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc      1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg      1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca      1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt      1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag      1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg      1440
Glu Val Lys Asp Phe Phe Arg Trp Ala Lys Asp His Val Val Glu Val
465                 470                 475                 480 gag cat gaa ttc tac gtc aaa aag ggt gga gcc aag taa                  1479
Glu His Glu Phe Tyr Val Lys Lys Gly Gly Ala Lys
                485                 490

<210> SEQ ID NO 14
<211> LENGTH: 492
<212> TYPE: PRT
<213> ORGANISM: Artificial Sequence
<220> FEATURE:
<223> OTHER INFORMATION: Synthetic Construct

<400> SEQUENCE: 14

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Val Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Tyr Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Ser Gln Ile
            100                 105                 110

Arg Glu Lys Leu Ile Gln Arg Phe Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140
```

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
            165                 170                 175

Ser Ala Cys Leu Asn Leu Thr Glu Arg Lys Arg Leu Val Ala Gln His
        180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
        260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
        340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys
            485                 490

<210> SEQ ID NO 15
<211> LENGTH: 1479
<212> TYPE: DNA
<213> ORGANISM: Artificial Sequence
<220> FEATURE:
<223> OTHER INFORMATION: pVD216 variant of Rep78 from AAV2
<220> FEATURE:
<221> NAME/KEY: CDS
<222> LOCATION: (1)..(1479)

<400> SEQUENCE: 15

-continued

| | | |
|---|---|---|
| acg gcg ggg ttc tac gag att gtg att aag gtc ccc agc gac ctt gac<br>Thr Ala Gly Phe Tyr Glu Ile Val Ile Lys Val Pro Ser Asp Leu Asp<br>1                              5                          10                         15 | 48 |
| gag cat ctg ccc ggc att tct gac agc ttt gtg aac tgg gtg gcc gag<br>Glu His Leu Pro Gly Ile Ser Asp Ser Phe Val Asn Trp Val Ala Glu<br>                    20                          25                         30 | 96 |
| aag gaa tgg gag ttg ccg cca gat tct gac gtg gat ctg aat ctg att<br>Lys Glu Trp Glu Leu Pro Pro Asp Ser Asp Val Asp Leu Asn Leu Ile<br>           35                          40                         45 | 144 |
| gag cag gca ccc ctg acc gtg gcc gag aag ctg cag cgc gac ttt ctg<br>Glu Gln Ala Pro Leu Thr Val Ala Glu Lys Leu Gln Arg Asp Phe Leu<br>50                             55                        60 | 192 |
| acg gaa tgg cgc cgt gtg agt aag gcc ccg gag gcc ctt ttc tat gtg<br>Thr Glu Trp Arg Arg Val Ser Lys Ala Pro Glu Ala Leu Phe Tyr Val<br>65                             70                        75                        80 | 240 |
| caa ttt gag aag gga gag agc tac ttc cac atg cac gtg ctc gtg gaa<br>Gln Phe Glu Lys Gly Glu Ser Tyr Phe His Met His Val Leu Val Glu<br>                             85                         90                        95 | 288 |
| acc acc ggg gtg aaa tcc atg gtt ttg gga cgt ttc ctg agt cag att<br>Thr Thr Gly Val Lys Ser Met Val Leu Gly Arg Phe Leu Ser Gln Ile<br>                    100                        105                       110 | 336 |
| cgc gaa aaa ctg att cag aga ttt tac cgc ggg atc gag ccg act ttg<br>Arg Glu Lys Leu Ile Gln Arg Phe Tyr Arg Gly Ile Glu Pro Thr Leu<br>           115                        120                       125 | 384 |
| cca aac tgg ttc gcg gtc aca aag acc aga aat ggc gcc gga ggc ggg<br>Pro Asn Trp Phe Ala Val Thr Lys Thr Arg Asn Gly Ala Gly Gly Gly<br>130                           135                       140 | 432 |
| aac aag gtg gtg gat gag tgc tac atc ccc aat tac ttg ctc ccc aaa<br>Asn Lys Val Val Asp Glu Cys Tyr Ile Pro Asn Tyr Leu Leu Pro Lys<br>145                           150                       155                      160 | 480 |
| acc cag cct gag ctc cag tgg gcg tgg act aat atg gaa cag tat tta<br>Thr Gln Pro Glu Leu Gln Trp Ala Trp Thr Asn Met Glu Gln Tyr Leu<br>                    165                        170                       175 | 528 |
| agc gcc tgt ttg aat ctc acg gag cgt aaa cgg ttg gtg gcg cag cat<br>Ser Ala Cys Leu Asn Leu Thr Glu Arg Lys Arg Leu Val Ala Gln His<br>                  180                        185                       190 | 576 |
| ctg acg cac gtg tcg cag acg cag gag cag aac aaa gag aat cag aat<br>Leu Thr His Val Ser Gln Thr Gln Glu Gln Asn Lys Glu Asn Gln Asn<br>           195                        200                       205 | 624 |
| ccc aat tct gat gcg ccg gtg atc aga tca aaa act tca gcc agg tac<br>Pro Asn Ser Asp Ala Pro Val Ile Arg Ser Lys Thr Ser Ala Arg Tyr<br>210                           215                       220 | 672 |
| atg gag ctg gtc ggg tgg ctc gtg gac aag ggg att acc tcg gag aag<br>Met Glu Leu Val Gly Trp Leu Val Asp Lys Gly Ile Thr Ser Glu Lys<br>225                           230                       235                   240 | 720 |
| cag tgg atc cag gag gac cag gcc tca tac atc tcc ttc aat gcg gcc<br>Gln Trp Ile Gln Glu Asp Gln Ala Ser Tyr Ile Ser Phe Asn Ala Ala<br>                  245                        250                       255 | 768 |
| tcc aac tcg cgg tcc caa atc aag gct gcc ttg gac aat gcg gga aag<br>Ser Asn Ser Arg Ser Gln Ile Lys Ala Ala Leu Asp Asn Ala Gly Lys<br>           260                        265                       270 | 816 |
| att atg agc ctg act aaa acc gcc ccc gac tac ctg gtg ggc cag cag<br>Ile Met Ser Leu Thr Lys Thr Ala Pro Asp Tyr Leu Val Gly Gln Gln<br>                275                        280                       285 | 864 |
| ccc gtg gag gac att tcc agc aat cgg att tat aaa att ttg gaa cta<br>Pro Val Glu Asp Ile Ser Ser Asn Arg Ile Tyr Lys Ile Leu Glu Leu<br>           290                        295                       300 | 912 |
| aac ggg tac gat ccc caa tat gcg gct tcc gtc ttt ctg gga tgg gcc<br>Asn Gly Tyr Asp Pro Gln Tyr Ala Ala Ser Val Phe Leu Gly Trp Ala | 960 |

```
                       305                 310                 315                 320
acg aaa aag ttc ggc aag agg aac acc atc tgg ctg ttt ggg cct gca      1008
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc      1056
Thr Thr Gly Lys Thr Asn Ile Ala Glu Ala Ile Ala His Thr Val Pro
        340                 345                 350 ttc tac ggg tgc gta aac tgg acc aat gag aac ttt ccc ttc aac gac      1104
Phe Tyr Gly Cys Val Asn Trp Thr Asn Glu Asn Phe Pro Phe Asn Asp
            355                 360                 365 tgt gtc gac aag atg gtg atc tgg tgg gag gag ggg aag atg acc gcc      1152
Cys Val Asp Lys Met Val Ile Trp Trp Glu Glu Gly Lys Met Thr Ala
    370                 375                 380 aag gtc gtg gag tcg gcc aaa gcc att ctc gga gga agc aag gtg cgc      1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg      1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca      1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt      1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag      1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg      1440
Glu Val Lys Asp Phe Phe Arg Trp Ala Lys Asp His Val Val Glu Val
465                 470                 475                 480 gag cat gaa ttc tac gtc aaa aag ggt gga gcc aag taa                  1479
Glu His Glu Phe Tyr Val Lys Lys Gly Gly Ala Lys
                485                 490

<210> SEQ ID NO 16
<211> LENGTH: 492
<212> TYPE: PRT
<213> ORGANISM: Artificial Sequence
<220> FEATURE:
<223> OTHER INFORMATION: Synthetic Construct

<400> SEQUENCE: 16

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Val Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Tyr Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Phe Tyr Arg Gly Ile Glu Pro Thr Leu
        115                 120                 125
```

```
Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys
                485                 490

<210> SEQ ID NO 17
<211> LENGTH: 1479
<212> TYPE: DNA
<213> ORGANISM: Artificial Sequence
<220> FEATURE:
<223> OTHER INFORMATION: pVD217 variant of Rep78 from AAV2
<220> FEATURE:
<221> NAME/KEY: CDS
```

<222> LOCATION: (1)..(1479)

<400> SEQUENCE: 17

```
acg gcg ggg ttc tac gag att gtg att aag gtc ccc agc gac ctt gac      48
Thr Ala Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
                20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
            35                  40                  45 gag cag gca ccc ctg acc gtg gcc gag aag ctg cag cgc gac ttt ctg     192
Glu Gln Ala Pro Leu Thr Val Ala Glu Lys Leu Gln Arg Asp Phe Leu
        50                  55                  60 acg gaa tgg cgc cgt gtg agt aag gcc ccg gag gcc ctt ttc tat gtg     240
Thr Glu Trp Arg Arg Val Ser Lys Ala Pro Glu Ala Leu Phe Tyr Val
65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att     336
Thr Thr Gly Val Lys Ser Met Val Leu Gly Arg Phe Leu Ser Gln Ile
                100                 105                 110 cgc gaa aaa ctg att cag aga ttt tac cgc ggg atc gag ccg act ttg     384
Arg Glu Lys Leu Ile Gln Arg Phe Tyr Arg Gly Ile Glu Pro Thr Leu
            115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
        130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta     528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat     576
Ser Ala Cys Leu Asn Leu Thr Glu Arg Lys Arg Leu Val Ala Gln His
                180                 185                 190 ctg acg cac gtg tcg cag acg cag gag cag aac aaa gag aat cag aat     624
Leu Thr His Val Ser Gln Thr Gln Glu Gln Asn Lys Glu Asn Gln Asn
            195                 200                 205 ccc aat tct gat gcg ccg gtg atc aga tca aaa act tca gcc agg tac     672
Pro Asn Ser Asp Ala Pro Val Ile Arg Ser Lys Thr Ser Ala Arg Tyr
        210                 215                 220 atg gag ctg gtc ggg tgg ctc gtg gac aag ggg att acc tcg gag aag     720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc     768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag     816
Ser Asn Ser Arg Ser Gln Ile Lys Ala Ala Leu Asp Asn Ala Gly Lys
                260                 265                 270 att atg agc ctg act aaa acc gcc ccc gac tac ctg gtg ggc cag cag     864
Ile Met Ser Leu Thr Lys Thr Ala Pro Asp Tyr Leu Val Gly Gln Gln
            275                 280                 285 ccc gtg gag gac att tcc agc aat cgg att tat aaa att ttg gaa cta     912
Pro Val Glu Asp Ile Ser Ser Asn Arg Ile Tyr Lys Ile Leu Glu Leu
        290                 295                 300
```

```
aac ggg tac gat ccc caa tat gcg gct tcc gtc ttt ctg gga tgg gcc    960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca   1008
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc   1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac   1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc   1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc   1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg   1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca   1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt   1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag   1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg   1440
Glu Val Lys Asp Phe Phe Arg Trp Ala Lys Asp His Val Val Glu Val
465                 470                 475                 480 gag cat gaa ttc tac gtc aaa aag ggt gga gcc aag taa               1479
Glu His Glu Phe Tyr Val Lys Lys Gly Gly Ala Lys
                485                 490

<210> SEQ ID NO 18
<211> LENGTH: 492
<212> TYPE: PRT
<213> ORGANISM: Artificial Sequence
<220> FEATURE:
<223> OTHER INFORMATION: Synthetic Construct

<400> SEQUENCE: 18

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Tyr Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110
```

```
Arg Glu Lys Leu Ile Gln Arg Phe Tyr Arg Gly Ile Glu Pro Thr Leu
            115                 120                 125
Pro Asn Trp Phe Ala Val Thr Lys Thr Arg Asn Gly Ala Gly Gly Gly
130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
                180                 185                 190
Leu Thr His Val Ser Gln Thr Gln Glu Gln Asn Lys Glu Asn Gln Asn
            195                 200                 205
Pro Asn Ser Asp Ala Pro Val Ile Arg Ser Lys Thr Ser Ala Arg Tyr
        210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
                260                 265                 270
Ile Met Ser Leu Thr Lys Thr Ala Pro Asp Tyr Leu Val Gly Gln Gln
            275                 280                 285
Pro Val Glu Asp Ile Ser Ser Asn Arg Ile Tyr Lys Ile Leu Glu Leu
        290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
            435                 440                 445
Glu Leu Thr Arg Arg Leu Asp His Asp Phe Gly Lys Val Thr Lys Gln
        450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys
                485                 490

<210> SEQ ID NO 19
<211> LENGTH: 1479
<212> TYPE: DNA
<213> ORGANISM: Artificial Sequence
<220> FEATURE:
```

<223> OTHER INFORMATION: pVD218 variant of Rep78 from AAV2
<220> FEATURE:
<221> NAME/KEY: CDS
<222> LOCATION: (1)..(1479)

<400> SEQUENCE: 19

| | | | | | | | | | | | | | | | | |
|---|---|---|---|---|---|---|---|---|---|---|---|---|---|---|---|---|
| acg | gcg | ggg | ttc | tac | gag | att | gtg | att | aag | gtc | ccc | agc | gac | ctt | gac | 48 |
| Thr | Ala | Gly | Phe | Tyr | Glu | Ile | Val | Ile | Lys | Val | Pro | Ser | Asp | Leu | Asp | |
| 1 | | | | 5 | | | | | 10 | | | | | 15 | | |
| gag | cat | ctg | ccc | ggc | att | tct | gac | agc | ttt | gtg | aac | tgg | gtg | gcc | gag | 96 |
| Glu | His | Leu | Pro | Gly | Ile | Ser | Asp | Ser | Phe | Val | Asn | Trp | Val | Ala | Glu | |
| | | | 20 | | | | | 25 | | | | | 30 | | | |
| aag | gaa | tgg | gag | ttg | ccg | cca | gat | tct | gac | atg | gat | ctg | aat | ctg | att | 144 |
| Lys | Glu | Trp | Glu | Leu | Pro | Pro | Asp | Ser | Asp | Met | Asp | Leu | Asn | Leu | Ile | |
| | | 35 | | | | | 40 | | | | | 45 | | | | |
| gag | cag | gca | ccc | ctg | acc | gtg | gcc | gag | aag | ctg | cag | cgc | gac | ttt | ctg | 192 |
| Glu | Gln | Ala | Pro | Leu | Thr | Val | Ala | Glu | Lys | Leu | Gln | Arg | Asp | Phe | Leu | |
| | 50 | | | | | 55 | | | | | 60 | | | | | |
| acg | gaa | tgg | cgc | cgt | gtg | agt | aag | gcc | ccg | gag | gcc | ctt | ttc | tat | gtg | 240 |
| Thr | Glu | Trp | Arg | Arg | Val | Ser | Lys | Ala | Pro | Glu | Ala | Leu | Phe | Tyr | Val | |
| 65 | | | | | 70 | | | | | 75 | | | | | 80 | |
| caa | ttt | gag | aag | gga | gag | agc | tac | ttc | cac | atg | cac | gtg | ctc | gtg | gaa | 288 |
| Gln | Phe | Glu | Lys | Gly | Glu | Ser | Tyr | Phe | His | Met | His | Val | Leu | Val | Glu | |
| | | | | 85 | | | | | 90 | | | | | 95 | | |
| acc | acc | ggg | gtg | aaa | tcc | atg | gtt | ttg | gga | cgt | ttc | ctg | agt | cag | att | 336 |
| Thr | Thr | Gly | Val | Lys | Ser | Met | Val | Leu | Gly | Arg | Phe | Leu | Ser | Gln | Ile | |
| | | | 100 | | | | | 105 | | | | | 110 | | | |
| cgc | gaa | aaa | ctg | att | cag | aga | ttt | tac | cgc | ggg | atc | gag | ccg | act | ttg | 384 |
| Arg | Glu | Lys | Leu | Ile | Gln | Arg | Phe | Tyr | Arg | Gly | Ile | Glu | Pro | Thr | Leu | |
| | | 115 | | | | | 120 | | | | | 125 | | | | |
| cca | aac | tgg | ttc | gcg | gtc | aca | aag | acc | aga | aat | ggc | gcc | gga | ggc | ggg | 432 |
| Pro | Asn | Trp | Phe | Ala | Val | Thr | Lys | Thr | Arg | Asn | Gly | Ala | Gly | Gly | Gly | |
| | 130 | | | | | 135 | | | | | 140 | | | | | |
| aac | aag | gtg | gtg | gat | gag | tgc | tac | atc | ccc | aat | tac | ttg | ctc | ccc | aaa | 480 |
| Asn | Lys | Val | Val | Asp | Glu | Cys | Tyr | Ile | Pro | Asn | Tyr | Leu | Leu | Pro | Lys | |
| 145 | | | | | 150 | | | | | 155 | | | | | 160 | |
| acc | cag | cct | gag | ctc | cag | tgg | gcg | tgg | act | aat | atg | gaa | cag | tat | tta | 528 |
| Thr | Gln | Pro | Glu | Leu | Gln | Trp | Ala | Trp | Thr | Asn | Met | Glu | Gln | Tyr | Leu | |
| | | | | 165 | | | | | 170 | | | | | 175 | | |
| agc | gcc | tgt | ttg | aat | ctc | acg | gag | cgt | aaa | cgg | ttg | gtg | gcg | cag | cat | 576 |
| Ser | Ala | Cys | Leu | Asn | Leu | Thr | Glu | Arg | Lys | Arg | Leu | Val | Ala | Gln | His | |
| | | | 180 | | | | | 185 | | | | | 190 | | | |
| ctg | acg | cac | gtg | tcg | cag | acg | cag | gag | cag | aac | aaa | gag | aat | cag | aat | 624 |
| Leu | Thr | His | Val | Ser | Gln | Thr | Gln | Glu | Gln | Asn | Lys | Glu | Asn | Gln | Asn | |
| | | 195 | | | | | 200 | | | | | 205 | | | | |
| ccc | aat | tct | gat | gcg | ccg | gtg | atc | aga | tca | aaa | act | tca | gcc | agg | tac | 672 |
| Pro | Asn | Ser | Asp | Ala | Pro | Val | Ile | Arg | Ser | Lys | Thr | Ser | Ala | Arg | Tyr | |
| | 210 | | | | | 215 | | | | | 220 | | | | | |
| atg | gag | ctg | gtc | ggg | tgg | ctc | gtg | gac | aag | ggg | att | acc | tcg | gag | aag | 720 |
| Met | Glu | Leu | Val | Gly | Trp | Leu | Val | Asp | Lys | Gly | Ile | Thr | Ser | Glu | Lys | |
| 225 | | | | | 230 | | | | | 235 | | | | | 240 | |
| cag | tgg | atc | cag | gag | gac | cag | gcc | tca | tac | atc | tcc | ttc | aat | gcg | gcc | 768 |
| Gln | Trp | Ile | Gln | Glu | Asp | Gln | Ala | Ser | Tyr | Ile | Ser | Phe | Asn | Ala | Ala | |
| | | | | 245 | | | | | 250 | | | | | 255 | | |
| tcc | aac | tcg | cgg | tcc | caa | atc | aag | gct | gcc | ttg | gac | aat | gcg | gga | aag | 816 |
| Ser | Asn | Ser | Arg | Ser | Gln | Ile | Lys | Ala | Ala | Leu | Asp | Asn | Ala | Gly | Lys | |
| | | | 260 | | | | | 265 | | | | | 270 | | | |
| att | atg | agc | ctg | act | aaa | acc | gcc | ccc | gac | tac | ctg | gtg | ggc | cag | cag | 864 |
| Ile | Met | Ser | Leu | Thr | Lys | Thr | Ala | Pro | Asp | Tyr | Leu | Val | Gly | Gln | Gln | |
| | | 275 | | | | | 280 | | | | | 285 | | | | |

```
ccc gtg gag gac att tcc agc aat cgg att tat aaa att ttg gaa cta    912
Pro Val Glu Asp Ile Ser Ser Asn Arg Ile Tyr Lys Ile Leu Glu Leu
    290                 295                 300 agc ggg tac gat ccc caa tat gcg gct tcc gtc ttt ctg gga tgg gcc    960
Ser Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca   1008
Thr Lys Lys Phe Gly Lys Arg Asn Thr Ile Trp Leu Phe Gly Pro Ala
                325                 330                 335 act acc ggg aag acc aac atc gcg gag gcc ata gcc cac act gtg ccc   1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac   1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc   1152
Cys Val Asp Lys Met Val Ile Trp Trp Glu Glu Gly Lys Met Thr Ala
    370                 375                 380 aag gtc gtg gag tcg gcc aaa gcc att ctc gga gga agc aag gtg cgc   1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg   1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca   1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt   1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag   1392
Glu Leu Thr Arg Arg Leu Asp His Asp Phe Gly Lys Val Thr Lys Gln
    450                 455                 460 gaa gtc aaa gac ttt ttc cgg tgg gca aag gat cac gtg gtt gag gtg   1440
Glu Val Lys Asp Phe Phe Arg Trp Ala Lys Asp His Val Val Glu Val
465                 470                 475                 480 gag cat gaa ttc tac gtc aaa aag ggt gga gcc aag taa                1479
Glu His Glu Phe Tyr Val Lys Lys Gly Gly Ala Lys
                485                 490

<210> SEQ ID NO 20
<211> LENGTH: 492
<212> TYPE: PRT
<213> ORGANISM: Artificial Sequence
<220> FEATURE:
<223> OTHER INFORMATION: Synthetic Construct

<400> SEQUENCE: 20

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Tyr Val
65                  70                  75                  80

Gln Phe Glu Lys Gly Glu Ser Tyr Phe His Met His Val Leu Val Glu
                85                  90                  95
```

Thr Thr Gly Val Lys Ser Met Val Leu Gly Arg Phe Leu Ser Gln Ile
            100                 105                 110

Arg Glu Lys Leu Ile Gln Arg Phe Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Ser Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys
                485                 490

<210> SEQ ID NO 21
<211> LENGTH: 1479

```
<212> TYPE: DNA
<213> ORGANISM: Artificial Sequence
<220> FEATURE:
<223> OTHER INFORMATION: pVD220 variant of Rep78 from AAV2
<220> FEATURE:
<221> NAME/KEY: CDS
<222> LOCATION: (1)..(1479)

<400> SEQUENCE: 21 acg gcg ggg ttc tac gag att gtg att aag gtc ccc agc gac ctt gac      48
Thr Ala Gly Phe Tyr Glu Ile Val Ile Lys Val Pro Ser Asp Leu Asp
 1               5                  10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
             20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
         35                  40                  45 gag cag gca ccc ctg acc gtg gcc ggg aag ctg cag cgc gac ttt ctg     192
Glu Gln Ala Pro Leu Thr Val Ala Gly Lys Leu Gln Arg Asp Phe Leu
     50                  55                  60 acg gaa tgg cgc cgt gtg agt aag gcc ccg gag gcc ctt ttc ttt gtg     240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                 85                  90                  95 ccc acc ggg gtg aaa tcc atg gtt ttg gga cgt ttc ctg agt cag att     336
Pro Thr Gly Val Lys Ser Met Val Leu Gly Arg Phe Leu Ser Gln Ile
            100                 105                 110 cgc gaa aaa ctg att cag aga att tac cgc ggg atc gag ccg act ttg     384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta     528
Thr Gln Pro Glu Leu Gln Trp Ala Trp Thr Asn Met Glu Gln Tyr Leu
                165                 170                 175 agc gcc cgt ttg aat ctc acg gag cgt aaa cgg ttg gtg gcg cag cat     576
Ser Ala Arg Leu Asn Leu Thr Glu Arg Lys Arg Leu Val Ala Gln His
            180                 185                 190 ctg acg cac gtg tcg cag acg cag gag cag aac aaa gag aat cag aat     624
Leu Thr His Val Ser Gln Thr Gln Glu Gln Asn Lys Glu Asn Gln Asn
        195                 200                 205 ccc aat tct gat gcg cct gtg atc aga tca aaa act tca gcc agg tac     672
Pro Asn Ser Asp Ala Pro Val Ile Arg Ser Lys Thr Ser Ala Arg Tyr
    210                 215                 220 atg gag ctg gtc ggg tgg ctc gtg gac aag ggg att acc tcg gag aag     720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc     768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag     816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag     864
```

```
Ile Met Ser Leu Thr Lys Thr Ala Pro Asp Tyr Leu Val Gly Gln Gln
            275                 280                 285 ccc gtg gag gac att tcc agc aat cgg att tat aaa att ttg gaa cta      912
Pro Val Glu Asp Ile Ser Ser Asn Arg Ile Tyr Lys Ile Leu Glu Leu
290                 295                 300 aac ggg tac gat ccc caa tat gcg gct tcc gtc ttt ctg gga tgg gcc      960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca     1008
Thr Lys Lys Phe Gly Lys Arg Asn Thr Ile Trp Leu Phe Gly Pro Ala
            325                 330                 335 act acc ggg aag acc aac atc gcg gag gcc ata gcc cac act gtg ccc     1056
Thr Thr Gly Lys Thr Asn Ile Ala Glu Ala Ile Ala His Thr Val Pro
            340                 345                 350 ttc tac ggg tgc gta aac tgg acc aat gag aac ttt ccc ttc aac gac     1104
Phe Tyr Gly Cys Val Asn Trp Thr Asn Glu Asn Phe Pro Phe Asn Asp
            355                 360                 365 tgt gtc gac aag atg gtg atc tgg tgg gag gag ggg aag atg acc gcc     1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc     1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg     1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca     1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt     1344
Thr Thr Phe Glu His Gln Gln Pro Leu Gln Asp Arg Met Phe Lys Phe
            435                 440                 445 gaa ctc acc cgc cgt ctg gat cat gac ttt ggg aag gtc acc aag cag     1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg     1440
Glu Val Lys Asp Phe Phe Arg Trp Ala Lys Asp His Val Val Glu Val
465                 470                 475                 480 gag cat gaa ttc tac gtc aaa aag ggt gga gcc aag taa                 1479
Glu His Glu Phe Tyr Val Lys Lys Gly Gly Ala Lys
                485                 490

<210> SEQ ID NO 22
<211> LENGTH: 492
<212> TYPE: PRT
<213> ORGANISM: Artificial Sequence
<220> FEATURE:
<223> OTHER INFORMATION: Synthetic Construct

<400> SEQUENCE: 22

Thr Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Gly Lys Leu Gln Arg Asp Phe Leu
        50                  55                  60

Thr Glu Trp Arg Arg Val Ser Lys Ala Pro Glu Ala Leu Phe Phe Val
65                  70                  75                  80
```

```
Gln Phe Glu Lys Gly Glu Ser Tyr Phe His Met His Val Leu Val Glu
                 85                  90                  95

Pro Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Arg Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys
                485                 490
```

<210> SEQ ID NO 23
<211> LENGTH: 36
<212> TYPE: DNA
<213> ORGANISM: Artificial
<220> FEATURE:
<223> OTHER INFORMATION: AMT primer #327

<400> SEQUENCE: 23
tccggactct agaggacctt taattcaacc caacac                                36

<210> SEQ ID NO 24
<211> LENGTH: 36
<212> TYPE: DNA
<213> ORGANISM: Artificial
<220> FEATURE:
<223> OTHER INFORMATION: AMT primer #332

<400> SEQUENCE: 24
gccttcgctc gagctccttt gattgtaaat aaaatg                                36

<210> SEQ ID NO 25
<211> LENGTH: 32
<212> TYPE: DNA
<213> ORGANISM: Artificial
<220> FEATURE:
<223> OTHER INFORMATION: AMT primer #321

<400> SEQUENCE: 25
caaaaaagca ggctcctgtt aagacggcgg gg                                    32

<210> SEQ ID NO 26
<211> LENGTH: 39
<212> TYPE: DNA
<213> ORGANISM: Artificial
<220> FEATURE:
<223> OTHER INFORMATION: AMT primer #322

<400> SEQUENCE: 26
tacaagaaag ctgggtttat tgttcaaaga tgcagtcat                             39

<210> SEQ ID NO 27
<211> LENGTH: 36
<212> TYPE: DNA
<213> ORGANISM: Artificial
<220> FEATURE:
<223> OTHER INFORMATION: AMT primer #323

<400> SEQUENCE: 27
ggggacaagt ttgtacaaaa aagcaggctc ctgtta                                36

<210> SEQ ID NO 28
<211> LENGTH: 35
<212> TYPE: DNA
<213> ORGANISM: Artificial
<220> FEATURE:
<223> OTHER INFORMATION: AMT primer #324

<400> SEQUENCE: 28
ggggaccact ttgtacaaga aagctgggtt tattg                                 35

<210> SEQ ID NO 29
<211> LENGTH: 19
<212> TYPE: DNA
<213> ORGANISM: Artificial
<220> FEATURE:
<223> OTHER INFORMATION: AMT primer #210

<400> SEQUENCE: 29
aggcccaaac agccagatg                                                        19

<210> SEQ ID NO 30
<211> LENGTH: 22
<212> TYPE: DNA
<213> ORGANISM: Artificial
<220> FEATURE:
<223> OTHER INFORMATION: AMT primer #349

<400> SEQUENCE: 30
gcggatcatc acaagtttgt ac                                                    22

<210> SEQ ID NO 31
<211> LENGTH: 22
<212> TYPE: DNA
<213> ORGANISM: Artificial
<220> FEATURE:
<223> OTHER INFORMATION: AMT primer #350

<400> SEQUENCE: 31
accactttgt acaagaaagc tg                                                    22

<210> SEQ ID NO 32
<211> LENGTH: 21
<212> TYPE: DNA
<213> ORGANISM: Artificial
<220> FEATURE:
<223> OTHER INFORMATION: AMT primer Pr180

<400> SEQUENCE: 32
cgaaccgatg gctggactat c                                                     21

<210> SEQ ID NO 33
<211> LENGTH: 23
<212> TYPE: DNA
<213> ORGANISM: Artificial
<220> FEATURE:
<223> OTHER INFORMATION: AMT primer Pr181

<400> SEQUENCE: 33
tgctgctaca agatttggca agt                                                   23

<210> SEQ ID NO 34
<211> LENGTH: 22
<212> TYPE: DNA
<213> ORGANISM: Artificial
<220> FEATURE:
<223> OTHER INFORMATION: AMT primer Pr209

<400> SEQUENCE: 34
ctaaacgggt acgatcccca at                                                    22

<210> SEQ ID NO 35
<211> LENGTH: 26
<212> TYPE: DNA
<213> ORGANISM: Artificial
<220> FEATURE:
<223> OTHER INFORMATION: forward primer pr460

<400> SEQUENCE: 35
tacgagattg tgattaaggt ccccag                                                26

<210> SEQ ID NO 36

```
<211> LENGTH: 35
<212> TYPE: DNA
<213> ORGANISM: Artificial
<220> FEATURE:
<223> OTHER INFORMATION: reverse primer pr461

<400> SEQUENCE: 36
catcactcta gacttacttg gctccaccct ttttg                          35

<210> SEQ ID NO 37
<211> LENGTH: 20
<212> TYPE: DNA
<213> ORGANISM: Artificial
<220> FEATURE:
<223> OTHER INFORMATION: reverse primer pr462

<400> SEQUENCE: 37
gctgctggcc caccaggtag                                           20

<210> SEQ ID NO 38
<211> LENGTH: 36
<212> TYPE: DNA
<213> ORGANISM: Artificial
<220> FEATURE:
<223> OTHER INFORMATION: reverse primer pr463

<400> SEQUENCE: 38
catcactcta gaatcactct aaacagtctt tctgtc                         36

<210> SEQ ID NO 39
<211> LENGTH: 59
<212> TYPE: DNA
<213> ORGANISM: Artificial
<220> FEATURE:
<223> OTHER INFORMATION: Primer pr487

<400> SEQUENCE: 39
catcactcta gattatcaga gagagtgtcc tcgagccaat ctgtctgcgt agttgatcg   59

<210> SEQ ID NO 40
<211> LENGTH: 19
<212> TYPE: DNA
<213> ORGANISM: Artificial
<220> FEATURE:
<223> OTHER INFORMATION: primer Pr59

<400> SEQUENCE: 40
aatgggcggt aggcgtgta                                            19

<210> SEQ ID NO 41
<211> LENGTH: 22
<212> TYPE: DNA
<213> ORGANISM: Artificial
<220> FEATURE:
<223> OTHER INFORMATION: primer Pr60

<400> SEQUENCE: 41
aggcgatctg acggttcact aa                                        22

<210> SEQ ID NO 42
<211> LENGTH: 25
<212> TYPE: DNA
<213> ORGANISM: Artificial
<220> FEATURE:
<223> OTHER INFORMATION: Primer Pr406

<400> SEQUENCE: 42
```

```
acagccattg taatgagacg cacaa                                              25

<210> SEQ ID NO 43
<211> LENGTH: 25
<212> TYPE: DNA
<213> ORGANISM: Artificial
<220> FEATURE:
<223> OTHER INFORMATION: Primer Pr407

<400> SEQUENCE: 43
cctagcgccc gatcagcaac tatat                                              25

<210> SEQ ID NO 44
<211> LENGTH: 20
<212> TYPE: DNA
<213> ORGANISM: Artificial
<220> FEATURE:
<223> OTHER INFORMATION: primer Pr340

<400> SEQUENCE: 44
atacaaccgt tggttgcacg                                                    20

<210> SEQ ID NO 45
<211> LENGTH: 18
<212> TYPE: DNA
<213> ORGANISM: Artificial
<220> FEATURE:
<223> OTHER INFORMATION: primer Pr341

<400> SEQUENCE: 45
cgggacacgc catgtatt                                                      18
```